(12) United States Patent
Okuse et al.

(10) Patent No.: US 7,563,586 B2
(45) Date of Patent: Jul. 21, 2009

(54) METHOD OF IDENTIFYING A MODULATOR OF A VOLTAGE-GATED SODIUM CHANNEL USING CELLS EXPRESSING NAV1.8 AND P11

(75) Inventors: Kenji Okuse, London (GB); Mark Baker, London (GB); Louisa Poon, London (GB); John Nicholas Wood, London (GB); Misbah Malik-Hall, London (GB)

(73) Assignee: University College London, London (GB)

( * ) Notice: Subject to any disclaimer, the term of this patent is extended or adjusted under 35 U.S.C. 154(b) by 585 days.

(21) Appl. No.: 10/487,337

(22) PCT Filed: Aug. 20, 2002

(86) PCT No.: PCT/GB02/03852

§ 371 (c)(1),
(2), (4) Date: Jul. 13, 2004

(87) PCT Pub. No.: WO03/016917

PCT Pub. Date: Feb. 27, 2003

(65) Prior Publication Data

US 2004/0248207 A1    Dec. 9, 2004

(30) Foreign Application Priority Data

Aug. 20, 2001    (GB)    ................................. 0120238.1

(51) Int. Cl.
*G01N 33/566*    (2006.01)
*C12N 1/15*    (2006.01)
*C12N 1/21*    (2006.01)
*C12N 5/16*    (2006.01)
*C12N 5/18*    (2006.01)
*C12N 5/22*    (2006.01)

(52) U.S. Cl. ................. 435/7.21; 435/252.3; 435/254.2; 435/353; 435/361; 435/365; 435/366; 435/368

(58) Field of Classification Search ........................ None
See application file for complete search history.

(56) References Cited

U.S. PATENT DOCUMENTS 5,616,500 A * 4/1997 Steinert et al. ............ 435/320.1
5,892,018 A    4/1999 Welsh et al.
5,990,295 A    11/1999 Olivera et al.
6,184,349 B1    2/2001 Herman et al.

FOREIGN PATENT DOCUMENTS

WO         97/01577 A    1/1997
WO    WO 0035473 A2 *    6/2000
WO         01/57024 A    8/2001

OTHER PUBLICATIONS

Wood et al, 2004. J Neurobiol. 61: 55-71: 2004.*
Poon et al (2004. FEBS Letters. 558: 114-118).*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398-400.*
Skolnick and Fetrow (2000) Trends in Biotech. 18(1):34-39.*
Doerks et al. (Jun. 1998) Trends in Genetics 14(6): 248-250.*
Smith and Zhang (Nov. 1997) Nature Biotechnology 15:1222-1223.*
Brenner (Apr. 1999) Trends in Genetics 15(4): 132-133.*
Bork and Bairoch (Oct. 1996) Trends in Genetics 12(10): 425-427.*
Wang et al. (Nuc. Acids Res. 27: 4609-4618, 1999.*
Kaufman et al (Blood 94: 3178-3184, 1999).*
Phillips, A., J Pharm Pharmacology 53: 1169-1174, 2001.*
McLean et al, 1988. Molecular and Cellular Biochemistry. 80: 95-107.*
Stuhmer (1991. Annu Rev Biophys Biophys Chem. 20: 65-78).*
England et al (1998. Journal of Physiology. vol. 511P, p. 124P.*
Sosa et al (1998. Neurosurgery. 43(3). Originally pp. 681-686, 9 pages as printed from on-line full-text version).*
Sangameswaran et al, 1996. Journal of Biological Chemistry. 271(11): 5953-5956.*
Okuse et al; "Annexin II Light Chain Regulates Sensory Neuron-Specific Sodium Channel Expression"; Nature, England, Jun. 6, 2002, vol. 417, No. 6889, pp. 653-656, XP001121255.
International Search Report of PCT/GB02/03852 filed Aug. 20, 2002.
Akiba et al. "Transforming growth factor-α stimulates prostaglandin generation through cytosolic phospholipase $A_2$ under the control of p11 in rat gastric epithelial cells" Brit. J. Pharmacol. 131:1004-1010 (2000).
Akopian et al. "A tetrodotoxin-resistant voltage-gated sodium channel expressed by sensory neurons" Accession No. X92184 Nature 379:257-262 (1996).
Akopian et al. "The tetrodotoxin-resistant sodium channel SNS has a specialized function in pain pathways" Nature Neurosci. 2:541-548 (1999).
Black et al. "NGF has opposing effects on Na channel III and SNS gene expression in spinal sensory neurons" NeuroReport 8:2331-2335 (1997).

(Continued)

*Primary Examiner*—Bridget E Bunner
*Assistant Examiner*—Zachary C Howard
(74) *Attorney, Agent, or Firm*—Nixon & Vanderhye P.C.

(57) ABSTRACT

The present invention provides a method of identifying a modulator of a voltage gated sodium channel (VGSC), which method comprises bringing into contact a VGSC, a p11 peptide and a test compound under conditions where the VGSC and the p11 peptide are capable of forming a complex in the absence of the test compound; and measuring an activity of the VGSC, wherein a change in the activity of the VGSC relative to the activity in the absence of the test compound indicates that the test compound is a modulator of said VGSC. Compounds identified in such screening methods are proposed for use in the treatment of VGSC-related conditions, for example in the treatment or prevention of pain. Also provided are methods of enhancing the functional expression of a voltage gated sodium channel (VGSC) in a cell comprising the step of increasing the level of p11 in the cell.

22 Claims, 2 Drawing Sheets

OTHER PUBLICATIONS

Dib-Hajj et al. "A novel voltage-gated Na channel, is expressed preferentially in peripheral sensory neurons and down-regulated after axotomy" Accession No. AF059030 Proc. Natl. Acad, Sci. USA 95:8963-8968 (1998).

Fang et al. "Sensory and electrophysiological properties of DRG neurones with SNS-like immunoreactivity (SNS-Li) in rats" Society for Neuroscience's meeting, Abstract 819.6 (2001).

Fitzgerald et al. "cAMP-dependent phosphorylation of the tetrodotoxin-resistant voltage-dependent sodium channel SNS" J. Physiol. 516:433-446 (1999).

Fjell et al. "In vivo NGF deprivation reduces SNS expression and TTX-R sodium currents in IB4-negative DRG neurons" J. Neurophysiol. 81:803-810 (1999).

Kayano et al. "Primary structure of rat brain sodium channell III deduced from the cDNA sequence" Accession No. Y00766 FEBS Lett. 228:187-194 (1988).

Kong et al. "An evolutionarily conserved transmembrane protein that is a novel downstream target of neurotrophin and ephrin receptors" J. Neurosci. 21:176-185 (2001).

Lewin et al. "Peripheral and central mechanisms of NGF-induced hyperalgesia" Eur. J. Neurosci. 6:1903-1912 (1994).

Liu et al. "Fibroblast growth factor homologous factor 1B binds to the C terminus of the tetrodotoxin-resistant sodium channel $rNA_v1.9a$ (NaN)" J. Biol. Chem. 276:18925-18933 (2001).

MacLeod et al. "Phospholipid-associated annexin A2-S100A10 heterotetramer and its subunits: Characterization of the interaction with tissue plasminogen activator, plasminogen an plasmin" J. Biol. Chem. 278:25577-25584 (2003).

Masiakowski et al. "Nerve growth factor induces the genes for two proteins related to a family calcium-binding proteins in PC12 cells" Accession No. J03627 Proc. Natl. Acad. Sci. USA 85:1277-1281 (1988).

McMahon et al. "The biological effects of endogenous nerve growth factor on adult sensory neurons revealed by a trkA-IgG fusion molecule" Nature Medicine 1:774-780 (1995).

Masiakowski et al. "Nerve growth factor induces the genes for two proteins related to a family of calcium-binding proteins in PC12 cells" Proc. Natl. Acad. Sci. USA 85:1277-1281 (1988).

Moreno "Antiflammin peptides in the regulation of inflammatory response" Ann. N.Y. Acad. Sci. 923:47-53 (2000).

Okuse et al. "Regulation of expression of the sensory neuron-specific sodium channel SNS in inflammatory and neuropathic pain" Mol. Cell. Neurosci. 10:196-207 (1997).

Osborn et al. "The submembranous location of p11 and its interaction with the p36 substrate of pp60 src kinase in situ" Exp. Cell Res. 175:81-96 (1988).

Rabert et al. "A tetrodotoxin-resistant voltage-gated sodium channel from human dorsal root ganglia, hPN3/SCN10A" Accession No. AF117907 Pain 78:107-114 (1998).

Réty et al. "The crystal structure of a complex of p11 with the annexin II N-terminal peptide" Nature Structural Biology 6:89-95 (1999).

Rogart et al. "Molecular cloning of a putative tetrodotoxin-resistant rat heart Na channel isoform" Accession No. M27902 Proc. Natl. Acad. Sci. USA 86:8170-8174 (1989).

Waisman et al. "Annexin II tetramer: Structure and function" Mol. Cell. Biochem. 149/150:301-322 (1995).

Wu et al. "p11, a unique member of the S100 family of calcium-binding proteins, interacts with and inhibits the activity of the 85-kDa cytosolic phospholipase $A_2$" J. Biol. Chem. 272:17145-17153 (1997).

Wood et al. "Voltage-gated sodium channels" Curr. Opin. Pharmacol. 1:17-21 (2001).

* cited by examiner

SEQUENCE LISTING

```
<160> NUMBER OF SEQ ID NOS: 55

<210> SEQ ID NO 1
<211> LENGTH: 6524
<212> TYPE: DNA
<213> ORGANISM: Rattus norvegicus
<220> FEATURE:
<221> NAME/KEY: CDS
<222> LOCATION: (204)..(6074)
<223> OTHER INFORMATION:

<400> SEQUENCE: 1
tagcttgctt ctgctaatgc tacccaggc ctttagacag agaacagatg gcagatggag      60
tttcttattg ccatgcgcaa acgctgagcc cacctcatga tcccggaccc catggttttc     120
agtagacaac ctgggctaag aagagatctc cgaccttata gagcagcaaa gagtgtaaat    180
tcttccccaa gaagaatgag aag atg gag ctc ccc ttt gcg tcc gtg gga act    233
                         Met Glu Leu Pro Phe Ala Ser Val Gly Thr
                         1               5                   10 acc aat ttc aga cgg ttc act cca gag tca ctg gca gag atc gag aag      281
Thr Asn Phe Arg Arg Phe Thr Pro Glu Ser Leu Ala Glu Ile Glu Lys
             15                  20                  25 cag att gct gct cac cgc gca gcc aag aag gcc aga acc aag cac aga      329
Gln Ile Ala Ala His Arg Ala Ala Lys Lys Ala Arg Thr Lys His Arg
         30                  35                  40 gga cag gag gac aag ggc gag aag ccc agg cct cag ctg gac ttg aaa      377
Gly Gln Glu Asp Lys Gly Glu Lys Pro Arg Pro Gln Leu Asp Leu Lys
     45                  50                  55
```

-continued

| | |
|---|---|
| gac tgt aac cag ctg ccc aag ttc tat ggt gag ctc cca gca gaa ctg<br>Asp Cys Asn Gln Leu Pro Lys Phe Tyr Gly Glu Leu Pro Ala Glu Leu<br>60                 65                 70 | 425 |
| gtc ggg gag ccc ctg gag gac cta gac cct ttc tac agc aca cac cgg<br>Val Gly Glu Pro Leu Glu Asp Leu Asp Pro Phe Tyr Ser Thr His Arg<br>75               80               85             90 | 473 |
| aca ttc atg gtg ttg aat aaa agc agg acc att tcc aga ttc agt gcc<br>Thr Phe Met Val Leu Asn Lys Ser Arg Thr Ile Ser Arg Phe Ser Ala<br>           95                 100             105 | 521 |
| act tgg gcc ctg tgg ctc ttc agt ccc ttc aac ctg atc aga aga aca<br>Thr Trp Ala Leu Trp Leu Phe Ser Pro Phe Asn Leu Ile Arg Arg Thr<br>       110                115             120 | 569 |
| gcc atc aaa gtg tct gtc cat tcc tgg ttc tcc ata ttc atc acc atc<br>Ala Ile Lys Val Ser Val His Ser Trp Phe Ser Ile Phe Ile Thr Ile<br>           125               130             135 | 617 |
| act att ttg gtc aac tgc gtg tgc atg acc cga act gat ctt cca gag<br>Thr Ile Leu Val Asn Cys Val Cys Met Thr Arg Thr Asp Leu Pro Glu<br>140                 145               150 | 665 |
| aaa gtc gag tac gtc ttc act gtc att tac acc ttc gag gct ctg att<br>Lys Val Glu Tyr Val Phe Thr Val Ile Tyr Thr Phe Glu Ala Leu Ile<br>155                 160               165             170 | 713 |
| aag ata ctg gca aga ggg ttt tgt cta aat gag ttc act tat ctt cga<br>Lys Ile Leu Ala Arg Gly Phe Cys Leu Asn Glu Phe Thr Tyr Leu Arg<br>           175               180             185 | 761 |
| gat ccg tgg aac tgg ctg gac ttc agt gtc att acc ttg gcg tat gtg<br>Asp Pro Trp Asn Trp Leu Asp Phe Ser Val Ile Thr Leu Ala Tyr Val<br>             190               195             200 | 809 |
| ggt gca gcg ata gac ctc cga gga atc tca ggc ctg cgg aca ttc cga<br>Gly Ala Ala Ile Asp Leu Arg Gly Ile Ser Gly Leu Arg Thr Phe Arg<br>205                 210               215 | 857 |
| gtt ctc aga gcc ctg aaa act gtt tct gtg atc cca gga ctg aag gtc<br>Val Leu Arg Ala Leu Lys Thr Val Ser Val Ile Pro Gly Leu Lys Val<br>220                 225               230 | 905 |
| atc gtg gga gcc ctg atc cac tca gtg agg aag ctg gcc gac gtg act<br>Ile Val Gly Ala Leu Ile His Ser Val Arg Lys Leu Ala Asp Val Thr<br>235                 240               245             250 | 953 |
| atc ctc aca gtc ttc tgc ctg agc gtc ttc gcc ttg gtg ggc ctg cag<br>Ile Leu Thr Val Phe Cys Leu Ser Val Phe Ala Leu Val Gly Leu Gln<br>           255               260             265 | 1001 |
| ctc ttt aag ggg aac ctt aag aac aaa tgc atc agg aac gga aca gat<br>Leu Phe Lys Gly Asn Leu Lys Asn Lys Cys Ile Arg Asn Gly Thr Asp<br>       270                275             280 | 1049 |
| ccc cac aag gct gac aac ctc tca tct gaa atg gca gaa tac atc ttc<br>Pro His Lys Ala Asp Asn Leu Ser Ser Glu Met Ala Glu Tyr Ile Phe<br>           285               290             295 | 1097 |
| atc aag cct ggt act acg gat ccc tta ctg tgc ggc aat ggg tct gat<br>Ile Lys Pro Gly Thr Thr Asp Pro Leu Leu Cys Gly Asn Gly Ser Asp<br>300                 305               310 | 1145 |
| gct ggt cac tgc cct gga ggc tat gtc tgc ctg aaa act cct gac aac<br>Ala Gly His Cys Pro Gly Gly Tyr Val Cys Leu Lys Thr Pro Asp Asn<br>315                 320               325             330 | 1193 |
| ccg gat ttt aac tac acc agc ttt gat tcc ttt gcg tgg gca ttc ctc<br>Pro Asp Phe Asn Tyr Thr Ser Phe Asp Ser Phe Ala Trp Ala Phe Leu<br>           335               340             345 | 1241 |
| tca ctg ttc cgc ctc atg acg cag gac tcc tgg gag cgc ctg tac cag<br>Ser Leu Phe Arg Leu Met Thr Gln Asp Ser Trp Glu Arg Leu Tyr Gln<br>       350                355             360 | 1289 |
| cag aca ctc cgg gct tct ggg aaa atg tac atg gtc ttt ttc gtg ctg<br>Gln Thr Leu Arg Ala Ser Gly Lys Met Tyr Met Val Phe Phe Val Leu | 1337 |

-continued

```
              365                 370                 375
gtt att ttc ctt gga tcg ttc tac ctg gtc aat ttg atc ttg gcc gtg       1385
Val Ile Phe Leu Gly Ser Phe Tyr Leu Val Asn Leu Ile Leu Ala Val
    380                 385                 390 gtc acc atg gcg tat gaa gag cag agc cag gca aca att gca gaa atc       1433
Val Thr Met Ala Tyr Glu Glu Gln Ser Gln Ala Thr Ile Ala Glu Ile
395                 400                 405                 410 gaa gcc aag gaa aaa aag ttc cag gaa gcc ctt gag gtg ctg cag aag       1481
Glu Ala Lys Glu Lys Lys Phe Gln Glu Ala Leu Glu Val Leu Gln Lys
                415                 420                 425 gaa cag gag gtg ctg gaa gcc ctg ggg att gac acg acc tcg ctc cag       1529
Glu Gln Glu Val Leu Glu Ala Leu Gly Ile Asp Thr Thr Ser Leu Gln
            430                 435                 440 tcc cac agt gga tca ccc tta gcc tcc aaa aac gcc aat gag aga aga       1577
Ser His Ser Gly Ser Pro Leu Ala Ser Lys Asn Ala Asn Glu Arg Arg
        445                 450                 455 ccc agg gtg aaa tca agg gtg tca gag ggc tcc acg gat gac aac agg       1625
Pro Arg Val Lys Ser Arg Val Ser Glu Gly Ser Thr Asp Asp Asn Arg
    460                 465                 470 tca ccc caa tct gac cct tac aac cag cgc agg atg tct ttc cta ggc       1673
Ser Pro Gln Ser Asp Pro Tyr Asn Gln Arg Arg Met Ser Phe Leu Gly
475                 480                 485                 490 ctg tct tca gga aga cgc agg gct agc cac ggc agt gtg ttc cac ttc       1721
Leu Ser Ser Gly Arg Arg Arg Ala Ser His Gly Ser Val Phe His Phe
                495                 500                 505 cga gcg ccc agc caa gac atc tca ttt cct gac ggg atc acc cct gat       1769
Arg Ala Pro Ser Gln Asp Ile Ser Phe Pro Asp Gly Ile Thr Pro Asp
            510                 515                 520 gat ggg gtc ttt cac gga gac cag gaa agc cgt cga ggt tcc ata ttg       1817
Asp Gly Val Phe His Gly Asp Gln Glu Ser Arg Arg Gly Ser Ile Leu
        525                 530                 535 ctg ggc agg ggt gct ggg cag aca ggt cca ctc ccc agg agc cca ctg       1865
Leu Gly Arg Gly Ala Gly Gln Thr Gly Pro Leu Pro Arg Ser Pro Leu
    540                 545                 550 cct cag tcc ccc aac cct ggc cgt aga cat gga gaa gag gga cag ctc       1913
Pro Gln Ser Pro Asn Pro Gly Arg Arg His Gly Glu Glu Gly Gln Leu
555                 560                 565                 570 gga gtg ccc act ggt gag ctt acc gct gga gcg cct gaa ggc ccg gca       1961
Gly Val Pro Thr Gly Glu Leu Thr Ala Gly Ala Pro Glu Gly Pro Ala
                575                 580                 585 ctg cac act aca ggg cag aag agc ttc ctg tct gcg ggc tac ttg aac       2009
Leu His Thr Thr Gly Gln Lys Ser Phe Leu Ser Ala Gly Tyr Leu Asn
            590                 595                 600 gaa cct ttc cga gca cag agg gcc atg agc gtt gtc agt atc atg act       2057
Glu Pro Phe Arg Ala Gln Arg Ala Met Ser Val Val Ser Ile Met Thr
        605                 610                 615 tct gtc att gag gag ctt gaa gag tct aag ctg aag tgc cca ccc tgc       2105
Ser Val Ile Glu Glu Leu Glu Glu Ser Lys Leu Lys Cys Pro Pro Cys
    620                 625                 630 ttg atc agc ttc gct cag aag tat ctg atc tgg gag tgc tgc ccc aag       2153
Leu Ile Ser Phe Ala Gln Lys Tyr Leu Ile Trp Glu Cys Cys Pro Lys
635                 640                 645                 650 tgg agg aag ttc aag atg gcg ctg ttc gag ctg gtg act gac ccc ttc       2201
Trp Arg Lys Phe Lys Met Ala Leu Phe Glu Leu Val Thr Asp Pro Phe
                655                 660                 665 gca gag ctt acc atc acc ctc tgc atc gtg gtg aac acc gtc ttc atg       2249
Ala Glu Leu Thr Ile Thr Leu Cys Ile Val Val Asn Thr Val Phe Met
            670                 675                 680 gcc atg gag cac tac ccc atg acc gat gcc ttc gat gcc atg ctt caa       2297
```

```
                Ala Met Glu His Tyr Pro Met Thr Asp Ala Phe Asp Ala Met Leu Gln
                            685                 690                 695 gcc ggc aac att gtc ttc acc gtg ttt ttc aca atg gag atg gcc ttc              2345
Ala Gly Asn Ile Val Phe Thr Val Phe Phe Thr Met Glu Met Ala Phe
700                 705                 710 aag atc att gcc ttc gac ccc tac tat tac ttc cag aag aag tgg aat              2393
Lys Ile Ile Ala Phe Asp Pro Tyr Tyr Tyr Phe Gln Lys Lys Trp Asn
715                 720                 725                 730 atc ttc gac tgt gtc atc gtc acc gtg agc ctt ctg gag ctg agt gca              2441
Ile Phe Asp Cys Val Ile Val Thr Val Ser Leu Leu Glu Leu Ser Ala
                735                 740                 745 tcc aag aag ggc agc ctg tct gtg ctc cgt acc tta cgc ttg ctg cgg              2489
Ser Lys Lys Gly Ser Leu Ser Val Leu Arg Thr Leu Arg Leu Leu Arg
            750                 755                 760 gtc ttc aag ctg gcc aag tcc tgg ccc acc ctg aac acc ctc atc aag              2537
Val Phe Lys Leu Ala Lys Ser Trp Pro Thr Leu Asn Thr Leu Ile Lys
        765                 770                 775 atc atc ggg aac tca gtg ggg gcc ctg ggc aac ctg acc ttt atc ctg              2585
Ile Ile Gly Asn Ser Val Gly Ala Leu Gly Asn Leu Thr Phe Ile Leu
    780                 785                 790 gcc atc atc gtc ttc atc ttc gcc ctg gtc gga aag cag ctt ctc tca              2633
Ala Ile Ile Val Phe Ile Phe Ala Leu Val Gly Lys Gln Leu Leu Ser
795                 800                 805                 810 gag gac tac ggg tgc cgc aag gac ggc gtc tcc gtg tgg aac ggc gag              2681
Glu Asp Tyr Gly Cys Arg Lys Asp Gly Val Ser Val Trp Asn Gly Glu
                815                 820                 825 aag ctc cgc tgg cac atg tgt gac ttc ttc cat tcc ttc ctg gtc gtc              2729
Lys Leu Arg Trp His Met Cys Asp Phe Phe His Ser Phe Leu Val Val
            830                 835                 840 ttc cga atc ctc tgc ggg gag tgg atc gag aac atg tgg gtc tgc atg              2777
Phe Arg Ile Leu Cys Gly Glu Trp Ile Glu Asn Met Trp Val Cys Met
        845                 850                 855 gag gtc agc cag aaa tcc atc tgc ctc atc ctc ttc ttg act gtg atg              2825
Glu Val Ser Gln Lys Ser Ile Cys Leu Ile Leu Phe Leu Thr Val Met
    860                 865                 870 gtg ctg ggc aac cta gtg gtg ctc aac ctt ttc atc gct tta ctg ctg              2873
Val Leu Gly Asn Leu Val Val Leu Asn Leu Phe Ile Ala Leu Leu Leu
875                 880                 885                 890 aac tcc ttc agc gcg gac aac ctc acg gct cca gag gat gac ggg gag              2921
Asn Ser Phe Ser Ala Asp Asn Leu Thr Ala Pro Glu Asp Asp Gly Glu
                895                 900                 905 gtg aac aac ttg cag tta gca ctg gcc agg atc cag gta ctt ggc cat              2969
Val Asn Asn Leu Gln Leu Ala Leu Ala Arg Ile Gln Val Leu Gly His
            910                 915                 920 cgg gcc agc agg gcc atc gcc agt tac atc agc agc cac tgc cga ttc              3017
Arg Ala Ser Arg Ala Ile Ala Ser Tyr Ile Ser Ser His Cys Arg Phe
        925                 930                 935 cac tgg ccc aag gtg gag acc cag ctg ggc atg aag ccc cca ctc acc              3065
His Trp Pro Lys Val Glu Thr Gln Leu Gly Met Lys Pro Pro Leu Thr
    940                 945                 950 agc tca gag gcc aag aac cac att gcc act gat gct gtc agt gct gca              3113
Ser Ser Glu Ala Lys Asn His Ile Ala Thr Asp Ala Val Ser Ala Ala
955                 960                 965                 970 gtg ggg aac ctg aca aag cca gct ctc agt agc ccc aag gag aac cac              3161
Val Gly Asn Leu Thr Lys Pro Ala Leu Ser Ser Pro Lys Glu Asn His
                975                 980                 985 ggg gac ttc atc act gat ccc aac gtg tgg gtc tct gtg ccc att gct              3209
Gly Asp Phe Ile Thr Asp Pro Asn Val Trp Val Ser Val Pro Ile Ala
            990                 995                 1000
```

-continued

| | | | | | | | | | | | | |
|---|---|---|---|---|---|---|---|---|---|---|---|---|
| gag | ggg | gaa | tct | gac | ctc | gac | gag | ctc | gag | gaa | gat | atg | gag | cag | 3254 |
| Glu | Gly | Glu | Ser | Asp | Leu | Asp | Glu | Leu | Glu | Glu | Asp | Met | Glu | Gln | |
| | 1005 | | | | 1010 | | | | | 1015 | | | | | |

| gct | tcg | cag | agc | tcc | tgg | cag | gaa | gag | gac | ccc | aag | gga | cag | cag | 3299 |
| Ala | Ser | Gln | Ser | Ser | Trp | Gln | Glu | Glu | Asp | Pro | Lys | Gly | Gln | Gln | |
| 1020 | | | | | 1025 | | | | | 1030 | | | | | |

| gag | cag | ttg | cca | caa | gtc | caa | aag | tgt | gaa | aac | cac | cag | gca | gcc | 3344 |
| Glu | Gln | Leu | Pro | Gln | Val | Gln | Lys | Cys | Glu | Asn | His | Gln | Ala | Ala | |
| 1035 | | | | | 1040 | | | | | 1045 | | | | | |

| aga | agc | cca | gcc | tcc | atg | atg | tcc | tct | gag | gac | ctg | gct | cca | tac | 3389 |
| Arg | Ser | Pro | Ala | Ser | Met | Met | Ser | Ser | Glu | Asp | Leu | Ala | Pro | Tyr | |
| 1050 | | | | | 1055 | | | | | 1060 | | | | | |

| ctg | ggt | gag | agc | tgg | aag | agg | aag | gat | agc | cct | cag | gtc | cct | gcc | 3434 |
| Leu | Gly | Glu | Ser | Trp | Lys | Arg | Lys | Asp | Ser | Pro | Gln | Val | Pro | Ala | |
| 1065 | | | | | 1070 | | | | | 1075 | | | | | |

| gag | gga | gtg | gat | gac | acg | agc | tcc | tct | gag | ggc | agc | acg | gtg | gac | 3479 |
| Glu | Gly | Val | Asp | Asp | Thr | Ser | Ser | Ser | Glu | Gly | Ser | Thr | Val | Asp | |
| 1080 | | | | | 1085 | | | | | 1090 | | | | | |

| tgc | ccg | gac | cca | gag | gaa | atc | ctg | agg | aag | atc | ccc | gag | ctg | gca | 3524 |
| Cys | Pro | Asp | Pro | Glu | Glu | Ile | Leu | Arg | Lys | Ile | Pro | Glu | Leu | Ala | |
| 1095 | | | | | 1100 | | | | | 1105 | | | | | |

| gat | gac | ctg | gac | gag | ccc | gat | gac | tgt | ttc | aca | gaa | ggc | tgc | act | 3569 |
| Asp | Asp | Leu | Asp | Glu | Pro | Asp | Asp | Cys | Phe | Thr | Glu | Gly | Cys | Thr | |
| 1110 | | | | | 1115 | | | | | 1120 | | | | | |

| cgc | cgc | tgt | ccc | tgc | tgc | aac | gtg | aat | act | agc | aag | tct | cct | tgg | 3614 |
| Arg | Arg | Cys | Pro | Cys | Cys | Asn | Val | Asn | Thr | Ser | Lys | Ser | Pro | Trp | |
| 1125 | | | | | 1130 | | | | | 1135 | | | | | |

| gcc | aca | ggc | tgg | cag | gtg | cgc | aag | acc | tgc | tac | cgc | atc | gtg | gag | 3659 |
| Ala | Thr | Gly | Trp | Gln | Val | Arg | Lys | Thr | Cys | Tyr | Arg | Ile | Val | Glu | |
| 1140 | | | | | 1145 | | | | | 1150 | | | | | |

| cac | agc | tgg | ttt | gag | agt | ttc | atc | atc | ttc | atg | atc | ctg | ctc | agc | 3704 |
| His | Ser | Trp | Phe | Glu | Ser | Phe | Ile | Ile | Phe | Met | Ile | Leu | Leu | Ser | |
| 1155 | | | | | 1160 | | | | | 1165 | | | | | |

| agt | gga | gcg | ctg | gcc | ttt | gag | gat | aac | tac | ctg | gaa | gag | aaa | ccc | 3749 |
| Ser | Gly | Ala | Leu | Ala | Phe | Glu | Asp | Asn | Tyr | Leu | Glu | Glu | Lys | Pro | |
| 1170 | | | | | 1175 | | | | | 1180 | | | | | |

| cga | gtg | aag | tcc | gtg | ctg | gag | tac | act | gac | cga | gtg | ttc | acc | ttc | 3794 |
| Arg | Val | Lys | Ser | Val | Leu | Glu | Tyr | Thr | Asp | Arg | Val | Phe | Thr | Phe | |
| 1185 | | | | | 1190 | | | | | 1195 | | | | | |

| atc | ttc | gtc | ttt | gag | atg | ctg | ctc | aag | tgg | gta | gcc | tat | ggc | ttc | 3839 |
| Ile | Phe | Val | Phe | Glu | Met | Leu | Leu | Lys | Trp | Val | Ala | Tyr | Gly | Phe | |
| 1200 | | | | | 1205 | | | | | 1210 | | | | | |

| aaa | aag | tat | ttc | acc | aat | gcc | tgg | tgc | tgg | ctg | gac | ttc | ctc | att | 3884 |
| Lys | Lys | Tyr | Phe | Thr | Asn | Ala | Trp | Cys | Trp | Leu | Asp | Phe | Leu | Ile | |
| 1215 | | | | | 1220 | | | | | 1225 | | | | | |

| gtg | aac | atc | tcc | ctg | aca | agc | ctc | ata | gcg | aag | atc | ctt | gag | tat | 3929 |
| Val | Asn | Ile | Ser | Leu | Thr | Ser | Leu | Ile | Ala | Lys | Ile | Leu | Glu | Tyr | |
| 1230 | | | | | 1235 | | | | | 1240 | | | | | |

| tcc | gac | gtg | gcg | tcc | atc | aaa | gcc | ctt | cgg | act | ctc | cgt | gcc | ctc | 3974 |
| Ser | Asp | Val | Ala | Ser | Ile | Lys | Ala | Leu | Arg | Thr | Leu | Arg | Ala | Leu | |
| 1245 | | | | | 1250 | | | | | 1255 | | | | | |

| cga | ccg | ctg | cgg | gct | ctg | tct | cga | ttc | gaa | ggc | atg | agg | gta | gtg | 4019 |
| Arg | Pro | Leu | Arg | Ala | Leu | Ser | Arg | Phe | Glu | Gly | Met | Arg | Val | Val | |
| 1260 | | | | | 1265 | | | | | 1270 | | | | | |

| gtg | gat | gcc | ctc | gtg | ggc | gcc | atc | ccc | tcc | atc | atg | aac | gtc | ctc | 4064 |
| Val | Asp | Ala | Leu | Val | Gly | Ala | Ile | Pro | Ser | Ile | Met | Asn | Val | Leu | |
| 1275 | | | | | 1280 | | | | | 1285 | | | | | |

| ctc | gtc | tgc | ctc | atc | ttc | tgg | ctc | atc | ttc | agc | atc | atg | ggc | gtg | 4109 |
| Leu | Val | Cys | Leu | Ile | Phe | Trp | Leu | Ile | Phe | Ser | Ile | Met | Gly | Val | |
| 1290 | | | | | 1295 | | | | | 1300 | | | | | |

-continued

| | | |
|---|---|---|
| aac ctc ttc gcc ggg aaa ttt tcg aag tgc gtc gac acc aga aat<br>Asn Leu Phe Ala Gly Lys Phe Ser Lys Cys Val Asp Thr Arg Asn<br>1305                         1310                     1315 | 4154 | |
| aac cca ttt tcc aac gtg aat tcg acg atg gtg aat aac aag tcc<br>Asn Pro Phe Ser Asn Val Asn Ser Thr Met Val Asn Asn Lys Ser<br>1320                       1325                     1330 | 4199 | |
| gag tgt cac aat caa aac agc acc ggc cac ttc ttc tgg gtc aac<br>Glu Cys His Asn Gln Asn Ser Thr Gly His Phe Phe Trp Val Asn<br>1335                       1340                     1345 | 4244 | |
| gtc aaa gtc aac ttc gac aac gtc gct atg ggc tac ctc gca ctt<br>Val Lys Val Asn Phe Asp Asn Val Ala Met Gly Tyr Leu Ala Leu<br>1350                       1355                     1360 | 4289 | |
| ctt cag gtg gca acc ttc aaa ggc tgg atg gac ata atg tat gca<br>Leu Gln Val Ala Thr Phe Lys Gly Trp Met Asp Ile Met Tyr Ala<br>1365                       1370                     1375 | 4334 | |
| gct gtt gat tcc gga gag atc aac agt cag cct aac tgg gag aac<br>Ala Val Asp Ser Gly Glu Ile Asn Ser Gln Pro Asn Trp Glu Asn<br>1380                       1385                     1390 | 4379 | |
| aac ttg tac atg tac ctg tac ttc gtc gtt ttc atc att ttc ggt<br>Asn Leu Tyr Met Tyr Leu Tyr Phe Val Val Phe Ile Ile Phe Gly<br>1395                       1400                     1405 | 4424 | |
| ggc ttc ttc acg ctg aat ctc ttt gtt ggg gtc ata atc gac aac<br>Gly Phe Phe Thr Leu Asn Leu Phe Val Gly Val Ile Ile Asp Asn<br>1410                       1415                     1420 | 4469 | |
| ttc aac caa cag aaa aaa aag cta gga ggc cag gac atc ttc atg<br>Phe Asn Gln Gln Lys Lys Lys Leu Gly Gly Gln Asp Ile Phe Met<br>1425                       1430                     1435 | 4514 | |
| aca gaa gag cag aag aag tac tac aat gcc atg aag aag ctg ggc<br>Thr Glu Glu Gln Lys Lys Tyr Tyr Asn Ala Met Lys Lys Leu Gly<br>1440                       1445                     1450 | 4559 | |
| tcc aag aaa ccc cag aag ccc atc cca cgg ccc ctg aat aag tac<br>Ser Lys Lys Pro Gln Lys Pro Ile Pro Arg Pro Leu Asn Lys Tyr<br>1455                       1460                     1465 | 4604 | |
| caa ggc ttc gtg ttt gac atc gtg acc agg caa gcc ttt gac atc<br>Gln Gly Phe Val Phe Asp Ile Val Thr Arg Gln Ala Phe Asp Ile<br>1470                       1475                     1480 | 4649 | |
| atc atc atg gtt ctc atc tgc ctc aac atg atc acc atg atg gtg<br>Ile Ile Met Val Leu Ile Cys Leu Asn Met Ile Thr Met Met Val<br>1485                       1490                     1495 | 4694 | |
| gag acc gac gag cag ggc gag gag aag acg aag gtt ctg ggc aga<br>Glu Thr Asp Glu Gln Gly Glu Glu Lys Thr Lys Val Leu Gly Arg<br>1500                       1505                     1510 | 4739 | |
| atc aac cag ttc ttt gtg gcc gtc ttc acg ggc gag tgt gtg atg<br>Ile Asn Gln Phe Phe Val Ala Val Phe Thr Gly Glu Cys Val Met<br>1515                       1520                     1525 | 4784 | |
| aag atg ttc gcc ctg cga cag tac tac ttc acc aac ggc tgg aac<br>Lys Met Phe Ala Leu Arg Gln Tyr Tyr Phe Thr Asn Gly Trp Asn<br>1530                       1535                     1540 | 4829 | |
| gtg ttc gac ttc ata gtg gtg atc ctg tcc att ggg agt ctg ctg<br>Val Phe Asp Phe Ile Val Val Ile Leu Ser Ile Gly Ser Leu Leu<br>1545                       1550                     1555 | 4874 | |
| ttt tct gca atc ctt aag tca ctg gaa aac tac ttc tcc ccg acg<br>Phe Ser Ala Ile Leu Lys Ser Leu Glu Asn Tyr Phe Ser Pro Thr<br>1560                       1565                     1570 | 4919 | |
| ctc ttc cgg gtc atc cgt ctg gcc agg atc ggc cgc atc ctc agg<br>Leu Phe Arg Val Ile Arg Leu Ala Arg Ile Gly Arg Ile Leu Arg<br>1575                       1580                     1585 | 4964 | |
| ctg atc cga gca gcc aag ggg att cgc acg ctg ctc ttc gcc ctc<br>Leu Ile Arg Ala Ala Lys Gly Ile Arg Thr Leu Leu Phe Ala Leu | 5009 | |

-continued

|                                                                                                    |      |
|----------------------------------------------------------------------------------------------------|------|
| 1590                        1595                        1600                                      |      |
| atg atg tcc ctg ccc gcc ctc ttc aac atc ggc ctc ctc ctc ttc                                        | 5054 |
| Met Met Ser Leu Pro Ala Leu Phe Asn Ile Gly Leu Leu Leu Phe                                        |      |
|     1605                        1610                        1615                                  |      |
| ctc gtc atg ttc atc tac tcc atc ttc ggc atg gcc agc ttc gct                                        | 5099 |
| Leu Val Met Phe Ile Tyr Ser Ile Phe Gly Met Ala Ser Phe Ala                                        |      |
|     1620                        1625                        1630                                  |      |
| aac gtc gtg gac gag gcc ggc atc gac gac atg ttc aac ttc aag                                        | 5144 |
| Asn Val Val Asp Glu Ala Gly Ile Asp Asp Met Phe Asn Phe Lys                                        |      |
|     1635                        1640                        1645                                  |      |
| acc ttt ggc aac agc atg ctg tgc ctg ttc cag atc acc acc tcg                                        | 5189 |
| Thr Phe Gly Asn Ser Met Leu Cys Leu Phe Gln Ile Thr Thr Ser                                        |      |
|     1650                        1655                        1660                                  |      |
| gcc ggc tgg gac ggc ctc ctc agc ccc atc ctc aac acg ggg cct                                        | 5234 |
| Ala Gly Trp Asp Gly Leu Leu Ser Pro Ile Leu Asn Thr Gly Pro                                        |      |
|     1665                        1670                        1675                                  |      |
| ccc tac tgc gac ccc aac ctg ccc aac agc aac ggc tcc cgg ggg                                        | 5279 |
| Pro Tyr Cys Asp Pro Asn Leu Pro Asn Ser Asn Gly Ser Arg Gly                                        |      |
|     1680                        1685                        1690                                  |      |
| aac tgc ggg agc ccg gcg gtg ggc atc atc ttc ttc acc acc tac                                        | 5324 |
| Asn Cys Gly Ser Pro Ala Val Gly Ile Ile Phe Phe Thr Thr Tyr                                        |      |
|     1695                        1700                        1705                                  |      |
| atc atc atc tcc ttc ctc atc gtg gtc aac atg tac atc gca gtg                                        | 5369 |
| Ile Ile Ile Ser Phe Leu Ile Val Val Asn Met Tyr Ile Ala Val                                        |      |
|     1710                        1715                        1720                                  |      |
| att ctg gag aac ttc aac gta gcc acc gag gag agc acg gag ccc                                        | 5414 |
| Ile Leu Glu Asn Phe Asn Val Ala Thr Glu Glu Ser Thr Glu Pro                                        |      |
|     1725                        1730                        1735                                  |      |
| ctg agc gag gac gac ttc gac atg ttc tat gag acc tgg gag aag                                        | 5459 |
| Leu Ser Glu Asp Asp Phe Asp Met Phe Tyr Glu Thr Trp Glu Lys                                        |      |
|     1740                        1745                        1750                                  |      |
| ttc gac ccg gag gcc acc cag ttc att gcc ttt tct gcc ctc tca                                        | 5504 |
| Phe Asp Pro Glu Ala Thr Gln Phe Ile Ala Phe Ser Ala Leu Ser                                        |      |
|     1755                        1760                        1765                                  |      |
| gac ttc gcg gac acg ctc tcc ggc cct ctt aga atc ccc aaa ccc                                        | 5549 |
| Asp Phe Ala Asp Thr Leu Ser Gly Pro Leu Arg Ile Pro Lys Pro                                        |      |
|     1770                        1775                        1780                                  |      |
| aac cag aat ata tta atc cag atg gac ctg ccg ttg gtc ccc ggg                                        | 5594 |
| Asn Gln Asn Ile Leu Ile Gln Met Asp Leu Pro Leu Val Pro Gly                                        |      |
|     1785                        1790                        1795                                  |      |
| gat aag atc cac tgt ctg gac atc ctt ttt gcc ttc aca aag aac                                        | 5639 |
| Asp Lys Ile His Cys Leu Asp Ile Leu Phe Ala Phe Thr Lys Asn                                        |      |
|     1800                        1805                        1810                                  |      |
| gtc ttg gga gaa tcc ggg gag ttg gac tcc ctg aag acc aat atg                                        | 5684 |
| Val Leu Gly Glu Ser Gly Glu Leu Asp Ser Leu Lys Thr Asn Met                                        |      |
|     1815                        1820                        1825                                  |      |
| gaa gag aag ttt atg gcg acc aat ctc tcc aaa gca tcc tat gaa                                        | 5729 |
| Glu Glu Lys Phe Met Ala Thr Asn Leu Ser Lys Ala Ser Tyr Glu                                        |      |
|     1830                        1835                        1840                                  |      |
| cca ata gcc acc acc ctc cgg tgg aag cag gaa gac ctc tca gcc                                        | 5774 |
| Pro Ile Ala Thr Thr Leu Arg Trp Lys Gln Glu Asp Leu Ser Ala                                        |      |
|     1845                        1850                        1855                                  |      |
| aca gtc att caa aag gcc tac cgg agc tac atg ctg cac cgc tcc                                        | 5819 |
| Thr Val Ile Gln Lys Ala Tyr Arg Ser Tyr Met Leu His Arg Ser                                        |      |
|     1860                        1865                        1870                                  |      |
| ttg aca ctc tcc aac acc ctg cat gtg ccc agg gct gag gag gat                                        | 5864 |
| Leu Thr Leu Ser Asn Thr Leu His Val Pro Arg Ala Glu Glu Asp                                        |      |
|     1875                        1880                        1885                                  |      |
| ggc gtg tca ctt ccc ggg gaa ggc tac att aca ttc atg gca aac                                        | 5909 |

-continued

```
Gly Val Ser Leu Pro Gly Glu Gly Tyr Ile Thr Phe Met Ala Asn
        1890                1895                1900 agt gga ctc ccg gac aaa tca gaa act gcc tct gct acg tct ttc         5954
Ser Gly Leu Pro Asp Lys Ser Glu Thr Ala Ser Ala Thr Ser Phe
        1905                1910                1915 ccg cca tcc tat gac agt gtc acc agg ggc ctg agt gac cgg gcc         5999
Pro Pro Ser Tyr Asp Ser Val Thr Arg Gly Leu Ser Asp Arg Ala
        1920                1925                1930 aac att aac cca tct agc tca atg caa aat gaa gat gag gtc gct         6044
Asn Ile Asn Pro Ser Ser Ser Met Gln Asn Glu Asp Glu Val Ala
        1935                1940                1945 gct aag gaa gga aac agc cct gga cct cag tgaaggcact caggcatgca       6094
Ala Lys Glu Gly Asn Ser Pro Gly Pro Gln
        1950                1955 cagggcaggt tccaatgtct ttctctgctg tactaactcc ttccctctgg aggtggcacc   6154
aacctccagc ctccaccaat gcatgtcact ggtcatggtg tcagaactga atggggacat   6214
ccttgagaaa gccccaccc caataggaat caaaagccaa ggatactcct ccattctgac    6274
gtcccttccg agttcccaga agatgtcatt gctcccttct gtttgtgacc agagacgtga   6334
ttcaccaact tctcggagcc agagacacat agcaaagact tttctgctgg tgtcgggcag   6394
tcttagagaa gtcacgtagg ggttggtact gagaattagg gtttgcatga ctgcatgctc   6454
acagctgccg gacaatacct gtgagtcggc cattaaaatt aatattttta aagttaaaaa   6514
aaaaaaaaaa                                                          6524

<210> SEQ ID NO 2
<211> LENGTH: 1957
<212> TYPE: PRT
<213> ORGANISM: Rattus norvegicus

<400> SEQUENCE: 2

Met Glu Leu Pro Phe Ala Ser Val Gly Thr Thr Asn Phe Arg Arg Phe
1               5                   10                  15

Thr Pro Glu Ser Leu Ala Glu Ile Glu Lys Gln Ile Ala Ala His Arg
            20                  25                  30

Ala Ala Lys Lys Ala Arg Thr Lys His Arg Gly Gln Glu Asp Lys Gly
        35                  40                  45

Glu Lys Pro Arg Pro Gln Leu Asp Leu Lys Asp Cys Asn Gln Leu Pro
    50                  55                  60

Lys Phe Tyr Gly Glu Leu Pro Ala Glu Leu Val Gly Glu Pro Leu Glu
65                  70                  75                  80

Asp Leu Asp Pro Phe Tyr Ser Thr His Arg Thr Phe Met Val Leu Asn
                85                  90                  95

Lys Ser Arg Thr Ile Ser Arg Phe Ser Ala Thr Trp Ala Leu Trp Leu
            100                 105                 110

Phe Ser Pro Phe Asn Leu Ile Arg Arg Thr Ala Ile Lys Val Ser Val
        115                 120                 125

His Ser Trp Phe Ser Ile Phe Ile Thr Ile Thr Ile Leu Val Asn Cys
    130                 135                 140

Val Cys Met Thr Arg Thr Asp Leu Pro Glu Lys Val Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
            180                 185                 190
```

-continued

```
Asp Phe Ser Val Ile Thr Leu Ala Tyr Val Gly Ala Ala Ile Asp Leu
    195                 200                 205

Arg Gly Ile Ser Gly Leu Arg Thr Phe Arg Val Leu Arg Ala Leu Lys
    210                 215                 220

Thr Val Ser Val Ile Pro Gly Leu Lys Val Ile Val Gly Ala Leu Ile
225                 230                 235                 240

His Ser Val Arg Lys Leu Ala Asp Val Thr Ile Leu Thr Val Phe Cys
                245                 250                 255

Leu Ser Val Phe Ala Leu Val Gly Leu Gln Leu Phe Lys Gly Asn Leu
                260                 265                 270

Lys Asn Lys Cys Ile Arg Asn Gly Thr Asp Pro His Lys Ala Asp Asn
            275                 280                 285

Leu Ser Ser Glu Met Ala Glu Tyr Ile Phe Ile Lys Pro Gly Thr Thr
    290                 295                 300

Asp Pro Leu Leu Cys Gly Asn Gly Ser Asp Ala Gly His Cys Pro Gly
305                 310                 315                 320

Gly Tyr Val Cys Leu Lys Thr Pro Asp Asn Pro Asp Phe Asn Tyr Thr
                325                 330                 335

Ser Phe Asp Ser Phe Ala Trp Ala Phe Leu Ser Leu Phe Arg Leu Met
                340                 345                 350

Thr Gln Asp Ser Trp Glu Arg Leu Tyr Gln Gln Thr Leu Arg Ala Ser
            355                 360                 365

Gly Lys Met Tyr Met Val Phe Phe Val Leu Val Ile Phe Leu Gly Ser
    370                 375                 380

Phe Tyr Leu Val Asn Leu Ile Leu Ala Val Val Thr Met Ala Tyr Glu
385                 390                 395                 400

Glu Gln Ser Gln Ala Thr Ile Ala Glu Ile Glu Ala Lys Glu Lys Lys
                405                 410                 415

Phe Gln Glu Ala Leu Glu Val Leu Gln Lys Glu Gln Glu Val Leu Glu
            420                 425                 430

Ala Leu Gly Ile Asp Thr Thr Ser Leu Gln Ser His Ser Gly Ser Pro
    435                 440                 445

Leu Ala Ser Lys Asn Ala Asn Glu Arg Arg Pro Arg Val Lys Ser Arg
    450                 455                 460

Val Ser Glu Gly Ser Thr Asp Asp Asn Arg Ser Pro Gln Ser Asp Pro
465                 470                 475                 480

Tyr Asn Gln Arg Arg Met Ser Phe Leu Gly Leu Ser Ser Gly Arg Arg
                485                 490                 495

Arg Ala Ser His Gly Ser Val Phe His Phe Arg Ala Pro Ser Gln Asp
                500                 505                 510

Ile Ser Phe Pro Asp Gly Ile Thr Pro Asp Asp Gly Val Phe His Gly
            515                 520                 525

Asp Gln Glu Ser Arg Arg Gly Ser Ile Leu Leu Gly Arg Gly Ala Gly
    530                 535                 540

Gln Thr Gly Pro Leu Pro Arg Ser Pro Leu Pro Gln Ser Pro Asn Pro
545                 550                 555                 560

Gly Arg Arg His Gly Glu Glu Gly Gln Leu Gly Val Pro Thr Gly Glu
                565                 570                 575

Leu Thr Ala Gly Ala Pro Glu Gly Pro Ala Leu His Thr Thr Gly Gln
                580                 585                 590

Lys Ser Phe Leu Ser Ala Gly Tyr Leu Asn Glu Pro Phe Arg Ala Gln
            595                 600                 605

Arg Ala Met Ser Val Val Ser Ile Met Thr Ser Val Ile Glu Glu Leu
```

-continued

```
            610                 615                 620
Glu Glu Ser Lys Leu Lys Cys Pro Pro Cys Leu Ile Ser Phe Ala Gln
625                 630                 635                 640

Lys Tyr Leu Ile Trp Glu Cys Cys Pro Lys Trp Arg Lys Phe Lys Met
                    645                 650                 655

Ala Leu Phe Glu Leu Val Thr Asp Pro Phe Ala Glu Leu Thr Ile Thr
                660                 665                 670

Leu Cys Ile Val Val Asn Thr Val Phe Met Ala Met Glu His Tyr Pro
            675                 680                 685

Met Thr Asp Ala Phe Asp Ala Met Leu Gln Ala Gly Asn Ile Val Phe
690                 695                 700

Thr Val Phe Phe Thr Met Glu Met Ala Phe Lys Ile Ile Ala Phe Asp
705                 710                 715                 720

Pro Tyr Tyr Tyr Phe Gln Lys Lys Trp Asn Ile Phe Asp Cys Val Ile
                725                 730                 735

Val Thr Val Ser Leu Leu Glu Leu Ser Ala Ser Lys Lys Gly Ser Leu
                740                 745                 750

Ser Val Leu Arg Thr Leu Arg Leu Leu Arg Val Phe Lys Leu Ala Lys
            755                 760                 765

Ser Trp Pro Thr Leu Asn Thr Leu Ile Lys Ile Ile Gly Asn Ser Val
770                 775                 780

Gly Ala Leu Gly Asn Leu Thr Phe Ile Leu Ala Ile Ile Val Phe Ile
785                 790                 795                 800

Phe Ala Leu Val Gly Lys Gln Leu Leu Ser Glu Asp Tyr Gly Cys Arg
                805                 810                 815

Lys Asp Gly Val Ser Val Trp Asn Gly Glu Lys Leu Arg Trp His Met
                820                 825                 830

Cys Asp Phe Phe His Ser Phe Leu Val Val Phe Arg Ile Leu Cys Gly
            835                 840                 845

Glu Trp Ile Glu Asn Met Trp Val Cys Met Glu Val Ser Gln Lys Ser
850                 855                 860

Ile Cys Leu Ile Leu Phe Leu Thr Val Met Val Leu Gly Asn Leu Val
865                 870                 875                 880

Val Leu Asn Leu Phe Ile Ala Leu Leu Leu Asn Ser Phe Ser Ala Asp
                885                 890                 895

Asn Leu Thr Ala Pro Glu Asp Asp Gly Glu Val Asn Asn Leu Gln Leu
                900                 905                 910

Ala Leu Ala Arg Ile Gln Val Leu Gly His Arg Ala Ser Arg Ala Ile
            915                 920                 925

Ala Ser Tyr Ile Ser Ser His Cys Arg Phe His Trp Pro Lys Val Glu
930                 935                 940

Thr Gln Leu Gly Met Lys Pro Pro Leu Thr Ser Ser Glu Ala Lys Asn
945                 950                 955                 960

His Ile Ala Thr Asp Ala Val Ser Ala Ala Val Gly Asn Leu Thr Lys
                965                 970                 975

Pro Ala Leu Ser Ser Pro Lys Glu Asn His Gly Asp Phe Ile Thr Asp
                980                 985                 990

Pro Asn Val Trp Val Ser Val Pro  Ile Ala Glu Gly Glu  Ser Asp Leu
                995                 1000                1005

Asp Glu  Leu Glu Glu Asp Met  Glu Gln Ala Ser Gln  Ser Ser Trp
        1010                1015                1020

Gln Glu  Glu Asp Pro Lys Gly  Gln Gln Glu Gln Leu  Pro Gln Val
        1025                1030                1035
```

```
Gln Lys Cys Glu Asn His Gln Ala Ala Arg Ser Pro Ala Ser Met
    1040                1045                1050

Met Ser Ser Glu Asp Leu Ala Pro Tyr Leu Gly Glu Ser Trp Lys
    1055                1060                1065

Arg Lys Asp Ser Pro Gln Val Pro Ala Glu Gly Val Asp Asp Thr
    1070                1075                1080

Ser Ser Ser Glu Gly Ser Thr Val Asp Cys Pro Asp Pro Glu Glu
    1085                1090                1095

Ile Leu Arg Lys Ile Pro Glu Leu Ala Asp Asp Leu Asp Glu Pro
    1100                1105                1110

Asp Asp Cys Phe Thr Glu Gly Cys Thr Arg Arg Cys Pro Cys Cys
    1115                1120                1125

Asn Val Asn Thr Ser Lys Ser Pro Trp Ala Thr Gly Trp Gln Val
    1130                1135                1140

Arg Lys Thr Cys Tyr Arg Ile Val Glu His Ser Trp Phe Glu Ser
    1145                1150                1155

Phe Ile Ile Phe Met Ile Leu Leu Ser Ser Gly Ala Leu Ala Phe
    1160                1165                1170

Glu Asp Asn Tyr Leu Glu Glu Lys Pro Arg Val Lys Ser Val Leu
    1175                1180                1185

Glu Tyr Thr Asp Arg Val Phe Thr Phe Ile Phe Val Phe Glu Met
    1190                1195                1200

Leu Leu Lys Trp Val Ala Tyr Gly Phe Lys Lys Tyr Phe Thr Asn
    1205                1210                1215

Ala Trp Cys Trp Leu Asp Phe Leu Ile Val Asn Ile Ser Leu Thr
    1220                1225                1230

Ser Leu Ile Ala Lys Ile Leu Glu Tyr Ser Asp Val Ala Ser Ile
    1235                1240                1245

Lys Ala Leu Arg Thr Leu Arg Ala Leu Arg Pro Leu Arg Ala Leu
    1250                1255                1260

Ser Arg Phe Glu Gly Met Arg Val Val Val Asp Ala Leu Val Gly
    1265                1270                1275

Ala Ile Pro Ser Ile Met Asn Val Leu Leu Val Cys Leu Ile Phe
    1280                1285                1290

Trp Leu Ile Phe Ser Ile Met Gly Val Asn Leu Phe Ala Gly Lys
    1295                1300                1305

Phe Ser Lys Cys Val Asp Thr Arg Asn Asn Pro Phe Ser Asn Val
    1310                1315                1320

Asn Ser Thr Met Val Asn Asn Lys Ser Glu Cys His Asn Gln Asn
    1325                1330                1335

Ser Thr Gly His Phe Phe Trp Val Asn Val Lys Val Asn Phe Asp
    1340                1345                1350

Asn Val Ala Met Gly Tyr Leu Ala Leu Leu Gln Val Ala Thr Phe
    1355                1360                1365

Lys Gly Trp Met Asp Ile Met Tyr Ala Ala Val Asp Ser Gly Glu
    1370                1375                1380

Ile Asn Ser Gln Pro Asn Trp Glu Asn Asn Leu Tyr Met Tyr Leu
    1385                1390                1395

Tyr Phe Val Val Phe Ile Ile Phe Gly Gly Phe Phe Thr Leu Asn
    1400                1405                1410

Leu Phe Val Gly Val Ile Ile Asp Asn Phe Asn Gln Gln Lys Lys
    1415                1420                1425
```

-continued

```
Lys Leu Gly Gly Gln Asp Ile Phe Met Thr Glu Glu Gln Lys Lys
    1430                1435                1440

Tyr Tyr Asn Ala Met Lys Lys Leu Gly Ser Lys Lys Pro Gln Lys
    1445                1450                1455

Pro Ile Pro Arg Pro Leu Asn Lys Tyr Gln Gly Phe Val Phe Asp
    1460                1465                1470

Ile Val Thr Arg Gln Ala Phe Asp Ile Ile Met Val Leu Ile
    1475                1480                1485

Cys Leu Asn Met Ile Thr Met Met Val Glu Thr Asp Glu Gln Gly
    1490                1495                1500

Glu Glu Lys Thr Lys Val Leu Gly Arg Ile Asn Gln Phe Phe Val
    1505                1510                1515

Ala Val Phe Thr Gly Glu Cys Val Met Lys Met Phe Ala Leu Arg
    1520                1525                1530

Gln Tyr Tyr Phe Thr Asn Gly Trp Asn Val Phe Asp Phe Ile Val
    1535                1540                1545

Val Ile Leu Ser Ile Gly Ser Leu Leu Phe Ser Ala Ile Leu Lys
    1550                1555                1560

Ser Leu Glu Asn Tyr Phe Ser Pro Thr Leu Phe Arg Val Ile Arg
    1565                1570                1575

Leu Ala Arg Ile Gly Arg Ile Leu Arg Leu Ile Arg Ala Ala Lys
    1580                1585                1590

Gly Ile Arg Thr Leu Leu Phe Ala Leu Met Met Ser Leu Pro Ala
    1595                1600                1605

Leu Phe Asn Ile Gly Leu Leu Leu Phe Leu Val Met Phe Ile Tyr
    1610                1615                1620

Ser Ile Phe Gly Met Ala Ser Phe Ala Asn Val Val Asp Glu Ala
    1625                1630                1635

Gly Ile Asp Asp Met Phe Asn Phe Lys Thr Phe Gly Asn Ser Met
    1640                1645                1650

Leu Cys Leu Phe Gln Ile Thr Thr Ser Ala Gly Trp Asp Gly Leu
    1655                1660                1665

Leu Ser Pro Ile Leu Asn Thr Gly Pro Pro Tyr Cys Asp Pro Asn
    1670                1675                1680

Leu Pro Asn Ser Asn Gly Ser Arg Gly Asn Cys Gly Ser Pro Ala
    1685                1690                1695

Val Gly Ile Ile Phe Phe Thr Thr Tyr Ile Ile Ile Ser Phe Leu
    1700                1705                1710

Ile Val Val Asn Met Tyr Ile Ala Val Ile Leu Glu Asn Phe Asn
    1715                1720                1725

Val Ala Thr Glu Glu Ser Thr Glu Pro Leu Ser Glu Asp Asp Phe
    1730                1735                1740

Asp Met Phe Tyr Glu Thr Trp Glu Lys Phe Asp Pro Glu Ala Thr
    1745                1750                1755

Gln Phe Ile Ala Phe Ser Ala Leu Ser Asp Phe Ala Asp Thr Leu
    1760                1765                1770

Ser Gly Pro Leu Arg Ile Pro Lys Pro Asn Gln Asn Ile Leu Ile
    1775                1780                1785

Gln Met Asp Leu Pro Leu Val Pro Gly Asp Lys Ile His Cys Leu
    1790                1795                1800

Asp Ile Leu Phe Ala Phe Thr Lys Asn Val Leu Gly Glu Ser Gly
    1805                1810                1815

Glu Leu Asp Ser Leu Lys Thr Asn Met Glu Glu Lys Phe Met Ala
```

```
                    1820                1825                 1830

Thr Asn  Leu Ser Lys Ala Ser  Tyr Glu Pro Ile Ala  Thr Thr Leu
        1835                1840                 1845

Arg Trp  Lys Gln Glu Asp Leu  Ser Ala Thr Val Ile  Gln Lys Ala
        1850                1855                 1860

Tyr Arg  Ser Tyr Met Leu His  Arg Ser Leu Thr Leu  Ser Asn Thr
        1865                1870                 1875

Leu His  Val Pro Arg Ala Glu  Glu Asp Gly Val Ser  Leu Pro Gly
        1880                1885                 1890

Glu Gly  Tyr Ile Thr Phe Met  Ala Asn Ser Gly Leu  Pro Asp Lys
        1895                1900                 1905

Ser Glu  Thr Ala Ser Ala Thr  Ser Phe Pro Pro Ser  Tyr Asp Ser
        1910                1915                 1920

Val Thr  Arg Gly Leu Ser Asp  Arg Ala Asn Ile Asn  Pro Ser Ser
        1925                1930                 1935

Ser Met  Gln Asn Glu Asp Glu  Val Ala Ala Lys Glu  Gly Asn Ser
        1940                1945                 1950

Pro Gly  Pro Gln
        1955

<210> SEQ ID NO 3
<211> LENGTH: 573
<212> TYPE: DNA
<213> ORGANISM: Rattus norvegicus
<220> FEATURE:
<221> NAME/KEY: CDS
<222> LOCATION: (46)..(333)
<223> OTHER INFORMATION:

<400> SEQUENCE: 3
aagactgcag cgcctcaggg cccaggtttc aacagattct tcaaa atg cca tcc caa      57
                                                  Met Pro Ser Gln
                                                   1 atg gag cat gcc atg gaa acc atg atg ctt aca ttt cac agg ttt gca      105
Met Glu His Ala Met Glu Thr Met Met Leu Thr Phe His Arg Phe Ala
  5              10                  15                  20 ggg gaa aaa aac tac ttg aca aag gag gac ctg aga gtg ctc atg gaa      153
Gly Glu Lys Asn Tyr Leu Thr Lys Glu Asp Leu Arg Val Leu Met Glu
             25                  30                  35 agg gag ttc cct ggg ttt ttg gaa aat caa aag gac cct ctg gct gtg      201
Arg Glu Phe Pro Gly Phe Leu Glu Asn Gln Lys Asp Pro Leu Ala Val
         40                  45                  50 gac aaa ata atg aaa gac ctg gac cag tgc cga gat gga aaa gtg ggc      249
Asp Lys Ile Met Lys Asp Leu Asp Gln Cys Arg Asp Gly Lys Val Gly
     55                  60                  65 ttc cag agc ttt cta tca cta gtg gcg ggg ctc atc att gca tgc aat      297
Phe Gln Ser Phe Leu Ser Leu Val Ala Gly Leu Ile Ile Ala Cys Asn
 70                  75                  80 gac tat ttt gta gta cac atg aag cag aag aag tag gccaactgga          343
Asp Tyr Phe Val Val His Met Lys Gln Lys Lys
85                  90                  95 gccctggtac ccacaccttg atgcgtcctc tcccatgggg tcaactgagg aatctgcccc      403
actgcttcct gtgagcagat caggacccct aggaaatgtg caaataacat ccaactccaa      463
ttcgacaagc agagaaagaa aagttaatcc aatgacagag gagctttcga gttttatatt      523
gtttgcatcc ggttgccctc aataaagaaa gtctttttt ttaagttccg              573

<210> SEQ ID NO 4
```

```
<211> LENGTH: 95
<212> TYPE: PRT
<213> ORGANISM: Rattus norvegicus

<400> SEQUENCE: 4

Met Pro Ser Gln Met Glu His Ala Met Glu Thr Met Met Leu Thr Phe
1               5                   10                  15

His Arg Phe Ala Gly Glu Lys Asn Tyr Leu Thr Lys Glu Asp Leu Arg
            20                  25                  30

Val Leu Met Glu Arg Glu Phe Pro Gly Phe Leu Glu Asn Gln Lys Asp
        35                  40                  45

Pro Leu Ala Val Asp Lys Ile Met Lys Asp Leu Gln Cys Arg Asp
    50                  55                  60

Gly Lys Val Gly Phe Gln Ser Phe Leu Ser Leu Val Ala Gly Leu Ile
65                  70                  75                  80

Ile Ala Cys Asn Asp Tyr Phe Val Val His Met Lys Gln Lys Lys
                85                  90                  95

<210> SEQ ID NO 5
<211> LENGTH: 5874
<212> TYPE: DNA
<213> ORGANISM: Homo sapiens
<220> FEATURE:
<221> NAME/KEY: CDS
<222> LOCATION: (1)..(5874)
<223> OTHER INFORMATION:

<400> SEQUENCE: 5
```

| | | | | | | | | | | | | | | | | |
|---|---|---|---|---|---|---|---|---|---|---|---|---|---|---|---|---|
| atg | gaa | ttc | ccc | att | gga | tcc | ctc | gaa | act | aac | aac | ttc | cgt | cgc | ttt | 48 |
| Met | Glu | Phe | Pro | Ile | Gly | Ser | Leu | Glu | Thr | Asn | Asn | Phe | Arg | Arg | Phe | |
| 1 | | | 5 | | | | | 10 | | | | | 15 | | | |
| act | ccg | gag | tca | ctg | gtg | gag | ata | gag | aag | caa | att | gct | gcc | aag | cag | 96 |
| Thr | Pro | Glu | Ser | Leu | Val | Glu | Ile | Glu | Lys | Gln | Ile | Ala | Ala | Lys | Gln | |
| | | | 20 | | | | 25 | | | | | 30 | | | | |
| gga | aca | aag | aaa | gcc | aga | gag | aag | cat | agg | gag | cag | aag | gac | caa | gaa | 144 |
| Gly | Thr | Lys | Lys | Ala | Arg | Glu | Lys | His | Arg | Glu | Gln | Lys | Asp | Gln | Glu | |
| | | 35 | | | | | 40 | | | | | 45 | | | | |
| gag | aag | cct | cgg | ccc | cag | ctg | gac | ttg | aaa | gcc | tgc | aac | cag | ctg | ccc | 192 |
| Glu | Lys | Pro | Arg | Pro | Gln | Leu | Asp | Leu | Lys | Ala | Cys | Asn | Gln | Leu | Pro | |
| | 50 | | | | | 55 | | | | | 60 | | | | | |
| aag | ttc | tat | ggt | gag | ctc | cca | gca | gaa | ctg | atc | ggg | gag | ccc | ctg | gag | 240 |
| Lys | Phe | Tyr | Gly | Glu | Leu | Pro | Ala | Glu | Leu | Ile | Gly | Glu | Pro | Leu | Glu | |
| 65 | | | | 70 | | | | | 75 | | | | | 80 | | |
| gat | cta | gat | ccg | ttc | tac | agc | aca | cac | cgg | aca | ttt | atg | gtg | ctg | aac | 288 |
| Asp | Leu | Asp | Pro | Phe | Tyr | Ser | Thr | His | Arg | Thr | Phe | Met | Val | Leu | Asn | |
| | | | | 85 | | | | | 90 | | | | | 95 | | |
| aaa | ggg | agg | acc | att | tcc | cgg | ttt | agt | gcc | act | cgg | gcc | ctg | tgg | cta | 336 |
| Lys | Gly | Arg | Thr | Ile | Ser | Arg | Phe | Ser | Ala | Thr | Arg | Ala | Leu | Trp | Leu | |
| | | | 100 | | | | | 105 | | | | | 110 | | | |
| ttc | agt | cct | ttc | aac | ctg | atc | aga | aga | acg | gcc | atc | aaa | gtg | tct | gtc | 384 |
| Phe | Ser | Pro | Phe | Asn | Leu | Ile | Arg | Arg | Thr | Ala | Ile | Lys | Val | Ser | Val | |
| | | | 115 | | | | | 120 | | | | | 125 | | | |
| cac | tcg | tgg | ttc | agt | tta | ttt | att | acg | gtc | act | att | ttg | gtt | aat | tgt | 432 |
| His | Ser | Trp | Phe | Ser | Leu | Phe | Ile | Thr | Val | Thr | Ile | Leu | Val | Asn | Cys | |
| | | 130 | | | | | 135 | | | | | 140 | | | | |
| gtg | tgc | atg | acc | cga | act | gac | ctt | cca | gag | aaa | att | gaa | tat | gtc | ttc | 480 |
| Val | Cys | Met | Thr | Arg | Thr | Asp | Leu | Pro | Glu | Lys | Ile | Glu | Tyr | Val | Phe | |
| 145 | | | | 150 | | | | | 155 | | | | | 160 | | |
| act | gtc | att | tac | acc | ttt | gaa | gcc | ttg | ata | aag | ata | ctg | gca | aga | gga | 528 |
| Thr | Val | Ile | Tyr | Thr | Phe | Glu | Ala | Leu | Ile | Lys | Ile | Leu | Ala | Arg | Gly | |
| | | | 165 | | | | | 170 | | | | | 175 | | | |

```
ttt tgt cta aat gag ttc acg tac ctg aga gat cct tgg aac tgg ctg      576
Phe Cys Leu Asn Glu Phe Thr Tyr Leu Arg Asp Pro Trp Asn Trp Leu
        180                 185                 190 gat ttt agc gtc att acc ctg gca tat gtt ggc aca gca ata gat ctc      624
Asp Phe Ser Val Ile Thr Leu Ala Tyr Val Gly Thr Ala Ile Asp Leu
        195                 200                 205 cgt ggg atc tca ggc ctg cgg aca ttc aga gtt ctt aga gca tta aaa      672
Arg Gly Ile Ser Gly Leu Arg Thr Phe Arg Val Leu Arg Ala Leu Lys
210                 215                 220 aca gtt tct gtg atc cca ggc ctg aag gtc att gtg ggg gcc ctg att      720
Thr Val Ser Val Ile Pro Gly Leu Lys Val Ile Val Gly Ala Leu Ile
225                 230                 235                 240 cac tca gtg aag aaa ctg gct gat gtg acc atc ctc acc atc ttc tgc      768
His Ser Val Lys Lys Leu Ala Asp Val Thr Ile Leu Thr Ile Phe Cys
                245                 250                 255 cta agt gtt ttt gcc ttg gtg ggg ctg caa ctc ttc aag ggc aac ctc      816
Leu Ser Val Phe Ala Leu Val Gly Leu Gln Leu Phe Lys Gly Asn Leu
            260                 265                 270 aaa aat aaa tgt gtc aag aat gac atg gct gtc aat gag aca acc aac      864
Lys Asn Lys Cys Val Lys Asn Asp Met Ala Val Asn Glu Thr Thr Asn
        275                 280                 285 tac tca tct cac aga aaa cca gat atc tac ata aat aag cga ggc act      912
Tyr Ser Ser His Arg Lys Pro Asp Ile Tyr Ile Asn Lys Arg Gly Thr
        290                 295                 300 tct gac ccc tta ctg tgt ggc aat gga tct gac tca ggc cac tgc cct      960
Ser Asp Pro Leu Leu Cys Gly Asn Gly Ser Asp Ser Gly His Cys Pro
305                 310                 315                 320 gat ggt tat atc tgc ctt aaa act tct gac aac ccg gat ttt aac tac     1008
Asp Gly Tyr Ile Cys Leu Lys Thr Ser Asp Asn Pro Asp Phe Asn Tyr
                325                 330                 335 acc agc ttt gat tcc ttt gct tgg gct ttc ctc tca ctg ttc cgc ctc     1056
Thr Ser Phe Asp Ser Phe Ala Trp Ala Phe Leu Ser Leu Phe Arg Leu
            340                 345                 350 atg aca cag gat tcc tgg gaa cgc ctc tac cag cag acc ctg agg act     1104
Met Thr Gln Asp Ser Trp Glu Arg Leu Tyr Gln Gln Thr Leu Arg Thr
        355                 360                 365 tct ggg aaa atc tat atg atc ttt ttt gtg ctc gta atc ttc ctg gga     1152
Ser Gly Lys Ile Tyr Met Ile Phe Phe Val Leu Val Ile Phe Leu Gly
        370                 375                 380 tct ttc tac ctg gtc aac ttg atc ttg gct gta gtc acc atg gcg tat     1200
Ser Phe Tyr Leu Val Asn Leu Ile Leu Ala Val Val Thr Met Ala Tyr
385                 390                 395                 400 gag gag cag aac cag gca acc act gat gaa att gaa gca aag gag aag     1248
Glu Glu Gln Asn Gln Ala Thr Thr Asp Glu Ile Glu Ala Lys Glu Lys
                405                 410                 415 aag ttc cag gag gcc ctc gag atg ctc cgg aag gag cag gag gtg cta     1296
Lys Phe Gln Glu Ala Leu Glu Met Leu Arg Lys Glu Gln Glu Val Leu
            420                 425                 430 gca gca cta ggg att gac aca acc tct ctc cac tcc cac aat gga tca     1344
Ala Ala Leu Gly Ile Asp Thr Thr Ser Leu His Ser His Asn Gly Ser
        435                 440                 445 cct tta acc tcc aaa aat gcc agt gag aga agg cat aga ata aag cca     1392
Pro Leu Thr Ser Lys Asn Ala Ser Glu Arg Arg His Arg Ile Lys Pro
450                 455                 460 aga gtg tca gag ggc tcc aca gaa gac aac aaa tca ccc cgc tct gat     1440
Arg Val Ser Glu Gly Ser Thr Glu Asp Asn Lys Ser Pro Arg Ser Asp
465                 470                 475                 480 cct tac aac cag cgc agg atg tct ttt cta ggc ctc gcc tct gga aaa     1488
Pro Tyr Asn Gln Arg Arg Met Ser Phe Leu Gly Leu Ala Ser Gly Lys
```

-continued

| | | 485 | | | | 490 | | | | 495 | | | |
|---|---|---|---|---|---|---|---|---|---|---|---|---|---|
| cgc | cgg | gct | agt | cat | ggc | agt | gtg | ttc | cat | ttc | cgg | tcc | cct | ggc | cga | 1536 |
| Arg | Arg | Ala | Ser | His | Gly | Ser | Val | Phe | His | Phe | Arg | Ser | Pro | Gly | Arg | |
| | | | 500 | | | | | 505 | | | | | 510 | | | |

| gat | atc | tca | ctc | cct | gag | gga | gtc | aca | gat | gat | gga | gtc | ttt | cct | gga | 1584 |
| Asp | Ile | Ser | Leu | Pro | Glu | Gly | Val | Thr | Asp | Asp | Gly | Val | Phe | Pro | Gly |
| | | | 515 | | | | | 520 | | | | | 525 | | |

| gac | cac | gaa | agc | cat | cgg | ggc | tct | ctg | ctg | ctg | ggt | ggg | ggt | gct | ggc | 1632 |
| Asp | His | Glu | Ser | His | Arg | Gly | Ser | Leu | Leu | Leu | Gly | Gly | Gly | Ala | Gly |
| | 530 | | | | | 535 | | | | | 540 | | | | |

| cag | caa | ggc | ccc | ctc | cct | aga | agc | cct | ctt | cct | caa | ccc | agc | aac | cct | 1680 |
| Gln | Gln | Gly | Pro | Leu | Pro | Arg | Ser | Pro | Leu | Pro | Gln | Pro | Ser | Asn | Pro |
| 545 | | | | | 550 | | | | | 555 | | | | | 560 |

| gac | tcc | agg | cat | gga | gaa | gat | gaa | cac | caa | ccg | ccg | ccc | act | agt | gag | 1728 |
| Asp | Ser | Arg | His | Gly | Glu | Asp | Glu | His | Gln | Pro | Pro | Pro | Thr | Ser | Glu |
| | | | | 565 | | | | | 570 | | | | | 575 | |

| ctt | gcc | cct | gga | gct | gtc | gat | gtc | tcg | gca | ttc | gat | gca | gga | caa | aag | 1776 |
| Leu | Ala | Pro | Gly | Ala | Val | Asp | Val | Ser | Ala | Phe | Asp | Ala | Gly | Gln | Lys |
| | | | 580 | | | | | 585 | | | | | 590 | | |

| aag | act | ttc | ttg | tca | gca | gaa | tac | tta | gat | gaa | cct | ttc | cgg | gcc | caa | 1824 |
| Lys | Thr | Phe | Leu | Ser | Ala | Glu | Tyr | Leu | Asp | Glu | Pro | Phe | Arg | Ala | Gln |
| | | | 595 | | | | | 600 | | | | | 605 | | |

| agg | gca | atg | agt | gtt | gtc | agt | atc | ata | acc | tcc | gtc | ctt | gag | gaa | ctc | 1872 |
| Arg | Ala | Met | Ser | Val | Val | Ser | Ile | Ile | Thr | Ser | Val | Leu | Glu | Glu | Leu |
| | 610 | | | | | 615 | | | | | 620 | | | | |

| gag | gag | tct | gaa | cag | aag | tgc | cca | ccc | tgc | ttg | acc | agc | ttg | tct | cag | 1920 |
| Glu | Glu | Ser | Glu | Gln | Lys | Cys | Pro | Pro | Cys | Leu | Thr | Ser | Leu | Ser | Gln |
| 625 | | | | | 630 | | | | | 635 | | | | | 640 |

| aag | tat | ctg | atc | tgg | gat | tgc | tgc | ccc | atg | tgg | gtg | aag | ctc | aag | aca | 1968 |
| Lys | Tyr | Leu | Ile | Trp | Asp | Cys | Cys | Pro | Met | Trp | Val | Lys | Leu | Lys | Thr |
| | | | | 645 | | | | | 650 | | | | | 655 | |

| att | ctc | ttt | ggg | ctt | gtg | acg | gat | ccc | ttt | gca | gag | ctc | acc | atc | acc | 2016 |
| Ile | Leu | Phe | Gly | Leu | Val | Thr | Asp | Pro | Phe | Ala | Glu | Leu | Thr | Ile | Thr |
| | | | 660 | | | | | 665 | | | | | 670 | | |

| ttg | tgc | atc | gtg | gtg | aac | acc | atc | ttc | atg | gcc | atg | gag | cac | cat | ggc | 2064 |
| Leu | Cys | Ile | Val | Val | Asn | Thr | Ile | Phe | Met | Ala | Met | Glu | His | His | Gly |
| | | | 675 | | | | | 680 | | | | | 685 | | |

| atg | agc | cct | acc | ttc | gaa | gcc | atg | ctc | cag | ata | ggc | aac | atc | gtc | ttt | 2112 |
| Met | Ser | Pro | Thr | Phe | Glu | Ala | Met | Leu | Gln | Ile | Gly | Asn | Ile | Val | Phe |
| | 690 | | | | | 695 | | | | | 700 | | | | |

| acc | ata | ttt | ttt | act | gct | gaa | atg | gtc | ttc | aaa | atc | att | gcc | ttc | gac | 2160 |
| Thr | Ile | Phe | Phe | Thr | Ala | Glu | Met | Val | Phe | Lys | Ile | Ile | Ala | Phe | Asp |
| 705 | | | | | 710 | | | | | 715 | | | | | 720 |

| cca | tac | tat | tat | ttc | cag | aag | aag | tgg | aat | atc | ttt | gac | tgc | atc | atc | 2208 |
| Pro | Tyr | Tyr | Tyr | Phe | Gln | Lys | Lys | Trp | Asn | Ile | Phe | Asp | Cys | Ile | Ile |
| | | | | 725 | | | | | 730 | | | | | 735 | |

| gtc | act | gtg | agt | ctg | cta | gag | ctg | ggc | gtg | gcc | aag | aag | gga | agc | ctg | 2256 |
| Val | Thr | Val | Ser | Leu | Leu | Glu | Leu | Gly | Val | Ala | Lys | Lys | Gly | Ser | Leu |
| | | | 740 | | | | | 745 | | | | | 750 | | |

| tct | gtg | ctg | cgg | agc | ttc | cgc | ttg | ctg | cgc | gta | ttc | aag | ctg | gcc | aaa | 2304 |
| Ser | Val | Leu | Arg | Ser | Phe | Arg | Leu | Leu | Arg | Val | Phe | Lys | Leu | Ala | Lys |
| | | | 755 | | | | | 760 | | | | | 765 | | |

| tcc | tgg | ccc | acc | tta | aac | aca | ctc | atc | aag | atc | atc | gga | aac | tca | gtg | 2352 |
| Ser | Trp | Pro | Thr | Leu | Asn | Thr | Leu | Ile | Lys | Ile | Ile | Gly | Asn | Ser | Val |
| | 770 | | | | | 775 | | | | | 780 | | | | |

| ggg | gca | ctg | ggg | aac | ctc | acc | atc | atc | ctg | gcc | atc | att | gtc | ttt | gtc | 2400 |
| Gly | Ala | Leu | Gly | Asn | Leu | Thr | Ile | Ile | Leu | Ala | Ile | Ile | Val | Phe | Val |
| 785 | | | | | 790 | | | | | 795 | | | | | 800 |

| ttt | gct | ctg | gtt | ggc | aag | cag | ctc | cta | ggg | gaa | aac | tac | cgt | aac | aac | 2448 |

```
                Phe Ala Leu Val Gly Lys Gln Leu Leu Gly Glu Asn Tyr Arg Asn Asn
                                805                 810                 815 cga aaa aat atc tcc gcg ccc cat gaa gac tgg ccc cgc tgg cac atg        2496
Arg Lys Asn Ile Ser Ala Pro His Glu Asp Trp Pro Arg Trp His Met
            820                 825                 830 cac gac ttc ttc cac tct ttc ctc att gtc ttc cgt atc ctc tgt gga        2544
His Asp Phe Phe His Ser Phe Leu Ile Val Phe Arg Ile Leu Cys Gly
            835                 840                 845 gag tgg att gag aac atg tgg gcc tgc atg gaa gtt ggc caa aaa tcc        2592
Glu Trp Ile Glu Asn Met Trp Ala Cys Met Glu Val Gly Gln Lys Ser
850                 855                 860 ata tgc ctc atc ctt ttc ttg acg gtg atg gtg cta ggg aac ctg gtg        2640
Ile Cys Leu Ile Leu Phe Leu Thr Val Met Val Leu Gly Asn Leu Val
865                 870                 875                 880 gtg ctt aac ctg ttc atc gcc ctg cta ttg aac tct ttc agt gct gac        2688
Val Leu Asn Leu Phe Ile Ala Leu Leu Leu Asn Ser Phe Ser Ala Asp
                885                 890                 895 aac ctc aca gcc ccg gag gac gat ggg gag gtg aac aac ctg cag gtg        2736
Asn Leu Thr Ala Pro Glu Asp Asp Gly Glu Val Asn Asn Leu Gln Val
            900                 905                 910 gcc ctg gca cgg atc cag gtc ttt ggc cat cgt acc aaa cag gct ctt        2784
Ala Leu Ala Arg Ile Gln Val Phe Gly His Arg Thr Lys Gln Ala Leu
            915                 920                 925 tgc agc ttc ttc agc agg tcc tgc cca ttc ccc cag ccc aag gca gag        2832
Cys Ser Phe Phe Ser Arg Ser Cys Pro Phe Pro Gln Pro Lys Ala Glu
            930                 935                 940 cct gag ctg gtg gtg aaa ctc cca ctc tcc agc tcc aag gct gag aac        2880
Pro Glu Leu Val Val Lys Leu Pro Leu Ser Ser Ser Lys Ala Glu Asn
945                 950                 955                 960 cac att gct gcc aac act gcc agg ggg agc tct gga ggg ctc caa gct        2928
His Ile Ala Ala Asn Thr Ala Arg Gly Ser Ser Gly Gly Leu Gln Ala
                965                 970                 975 ccc aga ggc ccc agg gat gag cac agt gac ttc atc gct aat ccg act        2976
Pro Arg Gly Pro Arg Asp Glu His Ser Asp Phe Ile Ala Asn Pro Thr
            980                 985                 990 gtg tgg gtc tct gtg ccc att gct gag ggt gaa tct gat ctt gat gac        3024
Val Trp Val Ser Val Pro Ile Ala Glu Gly Glu Ser Asp Leu Asp Asp
            995                 1000                1005 ttg gag gat gat ggt ggg gaa gat gct cag agc ttc cag cag gaa             3069
Leu Glu Asp Asp Gly Gly Glu Asp Ala Gln Ser Phe Gln Gln Glu
    1010                1015                1020 gtg atc ccc aaa gga cag cag gag cag ctg cag caa gtc gag agg             3114
Val Ile Pro Lys Gly Gln Gln Glu Gln Leu Gln Gln Val Glu Arg
    1025                1030                1035 tgt ggg gac cac ctg aca ccc agg agc cca ggc act gga aca tct             3159
Cys Gly Asp His Leu Thr Pro Arg Ser Pro Gly Thr Gly Thr Ser
    1040                1045                1050 tct gag gac ctg gct cca tcc ctg ggt gag acg tgg aaa gat gag             3204
Ser Glu Asp Leu Ala Pro Ser Leu Gly Glu Thr Trp Lys Asp Glu
    1055                1060                1065 tct gtt cct cag gcc cct gct gag gga gtg gac gac aca agc tcc             3249
Ser Val Pro Gln Ala Pro Ala Glu Gly Val Asp Asp Thr Ser Ser
    1070                1075                1080 tct gag ggc agc acg gtg gac tgc cta gat cct gag gaa atc ctg             3294
Ser Glu Gly Ser Thr Val Asp Cys Leu Asp Pro Glu Glu Ile Leu
    1085                1090                1095 agg aag atc cct gag ctg gca gat gac ctg gaa gaa cca gat gac             3339
Arg Lys Ile Pro Glu Leu Ala Asp Asp Leu Glu Glu Pro Asp Asp
    1100                1105                1110
```

| | | |
|---|---|---|
| tgc ttc aca gaa gga tgc att cgc cac tgt ccc tgc tgc aaa ctg<br>Cys Phe Thr Glu Gly Cys Ile Arg His Cys Pro Cys Cys Lys Leu<br>1115                         1120                     1125 | | 3384 |
| gat acc acc aag agt cca tgg gat gtg ggc tgg cag gtg cgc aag<br>Asp Thr Thr Lys Ser Pro Trp Asp Val Gly Trp Gln Val Arg Lys<br>1130                         1135                     1140 | | 3429 |
| act tgc tac cgt atc gtg gag cac agc tgg ttt gag agc ttc atc<br>Thr Cys Tyr Arg Ile Val Glu His Ser Trp Phe Glu Ser Phe Ile<br>1145                       1150                     1155 | | 3474 |
| atc ttc atg atc ctg ctc agc agt gga tct ctg gcc ttt gaa gac<br>Ile Phe Met Ile Leu Leu Ser Ser Gly Ser Leu Ala Phe Glu Asp<br>1160                       1165                     1170 | | 3519 |
| tat tac ctg gac cag aag ccc acg gtg aaa gct ttg ctg gag tac<br>Tyr Tyr Leu Asp Gln Lys Pro Thr Val Lys Ala Leu Leu Glu Tyr<br>1175                       1180                     1185 | | 3564 |
| act gac agg gtc ttc acc ttt atc ttt gtg ttc gag atg ctg ctt<br>Thr Asp Arg Val Phe Thr Phe Ile Phe Val Phe Glu Met Leu Leu<br>1190                       1195                     1200 | | 3609 |
| aag tgg gtg gcc tat ggc ttc aaa aag tac ttc acc aat gcc tgg<br>Lys Trp Val Ala Tyr Gly Phe Lys Lys Tyr Phe Thr Asn Ala Trp<br>1205                       1210                     1215 | | 3654 |
| tgc tgg ctg gac ttc ctc att gtg aat atc tca ctg ata agt ctc<br>Cys Trp Leu Asp Phe Leu Ile Val Asn Ile Ser Leu Ile Ser Leu<br>1220                       1225                     1230 | | 3699 |
| aca gcg aag att ctg gaa tat tct gaa gtg gct ccc atc aaa gcc<br>Thr Ala Lys Ile Leu Glu Tyr Ser Glu Val Ala Pro Ile Lys Ala<br>1235                       1240                     1245 | | 3744 |
| ctt cga acc ctt cgc gct ctg cgg cca ctg cgg gct ctt tct cga<br>Leu Arg Thr Leu Arg Ala Leu Arg Pro Leu Arg Ala Leu Ser Arg<br>1250                       1255                     1260 | | 3789 |
| ttt gaa ggc atg cgg gtg gtg gtg gat gcc ctg gtg ggc gcc atc<br>Phe Glu Gly Met Arg Val Val Val Asp Ala Leu Val Gly Ala Ile<br>1265                       1270                     1275 | | 3834 |
| cca tcc atc atg aat gtc ctc ctc gtc tgc ctc atc ttc tgg ctc<br>Pro Ser Ile Met Asn Val Leu Leu Val Cys Leu Ile Phe Trp Leu<br>1280                       1285                     1290 | | 3879 |
| atc ttc agc atc atg ggt gtg aac ctc ttc gca ggg aag ttt tgg<br>Ile Phe Ser Ile Met Gly Val Asn Leu Phe Ala Gly Lys Phe Trp<br>1295                       1300                     1305 | | 3924 |
| agg tgc atc aac tat acc gat gga gag ttt tcc ctt gta cct ttg<br>Arg Cys Ile Asn Tyr Thr Asp Gly Glu Phe Ser Leu Val Pro Leu<br>1310                       1315                     1320 | | 3969 |
| tcg att gtg aat aac aag tct gac tgc aag att caa aac tcc act<br>Ser Ile Val Asn Asn Lys Ser Asp Cys Lys Ile Gln Asn Ser Thr<br>1325                       1330                     1335 | | 4014 |
| ggc agc ttc ttc tgg gtc aat gtg aaa gtc aac ttt gat aat gtt<br>Gly Ser Phe Phe Trp Val Asn Val Lys Val Asn Phe Asp Asn Val<br>1340                       1345                     1350 | | 4059 |
| gca atg ggt tac ctt gca ctt ctg cag gtg gca acc ttt aaa ggc<br>Ala Met Gly Tyr Leu Ala Leu Leu Gln Val Ala Thr Phe Lys Gly<br>1355                       1360                     1365 | | 4104 |
| tgg atg gac att atg tat gca gct gtt gat ccc cgg gag gtc aac<br>Trp Met Asp Ile Met Tyr Ala Ala Val Asp Ser Arg Glu Val Asn<br>1370                       1375                     1380 | | 4149 |
| atg caa ccc aag tgg gag gac aac gtg tac atg tat ttg tac ttt<br>Met Gln Pro Lys Trp Glu Asp Asn Val Tyr Met Tyr Leu Tyr Phe<br>1385                       1390                     1395 | | 4194 |
| gtc atc ttc atc att ttt gga ggc ttc ttc aca ctg aat ctc ttt<br>Val Ile Phe Ile Ile Phe Gly Gly Phe Phe Thr Leu Asn Leu Phe<br>1400                       1405                     1410 | | 4239 |

```
gtt ggg gtc ata att gac aac ttc aat caa cag aaa aaa aag tta      4284
Val Gly Val Ile Ile Asp Asn Phe Asn Gln Gln Lys Lys Lys Leu
    1415                1420                1425 ggg ggc cag gac atc ttc atg aca gag gag cag aag aaa tac tac      4329
Gly Gly Gln Asp Ile Phe Met Thr Glu Glu Gln Lys Lys Tyr Tyr
1430                1435                1440 aat gcc atg aag aag ttg ggc tcc aag aag ccc cag aag ccc atc      4374
Asn Ala Met Lys Lys Leu Gly Ser Lys Lys Pro Gln Lys Pro Ile
    1445                1450                1455 cca cgg ccc ctg aac aag ttc cag ggt ttt gtc ttt gac atc gtg      4419
Pro Arg Pro Leu Asn Lys Phe Gln Gly Phe Val Phe Asp Ile Val
1460                1465                1470 acc aga caa gct ttt gac atc acc atc atg gtc ctc atc tgc ctc      4464
Thr Arg Gln Ala Phe Asp Ile Thr Ile Met Val Leu Ile Cys Leu
    1475                1480                1485 aac atg atc acc atg atg gtg gag act gat gac caa agt gaa gaa      4509
Asn Met Ile Thr Met Met Val Glu Thr Asp Asp Gln Ser Glu Glu
1490                1495                1500 aag acg aaa att ctg ggc aaa atc aac cag ttc ttt gtg gcc gtc      4554
Lys Thr Lys Ile Leu Gly Lys Ile Asn Gln Phe Phe Val Ala Val
    1505                1510                1515 ttc aca ggc gaa tgt gtc atg aag atg ttc gct ttg agg cag tac      4599
Phe Thr Gly Glu Cys Val Met Lys Met Phe Ala Leu Arg Gln Tyr
1520                1525                1530 tac ttc aca aat ggc tgg aat gtg ttt gac ttc att gtg gtg gtt      4644
Tyr Phe Thr Asn Gly Trp Asn Val Phe Asp Phe Ile Val Val Val
    1535                1540                1545 ctc tcc att gcg agc ctg att ttt tct gca att ctt aag tca ctt      4689
Leu Ser Ile Ala Ser Leu Ile Phe Ser Ala Ile Leu Lys Ser Leu
1550                1555                1560 caa agt tac ttc tcc cca acg ctc ttc aga gtc atc cgc ctg gcc      4734
Gln Ser Tyr Phe Ser Pro Thr Leu Phe Arg Val Ile Arg Leu Ala
    1565                1570                1575 cga att ggc cgc atc ctc aga ctg atc cga gcg gcc aag ggg atc      4779
Arg Ile Gly Arg Ile Leu Arg Leu Ile Arg Ala Ala Lys Gly Ile
1580                1585                1590 cgc aca ctg ctc ttt gcc ctc atg atg tcc ctg cct gcc ctc ttc      4824
Arg Thr Leu Leu Phe Ala Leu Met Met Ser Leu Pro Ala Leu Phe
    1595                1600                1605 aac atc ggg ctg ttg cta ttc ctt gtc atg ttc atc tac tcc atc      4869
Asn Ile Gly Leu Leu Leu Phe Leu Val Met Phe Ile Tyr Ser Ile
1610                1615                1620 ttc ggt atg tcc agc ttt ccc cat gtg agg tgg gag gct ggc atc      4914
Phe Gly Met Ser Ser Phe Pro His Val Arg Trp Glu Ala Gly Ile
    1625                1630                1635 gac gac atg ttc aac ttc cag acc ttc gcc aac agc atg ctg tgc      4959
Asp Asp Met Phe Asn Phe Gln Thr Phe Ala Asn Ser Met Leu Cys
1640                1645                1650 ctc ttc cag att acc acg tcg gcc ggc tgg gat ggc ctc ctc agc      5004
Leu Phe Gln Ile Thr Thr Ser Ala Gly Trp Asp Gly Leu Leu Ser
    1655                1660                1665 ccc atc ctc aac aca ggg ccc ccc tac tgt gac ccc aat ctg ccc      5049
Pro Ile Leu Asn Thr Gly Pro Pro Tyr Cys Asp Pro Asn Leu Pro
1670                1675                1680 aac agc aat ggc acc aga ggg gac tgt ggg agc cca gcc gta ggc      5094
Asn Ser Asn Gly Thr Arg Gly Asp Cys Gly Ser Pro Ala Val Gly
    1685                1690                1695 atc atc ttc ttc acc acc tac atc atc atc tcc ttc ctc atc gtg      5139
Ile Ile Phe Phe Thr Thr Tyr Ile Ile Ile Ser Phe Leu Ile Val
```

```
gtc aac atg tac att gca gtg att ctg gag aac ttc aat gtg gcc    5184
Val Asn Met Tyr Ile Ala Val Ile Leu Glu Asn Phe Asn Val Ala
    1715                1720                1725 acg gag gag agc act gag cct ctg agt gag gac gac ttt gac atg    5229
Thr Glu Glu Ser Thr Glu Pro Leu Ser Glu Asp Asp Phe Asp Met
    1730                1735                1740 ttc tat gag acc tgg gag aag ttt gac cca gag gcc act cag ttt    5274
Phe Tyr Glu Thr Trp Glu Lys Phe Asp Pro Glu Ala Thr Gln Phe
    1745                1750                1755 att acc ttt tct gct ctc tcg gac ttt gca gac act ctc tct ggt    5319
Ile Thr Phe Ser Ala Leu Ser Asp Phe Ala Asp Thr Leu Ser Gly
    1760                1765                1770 ccc ctg aga atc cca aaa ccc aat cga aat ata ctg atc cag atg    5364
Pro Leu Arg Ile Pro Lys Pro Asn Arg Asn Ile Leu Ile Gln Met
    1775                1780                1785 gac ctg cct ttg gtc cct gga gat aag atc cac tgc ttg gac atc    5409
Asp Leu Pro Leu Val Pro Gly Asp Lys Ile His Cys Leu Asp Ile
    1790                1795                1800 ctt ttt gct ttc acc aag aat gtc cta gga gaa tcc ggg gag ttg    5454
Leu Phe Ala Phe Thr Lys Asn Val Leu Gly Glu Ser Gly Glu Leu
    1805                1810                1815 gat tct ctg aag gca aat atg gag gag aag ttt atg gca act aat    5499
Asp Ser Leu Lys Ala Asn Met Glu Glu Lys Phe Met Ala Thr Asn
    1820                1825                1830 ctt tca aaa tca tcc tat gaa cca ata gca acc act ctc cga tgg    5544
Leu Ser Lys Ser Ser Tyr Glu Pro Ile Ala Thr Thr Leu Arg Trp
    1835                1840                1845 aag caa gaa gac att tca gcc act gtc att caa aag gcc tat cgg    5589
Lys Gln Glu Asp Ile Ser Ala Thr Val Ile Gln Lys Ala Tyr Arg
    1850                1855                1860 agc tat gtg ctg cac cgc tcc atg gca ctc tct aac acc cca tgt    5634
Ser Tyr Val Leu His Arg Ser Met Ala Leu Ser Asn Thr Pro Cys
    1865                1870                1875 gtg ccc aga gct gag gag gag gct gca tca ctc cca gat gaa ggt    5679
Val Pro Arg Ala Glu Glu Glu Ala Ala Ser Leu Pro Asp Glu Gly
    1880                1885                1890 ttt gtt gca ttc aca gca aat gaa aat tgt gta ctc cca gac aaa    5724
Phe Val Ala Phe Thr Ala Asn Glu Asn Cys Val Leu Pro Asp Lys
    1895                1900                1905 tct gaa act gct tct gcc aca tca ttc cca ccg tcc tat gag agt    5769
Ser Glu Thr Ala Ser Ala Thr Ser Phe Pro Pro Ser Tyr Glu Ser
    1910                1915                1920 gtc act aga ggc ctt agt gat aga gtc aac atg agg aca tct agc    5814
Val Thr Arg Gly Leu Ser Asp Arg Val Asn Met Arg Thr Ser Ser
    1925                1930                1935 tca ata caa aat gaa gat gaa gcc acc agt atg gag ctg att gcc    5859
Ser Ile Gln Asn Glu Asp Glu Ala Thr Ser Met Glu Leu Ile Ala
    1940                1945                1950 cct ggg ccc tag tga                                             5874
Pro Gly Pro
    1955

<210> SEQ ID NO 6
<211> LENGTH: 1956
<212> TYPE: PRT
<213> ORGANISM: Homo sapiens

<400> SEQUENCE: 6

Met Glu Phe Pro Ile Gly Ser Leu Glu Thr Asn Asn Phe Arg Arg Phe
```

-continued

```
1               5                   10                  15

Thr Pro Glu Ser Leu Val Glu Ile Glu Lys Gln Ile Ala Ala Lys Gln
                20                  25                  30

Gly Thr Lys Lys Ala Arg Glu Lys His Arg Glu Gln Lys Asp Gln Glu
            35                  40                  45

Glu Lys Pro Arg Pro Gln Leu Asp Leu Lys Ala Cys Asn Gln Leu Pro
        50                  55                  60

Lys Phe Tyr Gly Glu Leu Pro Ala Glu Leu Ile Gly Glu Pro Leu Glu
65                  70                  75                  80

Asp Leu Asp Pro Phe Tyr Ser Thr His Arg Thr Phe Met Val Leu Asn
                85                  90                  95

Lys Gly Arg Thr Ile Ser Arg Phe Ser Ala Thr Arg Ala Leu Trp Leu
                100                 105                 110

Phe Ser Pro Phe Asn Leu Ile Arg Arg Thr Ala Ile Lys Val Ser Val
            115                 120                 125

His Ser Trp Phe Ser Leu Phe Ile Thr Val Thr Ile Leu Val Asn Cys
        130                 135                 140

Val Cys Met Thr Arg Thr Asp Leu Pro Glu Lys Ile Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
                180                 185                 190

Asp Phe Ser Val Ile Thr Leu Ala Tyr Val Gly Thr Ala Ile Asp Leu
            195                 200                 205

Arg Gly Ile Ser Gly Leu Arg Thr Phe Arg Val Leu Arg Ala Leu Lys
        210                 215                 220

Thr Val Ser Val Ile Pro Gly Leu Lys Val Ile Val Gly Ala Leu Ile
225                 230                 235                 240

His Ser Val Lys Lys Leu Ala Asp Val Thr Ile Leu Thr Ile Phe Cys
                245                 250                 255

Leu Ser Val Phe Ala Leu Val Gly Leu Gln Leu Phe Lys Gly Asn Leu
                260                 265                 270

Lys Asn Lys Cys Val Lys Asn Asp Met Ala Val Asn Glu Thr Thr Asn
            275                 280                 285

Tyr Ser Ser His Arg Lys Pro Asp Ile Tyr Ile Asn Lys Arg Gly Thr
        290                 295                 300

Ser Asp Pro Leu Leu Cys Gly Asn Gly Ser Asp Ser Gly His Cys Pro
305                 310                 315                 320

Asp Gly Tyr Ile Cys Leu Lys Thr Ser Asp Asn Pro Asp Phe Asn Tyr
                325                 330                 335

Thr Ser Phe Asp Ser Phe Ala Trp Ala Phe Leu Ser Leu Phe Arg Leu
                340                 345                 350

Met Thr Gln Asp Ser Trp Glu Arg Leu Tyr Gln Gln Thr Leu Arg Thr
            355                 360                 365

Ser Gly Lys Ile Tyr Met Ile Phe Phe Val Leu Val Ile Phe Leu Gly
        370                 375                 380

Ser Phe Tyr Leu Val Asn Leu Ile Leu Ala Val Val Thr Met Ala Tyr
385                 390                 395                 400

Glu Glu Gln Asn Gln Ala Thr Thr Asp Glu Ile Glu Ala Lys Glu Lys
                405                 410                 415

Lys Phe Gln Glu Ala Leu Glu Met Leu Arg Lys Glu Gln Glu Val Leu
            420                 425                 430
```

```
Ala Ala Leu Gly Ile Asp Thr Thr Ser Leu His Ser His Asn Gly Ser
        435                 440                 445

Pro Leu Thr Ser Lys Asn Ala Ser Glu Arg Arg His Arg Ile Lys Pro
    450                 455                 460

Arg Val Ser Glu Gly Ser Thr Glu Asp Asn Lys Ser Pro Arg Ser Asp
465                 470                 475                 480

Pro Tyr Asn Gln Arg Arg Met Ser Phe Leu Gly Leu Ala Ser Gly Lys
                485                 490                 495

Arg Arg Ala Ser His Gly Ser Val Phe His Phe Arg Ser Pro Gly Arg
            500                 505                 510

Asp Ile Ser Leu Pro Glu Gly Val Thr Asp Asp Gly Val Phe Pro Gly
        515                 520                 525

Asp His Glu Ser His Arg Gly Ser Leu Leu Gly Gly Ala Gly
    530                 535                 540         Gly

Gln Gln Gly Pro Leu Pro Arg Ser Pro Leu Pro Gln Pro Ser Asn Pro
545                 550                 555                 560

Asp Ser Arg His Gly Glu Asp Glu His Gln Pro Pro Thr Ser Glu
                565                 570                 575

Leu Ala Pro Gly Ala Val Asp Val Ser Ala Phe Asp Ala Gly Gln Lys
                580                 585                 590

Lys Thr Phe Leu Ser Ala Glu Tyr Leu Asp Glu Pro Phe Arg Ala Gln
            595                 600                 605

Arg Ala Met Ser Val Val Ser Ile Ile Thr Ser Val Leu Glu Glu Leu
            610                 615                 620

Glu Glu Ser Glu Gln Lys Cys Pro Pro Cys Leu Thr Ser Leu Ser Gln
625                 630                 635                 640

Lys Tyr Leu Ile Trp Asp Cys Cys Pro Met Trp Val Lys Leu Lys Thr
                645                 650                 655

Ile Leu Phe Gly Leu Val Thr Asp Pro Phe Ala Glu Leu Thr Ile Thr
            660                 665                 670

Leu Cys Ile Val Val Asn Thr Ile Phe Met Ala Met Glu His His Gly
        675                 680                 685

Met Ser Pro Thr Phe Glu Ala Met Leu Gln Ile Gly Asn Ile Val Phe
    690                 695                 700

Thr Ile Phe Phe Thr Ala Glu Met Val Phe Lys Ile Ile Ala Phe Asp
705                 710                 715                 720

Pro Tyr Tyr Tyr Phe Gln Lys Lys Trp Asn Ile Phe Asp Cys Ile Ile
                725                 730                 735

Val Thr Val Ser Leu Leu Glu Leu Gly Val Ala Lys Lys Gly Ser Leu
            740                 745                 750

Ser Val Leu Arg Ser Phe Arg Leu Leu Arg Val Phe Lys Leu Ala Lys
        755                 760                 765

Ser Trp Pro Thr Leu Asn Thr Leu Ile Lys Ile Ile Gly Asn Ser Val
    770                 775                 780

Gly Ala Leu Gly Asn Leu Thr Ile Ile Leu Ala Ile Ile Val Phe Val
785                 790                 795                 800

Phe Ala Leu Val Gly Lys Gln Leu Leu Gly Glu Asn Tyr Arg Asn Asn
                805                 810                 815

Arg Lys Asn Ile Ser Ala Pro His Glu Asp Trp Pro Arg Trp His Met
            820                 825                 830

His Asp Phe Phe His Ser Phe Leu Ile Val Phe Arg Ile Leu Cys Gly
        835                 840                 845
```

-continued

```
Glu Trp Ile Glu Asn Met Trp Ala Cys Met Glu Val Gly Gln Lys Ser
850                 855                 860

Ile Cys Leu Ile Leu Phe Leu Thr Val Met Val Leu Gly Asn Leu Val
865                 870                 875                 880

Val Leu Asn Leu Phe Ile Ala Leu Leu Leu Asn Ser Phe Ser Ala Asp
                885                 890                 895

Asn Leu Thr Ala Pro Glu Asp Asp Gly Glu Val Asn Asn Leu Gln Val
            900                 905                 910

Ala Leu Ala Arg Ile Gln Val Phe Gly His Arg Thr Lys Gln Ala Leu
            915                 920                 925

Cys Ser Phe Phe Ser Arg Ser Cys Pro Phe Pro Gln Pro Lys Ala Glu
            930                 935                 940

Pro Glu Leu Val Val Lys Leu Pro Leu Ser Ser Ser Lys Ala Glu Asn
945                 950                 955                 960

His Ile Ala Ala Asn Thr Ala Arg Gly Ser Ser Gly Gly Leu Gln Ala
                965                 970                 975

Pro Arg Gly Pro Arg Asp Glu His Ser Asp Phe Ile Ala Asn Pro Thr
            980                 985                 990

Val Trp Val Ser Val Pro Ile Ala  Glu Gly Glu Ser Asp  Leu Asp Asp
            995                 1000                1005

Leu Glu  Asp Asp Gly Gly Glu  Asp Ala Gln Ser Phe  Gln Gln Glu
        1010                1015                1020

Val Ile  Pro Lys Gly Gln Gln  Glu Gln Leu Gln Gln  Val Glu Arg
        1025                1030                1035

Cys Gly  Asp His Leu Thr Pro  Arg Ser Pro Gly Thr  Gly Thr Ser
        1040                1045                1050

Ser Glu  Asp Leu Ala Pro Ser  Leu Gly Glu Thr Trp  Lys Asp Glu
        1055                1060                1065

Ser Val  Pro Gln Ala Pro Ala  Glu Gly Val Asp Asp  Thr Ser Ser
        1070                1075                1080

Ser Glu  Gly Ser Thr Val Asp  Cys Leu Asp Pro Glu  Glu Ile Leu
        1085                1090                1095

Arg Lys  Ile Pro Glu Leu Ala  Asp Asp Leu Glu Glu  Pro Asp Asp
        1100                1105                1110

Cys Phe  Thr Glu Gly Cys Ile  Arg His Cys Pro Cys  Cys Lys Leu
        1115                1120                1125

Asp Thr  Thr Lys Ser Pro Trp  Asp Val Gly Trp Gln  Val Arg Lys
        1130                1135                1140

Thr Cys  Tyr Arg Ile Val Glu  His Ser Trp Phe Glu  Ser Phe Ile
        1145                1150                1155

Ile Phe  Met Ile Leu Leu Ser  Ser Gly Ser Leu Ala  Phe Glu Asp
        1160                1165                1170

Tyr Tyr  Leu Asp Gln Lys Pro  Thr Val Lys Ala Leu  Leu Glu Tyr
        1175                1180                1185

Thr Asp  Arg Val Phe Thr Phe  Ile Phe Val Phe Glu  Met Leu Leu
        1190                1195                1200

Lys Trp  Val Ala Tyr Gly Phe  Lys Lys Tyr Phe Thr  Asn Ala Trp
        1205                1210                1215

Cys Trp  Leu Asp Phe Leu Ile  Val Asn Ile Ser Leu  Ile Ser Leu
        1220                1225                1230

Thr Ala  Lys Ile Leu Glu Tyr  Ser Glu Val Ala Pro  Ile Lys Ala
        1235                1240                1245

Leu Arg  Thr Leu Arg Ala Leu  Arg Pro Leu Arg Ala  Leu Ser Arg
```

-continued

```
                1250                1255                1260

Phe Glu Gly Met Arg Val Val Asp Ala Leu Val Gly Ala Ile
    1265                1270                1275

Pro Ser Ile Met Asn Val Leu Leu Val Cys Leu Ile Phe Trp Leu
    1280                1285                1290

Ile Phe Ser Ile Met Gly Val Asn Leu Phe Ala Gly Lys Phe Trp
    1295                1300                1305

Arg Cys Ile Asn Tyr Thr Asp Gly Glu Phe Ser Leu Val Pro Leu
    1310                1315                1320

Ser Ile Val Asn Asn Lys Ser Asp Cys Lys Ile Gln Asn Ser Thr
    1325                1330                1335

Gly Ser Phe Phe Trp Val Asn Val Lys Val Asn Phe Asp Asn Val
    1340                1345                1350

Ala Met Gly Tyr Leu Ala Leu Leu Gln Val Ala Thr Phe Lys Gly
    1355                1360                1365

Trp Met Asp Ile Met Tyr Ala Ala Val Asp Ser Arg Glu Val Asn
    1370                1375                1380

Met Gln Pro Lys Trp Glu Asp Asn Val Tyr Met Tyr Leu Tyr Phe
    1385                1390                1395

Val Ile Phe Ile Ile Phe Gly Gly Phe Phe Thr Leu Asn Leu Phe
    1400                1405                1410

Val Gly Val Ile Ile Asp Asn Phe Asn Gln Gln Lys Lys Lys Leu
    1415                1420                1425

Gly Gly Gln Asp Ile Phe Met Thr Glu Glu Gln Lys Lys Tyr Tyr
    1430                1435                1440

Asn Ala Met Lys Lys Leu Gly Ser Lys Lys Pro Gln Lys Pro Ile
    1445                1450                1455

Pro Arg Pro Leu Asn Lys Phe Gln Gly Phe Val Phe Asp Ile Val
    1460                1465                1470

Thr Arg Gln Ala Phe Asp Ile Thr Ile Met Val Leu Ile Cys Leu
    1475                1480                1485

Asn Met Ile Thr Met Met Val Glu Thr Asp Asp Gln Ser Glu Glu
    1490                1495                1500

Lys Thr Lys Ile Leu Gly Lys Ile Asn Gln Phe Phe Val Ala Val
    1505                1510                1515

Phe Thr Gly Glu Cys Val Met Lys Met Phe Ala Leu Arg Gln Tyr
    1520                1525                1530

Tyr Phe Thr Asn Gly Trp Asn Val Phe Asp Phe Ile Val Val Val
    1535                1540                1545

Leu Ser Ile Ala Ser Leu Ile Phe Ser Ala Ile Leu Lys Ser Leu
    1550                1555                1560

Gln Ser Tyr Phe Ser Pro Thr Leu Phe Arg Val Ile Arg Leu Ala
    1565                1570                1575

Arg Ile Gly Arg Ile Leu Arg Leu Ile Arg Ala Ala Lys Gly Ile
    1580                1585                1590

Arg Thr Leu Leu Phe Ala Leu Met Met Ser Leu Pro Ala Leu Phe
    1595                1600                1605

Asn Ile Gly Leu Leu Leu Phe Leu Val Met Phe Ile Tyr Ser Ile
    1610                1615                1620

Phe Gly Met Ser Ser Phe Pro His Val Arg Trp Glu Ala Gly Ile
    1625                1630                1635

Asp Asp Met Phe Asn Phe Gln Thr Phe Ala Asn Ser Met Leu Cys
    1640                1645                1650
```

| Leu Phe Gln Ile Thr Thr Ser Ala Gly Trp Asp Gly Leu Leu Ser |
|---|
| 1655 1660 1665 |

Pro Ile Leu Asn Thr Gly Pro Pro Tyr Cys Asp Pro Asn Leu Pro
    1670            1675            1680

Asn Ser Asn Gly Thr Arg Gly Asp Cys Gly Ser Pro Ala Val Gly
    1685            1690            1695

Ile Ile Phe Phe Thr Thr Tyr Ile Ile Ile Ser Phe Leu Ile Val
    1700            1705            1710

Val Asn Met Tyr Ile Ala Val Ile Leu Glu Asn Phe Asn Val Ala
    1715            1720            1725

Thr Glu Glu Ser Thr Glu Pro Leu Ser Glu Asp Asp Phe Asp Met
    1730            1735            1740

Phe Tyr Glu Thr Trp Glu Lys Phe Asp Pro Glu Ala Thr Gln Phe
    1745            1750            1755

Ile Thr Phe Ser Ala Leu Ser Asp Phe Ala Asp Thr Leu Ser Gly
    1760            1765            1770

Pro Leu Arg Ile Pro Lys Pro Asn Arg Asn Ile Leu Ile Gln Met
    1775            1780            1785

Asp Leu Pro Leu Val Pro Gly Asp Lys Ile His Cys Leu Asp Ile
    1790            1795            1800

Leu Phe Ala Phe Thr Lys Asn Val Leu Gly Glu Ser Gly Glu Leu
    1805            1810            1815

Asp Ser Leu Lys Ala Asn Met Glu Glu Lys Phe Met Ala Thr Asn
    1820            1825            1830

Leu Ser Lys Ser Ser Tyr Glu Pro Ile Ala Thr Thr Leu Arg Trp
    1835            1840            1845

Lys Gln Glu Asp Ile Ser Ala Thr Val Ile Gln Lys Ala Tyr Arg
    1850            1855            1860

Ser Tyr Val Leu His Arg Ser Met Ala Leu Ser Asn Thr Pro Cys
    1865            1870            1875

Val Pro Arg Ala Glu Glu Glu Ala Ala Ser Leu Pro Asp Glu Gly
    1880            1885            1890

Phe Val Ala Phe Thr Ala Asn Glu Asn Cys Val Leu Pro Asp Lys
    1895            1900            1905

Ser Glu Thr Ala Ser Ala Thr Ser Phe Pro Pro Ser Tyr Glu Ser
    1910            1915            1920

Val Thr Arg Gly Leu Ser Asp Arg Val Asn Met Arg Thr Ser Ser
    1925            1930            1935

Ser Ile Gln Asn Glu Asp Glu Ala Thr Ser Met Glu Leu Ile Ala
    1940            1945            1950

Pro Gly Pro
    1955

<210> SEQ ID NO 7
<211> LENGTH: 649
<212> TYPE: DNA
<213> ORGANISM: Homo sapiens
<220> FEATURE:
<221> NAME/KEY: CDS
<222> LOCATION: (112)..(402)
<223> OTHER INFORMATION:

<400> SEQUENCE: 7
agaatacact cacaagccac tccgctgctc gcctctccgc cccgcgtcca gctcgcccag    60
ctcgcccagc gtccgccgcg cctcgccaag gcttcaacgg accacaccaa a atg cca   117

```
                                            Met Pro
                                             1
tct caa atg gaa cac gcc atg gaa acc atg atg ttt aca ttt cac aaa        165
Ser Gln Met Glu His Ala Met Glu Thr Met Met Phe Thr Phe His Lys
    5                   10                  15 ttc gct ggg gat aaa ggc tac tta aca aag gag gac ctg aga gta ctc        213
Phe Ala Gly Asp Lys Gly Tyr Leu Thr Lys Glu Asp Leu Arg Val Leu
        20                  25                  30 atg gaa aag gag ttc cct gga ttt ttg gaa aat caa aaa gac cct ctg        261
Met Glu Lys Glu Phe Pro Gly Phe Leu Glu Asn Gln Lys Asp Pro Leu
35                  40                  45                  50 gct gtg gac aaa ata atg aag gac ctg gac cag tgt aga gat ggc aaa        309
Ala Val Asp Lys Ile Met Lys Asp Leu Asp Gln Cys Arg Asp Gly Lys
                55                  60                  65 gtg ggc ttc cag agc ttc ttt tcc cta att gcg ggc ctc acc att gca        357
Val Gly Phe Gln Ser Phe Phe Ser Leu Ile Ala Gly Leu Thr Ile Ala
            70                  75                  80 tgc aat gac tat ttt gta gta cac atg aag cag aag gga aag aag            402
Cys Asn Asp Tyr Phe Val Val His Met Lys Gln Lys Gly Lys Lys
                85                  90                  95 taggcagaaa tgagcagttc gctcctccct gataagagtt gtccaaaggg tcgcttaagg      462
aatctgcccc acagcttccc ccatagaagg atttcatgag cagatcagga cacttagcaa      522
atgtaaaaat aaaatctaac tctcatttga caagcagaga aagaaaagtt aaataccaga      582
taagcttttg attttgtat  tgtttgcatc ccttgccct  caataaataa agttctttt       642 tagttcc                                                                649

<210> SEQ ID NO 8
<211> LENGTH: 97
<212> TYPE: PRT
<213> ORGANISM: Homo sapiens

<400> SEQUENCE: 8

Met Pro Ser Gln Met Glu His Ala Met Glu Thr Met Met Phe Thr Phe
1               5                   10                  15

His Lys Phe Ala Gly Asp Lys Gly Tyr Leu Thr Lys Glu Asp Leu Arg
            20                  25                  30

Val Leu Met Glu Lys Glu Phe Pro Gly Phe Leu Glu Asn Gln Lys Asp
        35                  40                  45

Pro Leu Ala Val Asp Lys Ile Met Lys Asp Leu Asp Gln Cys Arg Asp
    50                  55                  60

Gly Lys Val Gly Phe Gln Ser Phe Phe Ser Leu Ile Ala Gly Leu Thr
65                  70                  75                  80

Ile Ala Cys Asn Asp Tyr Phe Val Val His Met Lys Gln Lys Gly Lys
                85                  90                  95

Lys

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
gcgaattcat ggagctcccc tttg                                             24

<210> SEQ ID NO 10
```

```
<211> LENGTH: 29
<212> TYPE: DNA
<213> ORGANISM: Artificial sequence
<220> FEATURE:
<223> OTHER INFORMATION: Primer

<400> SEQUENCE: 10
tatagcggcc gctttgatgg ctgttcttc                                           29

<210> SEQ ID NO 11
<211> LENGTH: 18
<212> TYPE: DNA
<213> ORGANISM: Artificial sequence
<220> FEATURE:
<223> OTHER INFORMATION: Primer

<400> SEQUENCE: 11
catcccaaat ggagcatg                                                       18

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
ctacttcttc tgcttcatgt gtactac                                             27

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
ggtgtggtga aggacaac                                                       18

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
catagggaga agggtttc                                                       18

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
accccaccgt gttcttcgac                                                     20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
```
catttgccat ggacaagatg                                          20

<210> SEQ ID NO 17
<211> LENGTH: 18
<212> TYPE: DNA
<213> ORGANISM: Artificial sequence
<220> FEATURE:
<223> OTHER INFORMATION: Primer

<400> SEQUENCE: 17
catcccaaat ggagcatg                                            18

<210> SEQ ID NO 18
<211> LENGTH: 27
<212> TYPE: DNA
<213> ORGANISM: Artificial sequence
<220> FEATURE:
<223> OTHER INFORMATION: Primer

<400> SEQUENCE: 18
ctacttcttc tgcttcatgt gtactac                                  27

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
ggaattcatg gagctcccct ttgcg                                    25

<210> SEQ ID NO 20
<211> LENGTH: 30
<212> TYPE: DNA
<213> ORGANISM: Artificial sequence
<220> FEATURE:
<223> OTHER INFORMATION: Primer

<400> SEQUENCE: 20
aattgcggcc gcagacgctt tgatggctgt                               30

<210> SEQ ID NO 21
<211> LENGTH: 25
<212> TYPE: DNA
<213> ORGANISM: Artificial sequence
<220> FEATURE:
<223> OTHER INFORMATION: Primer

<400> SEQUENCE: 21
ggaattcatg gagctcccct ttgcg                                    25

<210> SEQ ID NO 22
<211> LENGTH: 28
<212> TYPE: DNA
<213> ORGANISM: Artificial sequence
<220> FEATURE:
<223> OTHER INFORMATION: Primer

<400> SEQUENCE: 22
ggaattcaag cagattgctg ctcaccgc                                 28

<210> SEQ ID NO 23
<211> LENGTH: 28
<212> TYPE: DNA

```
<213> ORGANISM: Artificial sequence
<220> FEATURE:
<223> OTHER INFORMATION: Primer

<400> SEQUENCE: 23
ggaattcccc aggcctcagc tggacttg                                            28

<210> SEQ ID NO 24
<211> LENGTH: 33
<212> TYPE: DNA
<213> ORGANISM: Artificial sequence
<220> FEATURE:
<223> OTHER INFORMATION: Primer

<400> SEQUENCE: 24
aattgcggcc gcctcgatct ctgccagtga ctc                                      33

<210> SEQ ID NO 25
<211> LENGTH: 33
<212> TYPE: DNA
<213> ORGANISM: Artificial sequence
<220> FEATURE:
<223> OTHER INFORMATION: Primer

<400> SEQUENCE: 25
aattgcggcc gccttctcgc ccttgtcctc ctg                                      33

<210> SEQ ID NO 26
<211> LENGTH: 30
<212> TYPE: DNA
<213> ORGANISM: Artificial sequence
<220> FEATURE:
<223> OTHER INFORMATION: Primer

<400> SEQUENCE: 26
aattgcggcc gcagacgctt tgatggctgt                                          30

<210> SEQ ID NO 27
<211> LENGTH: 23
<212> TYPE: DNA
<213> ORGANISM: Artificial sequence
<220> FEATURE:
<223> OTHER INFORMATION: Primer

<400> SEQUENCE: 27
gggctggcaa gccacgtttg gtg                                                 23

<210> SEQ ID NO 28
<211> LENGTH: 23
<212> TYPE: DNA
<213> ORGANISM: Artificial sequence
<220> FEATURE:
<223> OTHER INFORMATION: Primer

<400> SEQUENCE: 28
ccgggagctg catgtgtcag agg                                                 23

<210> SEQ ID NO 29
<211> LENGTH: 28
<212> TYPE: DNA
<213> ORGANISM: Artificial sequence
<220> FEATURE:
<223> OTHER INFORMATION: Primer

<400> SEQUENCE: 29
ggaattcccc aggcctcagc tggacttg                                            28
```

```
<210> SEQ ID NO 30
<211> LENGTH: 28
<212> TYPE: DNA
<213> ORGANISM: Artificial sequence
<220> FEATURE:
<223> OTHER INFORMATION: Primer

<400> SEQUENCE: 30
ggaattcctg gtcggggagc ccctggag                                          28

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
ggaattcttc agtgccactt gggcc                                             25

<210> SEQ ID NO 32
<211> LENGTH: 27
<212> TYPE: DNA
<213> ORGANISM: Artificial sequence
<220> FEATURE:
<223> OTHER INFORMATION: Primer

<400> SEQUENCE: 32
aattgcggcc gcttctgctg ggagctc                                           27

<210> SEQ ID NO 33
<211> LENGTH: 30
<212> TYPE: DNA
<213> ORGANISM: Artificial sequence
<220> FEATURE:
<223> OTHER INFORMATION: Primer

<400> SEQUENCE: 33
aattgcggcc gctctggaaa tggtcctgct                                        30

<210> SEQ ID NO 34
<211> LENGTH: 4
<212> TYPE: PRT
<213> ORGANISM: Artificial sequence
<220> FEATURE:
<223> OTHER INFORMATION: core tetrapeptide of calpactin-I
<220> FEATURE:
<221> NAME/KEY: MISC_FEATURE
<222> LOCATION: (3)..(3)
<223> OTHER INFORMATION: Xaa = any amino acid

<400> SEQUENCE: 34

Lys Val Xaa Asp
1

<210> SEQ ID NO 35
<211> LENGTH: 23
<212> TYPE: DNA
<213> ORGANISM: Artificial sequence
<220> FEATURE:
<223> OTHER INFORMATION: Primer

<400> SEQUENCE: 35
aaccatggat gccatcccaa atg                                               23
```

```
<210> SEQ ID NO 36
<211> LENGTH: 22
<212> TYPE: DNA
<213> ORGANISM: Artificial sequence
<220> FEATURE:
<223> OTHER INFORMATION: Primer

<400> SEQUENCE: 36
aaccatgggt gctcatggaa ag                                    22

<210> SEQ ID NO 37
<211> LENGTH: 21
<212> TYPE: DNA
<213> ORGANISM: Artificial sequence
<220> FEATURE:
<223> OTHER INFORMATION: Primer

<400> SEQUENCE: 37
aaccatgggg gctcatcatt g                                     21

<210> SEQ ID NO 38
<211> LENGTH: 27
<212> TYPE: DNA
<213> ORGANISM: Artificial sequence
<220> FEATURE:
<223> OTHER INFORMATION: Primer

<400> SEQUENCE: 38
gatctagatc tcaggtcctc ctttgtc                               27

<210> SEQ ID NO 39
<211> LENGTH: 28
<212> TYPE: DNA
<213> ORGANISM: Artificial sequence
<220> FEATURE:
<223> OTHER INFORMATION: Primer

<400> SEQUENCE: 39
gatctagacg ccactagtga tagaaagc                              28

<210> SEQ ID NO 40
<211> LENGTH: 32
<212> TYPE: DNA
<213> ORGANISM: Artificial sequence
<220> FEATURE:
<223> OTHER INFORMATION: Primer

<400> SEQUENCE: 40
gatctagact acttcttctg cttcatgtgt ac                         32

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
accacatggt ccttcttgag                                       20

<210> SEQ ID NO 42
<211> LENGTH: 23
<212> TYPE: DNA
<213> ORGANISM: Artificial sequence
<220> FEATURE:
<223> OTHER INFORMATION: Primer
```

```
<400> SEQUENCE: 42
tgctgtttaa atattaaaca ggg                                              23

<210> SEQ ID NO 43
<211> LENGTH: 29
<212> TYPE: DNA
<213> ORGANISM: Artificial sequence
<220> FEATURE:
<223> OTHER INFORMATION: Primer

<400> SEQUENCE: 43
aaccatgggt ggacaaaata atgaaagac                                        29

<210> SEQ ID NO 44
<211> LENGTH: 27
<212> TYPE: DNA
<213> ORGANISM: Artificial sequence
<220> FEATURE:
<223> OTHER INFORMATION: Primer

<400> SEQUENCE: 44
gatctagaag ccagagggtc cttttga                                          27

<210> SEQ ID NO 45
<211> LENGTH: 5
<212> TYPE: PRT
<213> ORGANISM: Artificial sequence
<220> FEATURE:
<223> OTHER INFORMATION: pentapeptide in p11 EF hand binding region of
      p11-2

<400> SEQUENCE: 45

Asp Gln Cys Arg Asp
1               5

<210> SEQ ID NO 46
<211> LENGTH: 5
<212> TYPE: PRT
<213> ORGANISM: Artificial sequence
<220> FEATURE:
<223> OTHER INFORMATION: mutated pentapeptide in p11 EF hand binding
      region of p11-2

<400> SEQUENCE: 46

Ala Gln Ala Arg Ala
1               5

<210> SEQ ID NO 47
<211> LENGTH: 23
<212> TYPE: DNA
<213> ORGANISM: Artificial sequence
<220> FEATURE:
<223> OTHER INFORMATION: Primer

<400> SEQUENCE: 47
aaccatggat gccatcccaa atg                                              23

<210> SEQ ID NO 48
<211> LENGTH: 17
<212> TYPE: DNA
<213> ORGANISM: Artificial sequence
<220> FEATURE:
<223> OTHER INFORMATION: Primer

<400> SEQUENCE: 48
ggcccaggcc cgagctg                                                     17
```

<210> SEQ ID NO 49
<211> LENGTH: 32
<212> TYPE: DNA
<213> ORGANISM: Artificial sequence
<220> FEATURE:
<223> OTHER INFORMATION: Primer

<400> SEQUENCE: 49
gatctagact acttcttctg cttcatgtgt ac                                      32

<210> SEQ ID NO 50
<211> LENGTH: 19
<212> TYPE: DNA
<213> ORGANISM: Artificial sequence
<220> FEATURE:
<223> OTHER INFORMATION: Primer

<400> SEQUENCE: 50
tccagctcgg gcctgggcc                                                     19

<210> SEQ ID NO 51
<211> LENGTH: 6
<212> TYPE: PRT
<213> ORGANISM: Artificial sequence
<220> FEATURE:
<223> OTHER INFORMATION: hexapeptide in p11 EF hand binding region of
      p11-2

<400> SEQUENCE: 51

Lys Val Gly Phe Gln Ser
1               5

<210> SEQ ID NO 52
<211> LENGTH: 6
<212> TYPE: PRT
<213> ORGANISM: Artificial sequence
<220> FEATURE:
<223> OTHER INFORMATION: mutated hexapeptide in p11 EF hand binding
      region of p11-2

<400> SEQUENCE: 52

Ala Val Ala Phe Gln Ala
1               5

<210> SEQ ID NO 53
<211> LENGTH: 21
<212> TYPE: DNA
<213> ORGANISM: Artificial sequence
<220> FEATURE:
<223> OTHER INFORMATION: Primer

<400> SEQUENCE: 53
gagcagtggc cttccaggcc t                                                  21

<210> SEQ ID NO 54
<211> LENGTH: 25
<212> TYPE: DNA
<213> ORGANISM: Artificial sequence
<220> FEATURE:
<223> OTHER INFORMATION: Primer

<400> SEQUENCE: 54
tagaaaggcc tggaaggcca ctgct                                              25

<210> SEQ ID NO 55

-continued

```
<211> LENGTH: 20
<212> TYPE: DNA
<213> ORGANISM: Artificial sequence
<220> FEATURE:
<223> OTHER INFORMATION: Primer

<400> SEQUENCE: 55
accacatggt ccttcttgag                                              20
```

METHOD OF IDENTIFYING A MODULATOR OF A VOLTAGE-GATED SODIUM CHANNEL USING CELLS EXPRESSING NAV1.8 AND P11

This application is the US national phase of International Application No. PCT/GB02/03852 filed in English on 20 Aug. 2002, which designated the US. PCT/GB02/03852 claims priority to GB Application No. 0120238.1 filed 20 Aug. 2001. The entire contents of these applications are incorporated herein by reference.

FIELD OF THE INVENTION

The present invention relates generally to methods and materials for use in regulating or modulating voltage gated $Na^+$ channels (VGSCs).

BACKGROUND OF THE INVENTION

VGSCs are transmembrane proteins responsible for bestowing electrical excitability upon almost all excitable membranes. The pore is gated by depolarization of the cell membrane, transiently allowing $Na^+$ ions to enter into the cell, and generating the upswing of an action potential. Following activation, VGSCs undergo inactivation, limiting the action potential duration, and allowing rapid membrane repolarization is followed by a return to the resting state. All known VGSCs exhibit remarkable functional similarities and this is reflected in a high degree of amino-acid sequence homology. However, natural toxins are known to discriminate well between $Na^+$ channel subtypes. For example, tetrodotoxin (TTX) from the Puffer fish, can selectively block subtypes of neuronal VGSCs at single nanomolar concentrations, whereas other neuronal VGSCs remain unblocked by the toxin at micromolar concentrations. These neuronal VGSCs that are TTX-insensitive or resistant (TTX-R) are found in the peripheral nervous system, and are exclusively associated with nerves involved in the transmission of pain (see e.g. Akopian et al (1999) "The tetrodotoxin-resistant sodium channel SNS plays a specialised role in pain pathways". Nature Neuroscience 2, 541-548).

WO 97/01577 (University College London) relates to a novel 1,957 amino acid TTX-insensitive VGSC from mammalian sensory neurons (which has been designated Nav 1.8). U.S. Pat. No. 6,184,349 (Syntex) discusses VGSCs. The sodium channel Nav1.8 (also known as SNS or PN3) is expressed exclusively in small diameter sensory neurones that correspond to Aδ or C-fibre nociceptors, which are the cells that transmit pain signals. One key feature of Nav1.8 pharmacology is its resistance to high concentrations of tetrodotoxin (TTX), which blocks most other sodium channels. Evidence for a role of Nav1.8 in pain signalling comes largely from knock out mice and from studies where the channel is downregulated with antisense oligonucleotides. These experiments suggest that Nav1.8 is important in models of inflammatory, neuropathic and visceral pain.

Nav1.9 (SNS2) is also found exclusively in sensory neurones that signal pain and is also resistant to TTX. The properties of the channel suggest that it is not involved in generation or propagation of action potentials but is involved in setting the level of excitability of the cell. There is evidence that G-proteins can activate Nav1.9, which in turn increases neuronal excitability and makes the cell more likely to fire. There is no direct evidence for involvement of Nav1.9 in pain models, but given its function in the cell and the restricted distribution, it could play a major role in producing the is hyper-reactivity associated with many chronic pain states.

Nav 1.3 is found in brains of adult animals and is sensitive to TTX. There is normally no Nav1.3 in sensory neurones, but after nerve damage, levels are upregulated massively. Again there is no direct evidence for involvement of Nav1.3 in pain, but the selective upregulation after nerve injury suggests that it might play a role in transmission of neuropathic pain signals.

p11 is a member of the S-100 family small calcium binding proteins. p11 is also known as annexin-II light chain, lipocortin-II light chain, calpactin I light chain, 42 C, or S-100 related protein, and these terms may be used interchangeably herein. It is present in a variety of cells separately or as a heterotetramer. The heterotetramer is composed of two copies of p36, also known as annexin-II or calpactin-I heavy chain, and two copies of p11. The association of p11 with p36 is $Ca^{2+}$-independent and of high affinity, and binding of p11 to p36 strongly enhances p36's ability to bundle F-actin. Within the cell, the heterotetramer is localized at the cytoplasmic surface of the plasma membrane in the submembranous cytoskeleton, and it is suggested that the complex may play a role in membrane trafficking events such as exocytosis, endocytosis and cell-cell adhesion. It is also known that p11 is a strong substrate for tyrosine kinase pp60src and its phosphorylation is a negative modulator of tetramerization and protein function.

SUMMARY OF THE INVENTION

The present invention derived from the Inventors' finding that the p11 protein is involved in the functional expression of voltage gated sodium channels (VGSCs). The present invention provides screening methods for the identification of compounds which are capable of modulating VGSCs. In one aspect there is provided a method of identifying a modulator of a VGSC, which method comprises:

(a) bringing into contact a VGSC, a p11 peptide and a test compound under conditions where the VGSC and the p11 peptide are capable of forming a complex in the absence of the test compound; and (b) measuring an activity of the VGSC, wherein a change in the activity of the VGSC relative to the activity in the absence of the test compound indicates that the test compound is a modulator of said VGSC.

The invention further provides a method of enhancing the functional expression of a voltage gated sodium channel (VGSC) in a cell which method comprises the step of increasing the level of p11 in the cell.

The present invention also provides a host cell capable of expressing a VGSC and a p11 peptide wherein said VGSC and/or said p11 peptide is expressed from one or more heterologous expression vectors within said cell. Such a host cell may be used in the screening methods of the invention.

The invention also provides compounds identified as putative modulators of VGSC activity by the screening methods of the invention. Such compounds may be used in the treatment or disorders which involve VGSCs. The invention therefore provides the use of a compound identified by a screening method of the invention in the manufacture of a medicament for modulating the functional expression of a voltage gated sodium channel. Also provided is a method of treating a disorder or condition associated with the activity of a voltage gated sodium channel, said method comprising administering to an individual in need thereof a compound identified by a screening method of the invention.

Also within the scope of the invention are methods of decreasing VGSC activity or functional expression by decreasing the levels of p11. The present invention therefore provides the use of an inhibitor of p11 activity or expression in the manufacture of a medicament for modulating the functional expression of a voltage gated sodium channel. Also provided is a method of treating a disorder or condition associated with the activity of a voltage gated sodium channel, said method comprising administering to an individual in need thereof an inhibitor of p11 activity or expression.

The invention also provides isolated peptides derived from VGSCs and p11 which comprise the amino acids involved in binding between these two proteins. There is therefore provided a peptide comprising at least 10 contiguous amino acids of: (a) the sequence from amino acid 75 to amino acid 102 of SEQ ID NO: 2, or (b) a sequence having at least 65% amino acid sequence identity to (a); wherein said peptide is capable of specifically binding a p11 peptide and is less than 1000 amino acids in length. There is also provided a peptide comprising at least 10 contiguous amino acids of: (a) the sequence from amino acid 33 to amino acid 77 of SEQ ID NO: 4, or (b) a sequence having at least 70% amino acid sequence identity to (a); wherein said peptide is capable of specifically binding a voltage gated sodium channel and is less than 80 amino acids in length.

BRIEF DESCRIPTION OF THE SEQUENCES

Figure 1:
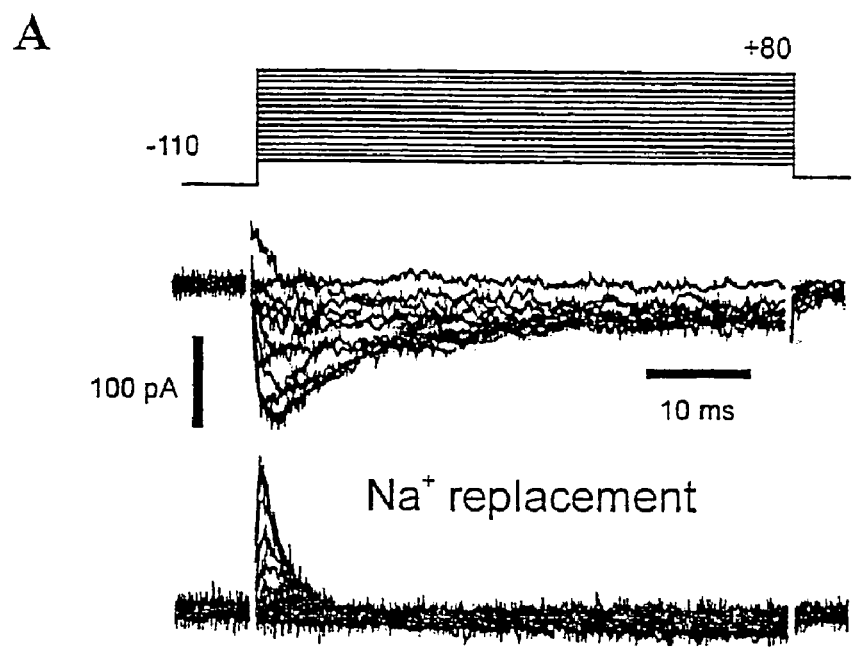
FIG. 1A: High threshold TTX-resistant $Na^+$ current recorded from fluorescent CHO-SNS22 cells after transfection with GFP-p11 cDNA expression vector. $Na^+$ current has characteristically slow kinetics, and inward current is abolished by removing extracellular $Na^+$ ions. Pulse protocol is shown above.
FIG. 1B: Average current ($I/I_{max}$)–voltage ($E_m$) relationship for the $Na^+$ current in CHO-SNS22 cells (n=5). The threshold for activation is close to −5 mV and the current peaks at +40 mV.
Figure 1:
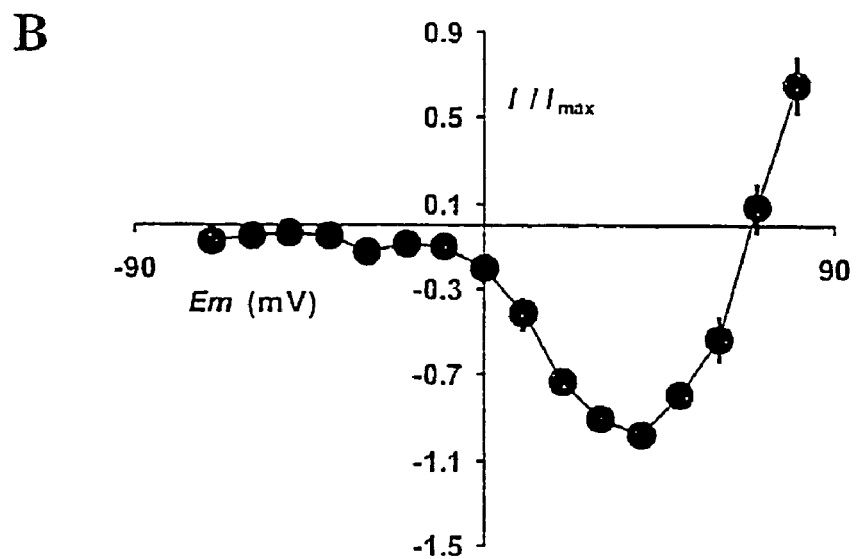

SEQ ID NO: 1 is the DNA sequence of the rat Nav 1.8 receptor gene and SEQ ID NO: 2 is the amino acid sequence that it encodes. These sequences are publicly available from GenBank under accession number X92184.

SEQ ID NO: 3 is the DNA sequence of the rat p11 gene and SEQ ID NO: 4 is the amino acid sequence that it encodes. These sequences are publicly available from GenBank under accession number J03627.

SEQ ID NO: 5 is the DNA sequence of the human Nav 1.8 receptor gene and SEQ ID NO: 6 is the amino acid sequence that it encodes. These sequences are publicly available from GenBank under accession number AF117907.

SEQ ID NO: 7 is the DNA sequence of the human p11 gene and SEQ ID NO: 8 is the amino acid sequence that it encodes. These sequences are publicly available from GenBank under accession number NM_002966.

DETAILED DESCRIPTION OF THE INVENTION

The present invention relates generally to screening methods for the identification of compounds capable of regulating or modulating the functional expression of sodium channels. Also provided are methods wherein such compounds are used in the treatment of conditions associated with sodium channel function, for example in the prevention or treatment of pain.

As described in more detail below, this interaction may be exploited, inter alia, in:

(i) enhancing the functional expression of a sodium channel e.g. in cell lines which may be used for conventional modulator-screening purposes, (ii) defining a novel target (i.e. disruption of the protein-protein interaction site itself) for devising modulators which could lower the functional expression of a sodium channel.

Sodium Channels and p11 Peptides

The present application relates to the regulation or modulation of functional expression of sodium channels, in particular voltage gated sodium channels (VGSCs). Table 1 indicates the sequence identity between various VGSC molecules, using the rat Nav 1.8 channel as a basis for comparison:

TABLE 1

| Channel | Rat 1.8 | Rat 1.5 | Rat 1.9 | Rat 1.3 |
| --- | --- | --- | --- | --- |
| Accession number | X92184 | M27902 | AF059030 | Y00766 |
| With gaps | 100 | 61% | 49% | 57% |
| Without gaps | 100 | 63% | 55% | 62% |

For comparison, rat 1.8 vs human 1.8 scores 83% (with gaps) or 84% (without gaps) identity using this method
Amino acid identity was determined over the full protein sequence. The Nav1.8 protein sequence was aligned with a second sequence using Clustal. The number of identical amino acids was then scored for each pair and divided by the total number of amino acids in the alignment (with gaps) or the total number of aligned amino acids (without gaps).

A VGSC of the invention is any VGSC which has the ability to specifically bind a p11 peptide. By specifically bind it is meant that the VGSC binds the p11 peptide preferentially to a non-p11 peptide, for example a VGSC binds more strongly to a p11 peptide than to a randomly generated non-p11 peptide sequence.

In particular, the present invention relates to VGSCs that are associated with responses to pain or are involved in pain signalling. A suitable sodium channel is is preferably a VGSC that is expressed in sensory neurons. For example, a suitable VGSC may be a sensory neuron specific (SNS) VGSC, for example Nav 1.8 or Nav 1.9, or may be upregulated in sensory neurons in response to pain, for example Nav 1.3. A suitable VGSC may be tetrodotoxin (TTX) insensitive or resistant, that is, it may remain unblocked by TTX at micromolar concentrations.

In one aspect, a VGSC for use in methods of the invention is a Nav 1.8, Nav 1.9 or Nav 1.3 channel. The nucleotide and amino acid sequences for the Nav 1.8, rat Nav 1.9 and rat Nav 1.3 channels are publicly available, for example rat sequences are available from GenBank under the accession numbers given in Table 1. The nucleotide and amino acid sequences for rat Nav 1.3 are given in SEQ ID Nos: 1 and 2 respectively and the nucleotide and amino acid sequences for human Nav 1.8 are given in SEQ ID Nos: 5 and 6 respectively.

A suitable VGSC for use in the methods of the invention may be any of these VGSCs or a species or allelic variant of any thereof. There is no requirement that the proteins (or nucleic acids) employed in the present invention have to include the full-length "authentic" sequence of the proteins as they occur in nature. A suitable VGSC may therefore also be a variant of any of these VGSCs which retains activity as a sodium channel. For example, a suitable VGSC may have greater than 65%, greater than 70%, greater than 75%, greater than 85%, greater than 95% or greater than 98% amino acid identity with any of the Nav 1.8, Nav 1.9 or Nav 1.3 sequences.

A suitable variant channel is one which retains sodium channel function. For example, a suitable variant of the Nav 1.8 sodium channel may have the normal function of a VGSC. The function of a VGSC may be measured as described below. It may also retain the tetrodotoxin insensitivity of the Nav 1.8 channel.

A suitable variant preferably also retains the ability to bind p11. For example, a suitable variant channel may retain the intracellular domain of a wild type VGSC. For example, a preferred variant of the rat Nav 1.8 channel may retain the N-terminal intracellular domain found at positions 1 to 127 of SEQ ID NO: 2. A suitable variant channel may have a sequence comprising amino acids 53 to 127 or amino acids 75 to 102 of SEQ ID NO: 2, which are shown below to be involved in binding to p11 protein, or a species or allelic variant of this region.

A suitable variant VGSC may be a fragment of a wild type VGSC or of a variant thereof as described above. A suitable fragment may be a truncated VGSC, wherein, for example, 1%, 2%, 5%, 10%, 15%, 20%, 25%, 50% or more of the original VGSC sequence has been removed. A suitable fragment may consist of or comprise a fragment of a full length VGSC, for example, 1%, 2%, 5%, 10%, 15%, 20%, 25%, 50% or more of a full length sequence. A suitable fragment may be any fragment which retains the ability to bind a p11 peptide. A suitable fragment may also retain the ability to function as a sodium channel. A fragment may be, for example, 10, 20, 30, 50, 75, 100, 150, 200, 300, 500, 750, 1000, 1500 or more amino acids in length.

A suitable VGSC may comprise a fragment of a wild-type or variant VGSC sequence as part of its amino acid sequence. Such a variant will retain the ability to bind p11, and optionally the ability to act as a sodium channel. A VGSC fragment which retains the ability to bind p11 may be derived from the intracellular domain of the full-length VGSC. Such a fragment may include the entire intracellular domain or a part thereof. A preferred fragment of the Nav 1.8 channel may be selected from the N-terminal intracellular domain, for example amino acids 1 to 127 of SEQ ID NO: 2. Preferably fragments represent sequences which are believed to be either unique to the channel, or are at least well conserved among VGSCs. Preferred fragments of SEQ ID NO: 2 include amino acid positions 1 to 25, 26 to 50 and 51 to 127. A VGSC fragment which retains the ability to bind p11 may consist of or comprise the sequence of amino acids 53 to 127 or 75 to 102 of SEQ ID NO: 2. Such a VGSC fragment may be, for example, 28 to 50, 28 to 100, 28 to 200, 28 to 500, 28 to 1000 amino acids in length or larger. A suitable VGSC fragment may comprise a part of the sequence of amino acids 53 to 127 or 75 to 102, for example, 5, 10, 15, 20, or 25 contiguous amino acids from this region or from a variant of this region as defined above, which retain the ability to bind p11.

Thus, in one aspect there is provided a peptide comprising at least 10, at least 15, at least 20 or at least 25 contiguous amino acids of (a) the sequence from amino acid 75 to amino acid 102 of SEQ ID NO: 2, or (b) a sequence having at least 65%, at least 70%, at least 75%, at least 85%, at least 95% or at least 98% amino acid sequence identity to (a), wherein said peptide is capable of specifically binding a p11 peptide and is less than 1000 amino acids in length. Said peptide may be for example less than 500 amino acids, less than 300 amino acids, less than 200 amino acids, less than 100 amino acids or less than 50 amino acids in length.

In one aspect, a VGSC of the invention has an amino acid sequence comprising:

(a) the amino acid sequence of SEQ ID NO: 2 or SEQ ID NO: 4;

(b) a species or allelic variant of (a);

(c) a variant of (a) having at least 65% amino acid sequence identity thereto; or (d) a fragment of any of (a) to (c).

Such a VGSC will retain the ability to bind a p11 protein. Such a VGSC may also retain the ability to mediate a $Na^+$ current across a membrane, such as the plasma membrane of the cell.

A suitable variant sodium channel may be derived as described below.

The present invention also relates to the discovery that the VGSC Nav 1.8 interacts with p11 protein. According to the present invention, a suitable p11 for use in the present invention may be a naturally occurring p11 peptide, or may be an artificially constructed p11 peptide. A suitable p11 peptide may be a full-length p11 protein or a species or allelic variant thereof. For example, a suitable p11 peptide may have the rat amino acid sequence given in SEQ ID NO: 4 or the human amino acid sequence given in SEQ ID NO: 8. A suitable p11 may alternatively be a species or allelic variant of the p11 peptide of SEQ ID NO: 4 or SEQ ID NO: 8.

There is no requirement that the proteins (or nucleic acids) employed in the present invention have to include the full-length "authentic" sequence of the proteins as they occurs in nature. Variants may be used (e.g. which are derived from p11 for example) which retain its activity to modify the VGSC functional expression. Modified p11 sequences according to the present invention may have a sequence at least 70% identical to the sequence of an endogenous p11 such as the rat p11 of SEQ ID NO: 4 or the human p11 of SEQ ID NO: 8. Typically there would be 75% or more, 85% or more 95% or more or 98% or more identity between the modified sequence and the authentic sequence. A variant may comprise a fragment of a naturally occurring p11 sequence. For example, a variant p11 peptide may comprise amino acids 33 to 77 of SEQ ID NO: 4 which are shown below to be involved in the modification of VGSC functional expression. Also envisaged are variant p11 peptides comprising variants, for example allelic or species variants of such fragments.

A suitable variant p11 may be a fragment of a wild type p11 or of a variant thereof as described above. A suitable fragment may be a truncated p11, wherein, for example, 1%, 2%, 5%, 10%, 15%, 20%, 25%, 50% or more of the original p11 sequence has been removed. A suitable fragment may consist of or comprise a fragment of a full length p11, for example, 1%, 2%, 5%, 10%, 15%, 20%, 25%. 50% or more of a full length sequence. A suitable fragment may be any fragment which retains the ability to bind a VGSC. A fragment may be, for example, 5, 10, 15, 20, 25, 30, 40, 50, 60, 70 80, 90 or more amino acids in length.

A suitable p11 may comprise a fragment of a wild-type or variant p11 sequence as part of its amino acid sequence. Such a variant will retain the ability to bind VGSC. A p11 fragment which retains the ability to bind VGSC may consist of or comprise the sequence of amino acids 33 to 77 of SEQ ID NO: 4. Such a p11 fragment may be, for example, 44 to 50, 44 to 60, 44 to 70, 44 to 80 amino acids in length or larger. A suitable p11 fragment may comprise a part of the sequence of amino acids 33 to 77 of SEQ ID NO: 4, for example, 5, 10, 15, 20, 25, 20, 40 or more amino acids from this region which retain the ability to bind VGSC.

Thus, in one aspect there is provided a peptide comprising at least 10, at least 15, at least 20, at least 25, at least 35 or at least 45 contiguous amino acids of (a) the sequence from amino acid 33 to amino acid 77 of SEQ ID NO: 4, or (b) a sequence having at least 70%, at least 75%, at least 85%, at least 95% or at least 98% amino acid sequence identity to (a), wherein said peptide is capable of specifically binding a voltage gated sodium channel and is less than 80 amino acids in length. Said peptide may be for example less than 70 amino acids, less than 60 amino acids, less than 50 amino acids, less than 40 amino acids or less than 30 amino acids in length.

A p11 peptide for use in the methods of the present invention may therefore have an amino acid sequence comprising:

(a) the amino acid sequence of SEQ ID NO: 4 or SEQ ID NO: 8;

(b) a species or allelic variant of (a);

(c) a variant of (a) having at least 70% amino acid sequence identity thereto; or (d) a fragment of any of (a) to (c).

Such a p11 peptide will retain the ability to bind a VGSC.

The term "derived" includes variants produced by modification of the authentic native sequence e.g. by introducing changes into the full-length or part-length sequence, for example substitutions, insertions, and/or deletions. This may be achieved by any appropriate technique, including restriction of the sequence with an endonuclease followed by the insertion of a selected base sequence (using linkers if required) and ligation. Also possible is PCR-mediated mutagenesis using mutant primers. It may, for instance, be preferable to add in or remove restriction sites in order to facilitate further cloning. There may be up to five, for example up to ten or up to twenty or more nucleotide deletions, insertions and/or substitutions made to the full-length or part length sequence provided functionality is not totally lost.

Similarity or identity may be as defined and determined by the TBLASTN program, of Altschul et al. (1990) *J. Mol. Biol.* 215: 403-10, or BestFit, which is part of the Wisconsin Package, Version 8, September 1994, (Genetics Computer Group, 575 Science Drive, Madison, Wis., USA, Wisconsin 53711). Preferably sequence comparisons are made using FASTA and FASTP (see Pearson & Lipman, 1988. Methods in Enzymology 183: 63-98). Parameters are preferably set, using the default matrix, as follows: Gapopen (penalty for the first residue in a gap): −16 for DNA; Gapext (penalty for additional residues in a gap): −4 for DNA KTUP word length: 6 for DNA. Alternatively, homology in this context can be judged by probing under appropriate stringency conditions. One common formula for calculating the stringency conditions required to achieve hybridization between (complementary) nucleic acid molecules of a specified sequence homology is (Sambrook et al., 1989): $T_m$=81.5° C.+16.6 Log [Na+]+0.41 (% G+C)−0.63 (% formamide)−600/#bp in duplex. Preferred conditions will give hybridisation of molecules at least 70% homology as described above.

Nucleic Acids

The present invention also encompasses the use of nucleic acids which encode VGSCs or p11 peptides of the invention to produce such proteins. For example, provided in the sequence listing are nucleic acid sequences encoding the rat Nav 1.8 channel (SEQ ID NO: 1), the rat p11 protein (SEQ ID NO: 3), the human Nav 1.8 channel (SEQ ID NO: 5) and the human p11 protein (SEQ ID NO: 7).

Generally, nucleic acids of, or for use in, the present invention (e.g. encoding p11) may be provided isolated and/or purified from their natural environment, in substantially pure or homogeneous form, or free or substantially free of other nucleic acids of the species of origin. Where used herein, the term "isolated" encompasses all of these possibilities. Nucleic acid according to the present invention may be in the form of, or derived from, cDNA, RNA, genomic DNA and modified nucleic acids or nucleic acid analogs.

Thus the invention also relates, in a further aspect, to use of a heterologous nucleic acid molecule which comprises a nucleotide sequence encoding p11 described above, in the various methods of the invention.

The term "heterologous" is used broadly herein to indicate that the gene/sequence of nucleotides in question (e.g. encoding p11) have been introduced into cells using genetic engineering, i.e. by human intervention. A heterologous gene may replace an endogenous equivalent gene, i.e. one which normally performs the same or a similar function, or the inserted sequence may be additional to the endogenous gene or other sequence. Nucleic acid heterologous to a cell may be non-naturally occurring in cells of that type, variety or species.

Nucleic acid sequences which encode a polypeptide in accordance with the present invention can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al., Short Protocols in Molecular Biology, John Wiley and Sons, 1992). These techniques include (i) the use of the polymerase chain reaction (PCR) to amplify samples of the relevant nucleic acid, e.g. from genomic sources, (ii) chemical synthesis, or (iii) preparation of cDNA sequences.

Constricts and Vectors

In cell-based assay embodiments of the present invention, the polypeptide of interest can be introduced by causing or allowing the expression in a cell of an expression construct or vector.

A construct for delivery of a nucleic acid of the invention may include any other regulatory sequences or structural elements as would commonly be included in such a system, and as is described below. The vector components will usually include, but is are not limited to, one or more of an origin of replication, one or more marker genes, an enhancer element, a promoter, and a transcription termination sequence. Construction of suitable vectors containing one or more of these components employs standard ligation techniques which are known to the skilled artisan. Nucleic acid sequences which enable a vector to replicate in one or more selected host cells are well known for a variety of bacteria, yeast, and viruses. For example, various viral origins (SV40, polyoma, adenovirus, VSV or BPV) are useful for cloning vectors in mammalian cells.

Particularly preferred for use herein is an expression vector e.g. in the form of a plasmid, cosmid, viral particle, phage, or any other suitable vector or construct which can be taken up by a cell and used to express a coding sequence. Expression vectors usually contain a promoter which is operably linked to the protein-encoding nucleic acid sequence of interest, so as to direct mRNA synthesis. Promoters recognized by a variety of potential host cells are well known. "Operably linked" means joined as part of the same nucleic acid molecule, suitably positioned and oriented for transcription to be initiated from the promoter. DNA operably linked to a promoter is "under transcriptional control" of the promoter. Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g. the actin promoter or an immunoglobulin promoter, and from heat-shock promoters, provided such promoters are compatible with the host cell systems.

Where a cell line is used in which both the VGSC and p11 are heterologous, these proteins may be expressed from a single vector or from two separate vectors. More than one copy of the protein encoding sequences may be present in the vector.

Expression vectors of the invention may also contain one or more selection genes. Typical selection genes encode proteins that (a) confer resistance to antibiotics or other toxins e.g. ampicillin, neomycin, methotrexate, or tetracycline, (b) complement auxotrophic deficiencies, or (c) supply critical nutrients not available from complex media, e.g., the gene encoding D-alanine racemase for Bacilli. The protein encoding sequences may include reporter genes which may be any suitable reporter gene used in the art. Such reporter genes includes chloramphenicol acetyl transferase (CAT), β-galactosidase, luciferase or GFP.

Cells

The methods referred to above may therefore further include introducing the nucleic acid into a host cell. The introduction, which may be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For example, the calcium phosphate precipitation method of Graham and van der Eb, Virology 52:456-457 (1978) can be employed. General aspects of mammalian cell host system transformations have been described in U.S. Pat. No. 4,399,216. For various techniques for transforming mammalian cells, see Keown et al., Methods in Enzymology, 185:527 537 (1990) and Mansour et al., Nature 336:348-352 (1988).

The cells used in methods of the present invention may be present in, or extracted from, organisms, may be cells or cell lines transiently or permanently transfected or transformed with the appropriate proteins or nucleic acids encoding them or may be cells or cell lines which express the required VGSC and p11 peptide from endogenous (i.e. not artificially introduced) genes. The term "in vivo" where used herein includes all these possibilities. Thus in vivo methods may be performed in a suitably responsive cell line which expresses the VGSC (either as a native channel, or from a vector introduced into the cell). The cell line may be in tissue culture or may be, for example, a cell line xenograft in a non-human animal subject.

The cell lines used in assays of the invention may be used to achieve transient expression of p11 or may be stably transfected with constructs which express a p11 peptide. The cell lines may be transiently or stably transfected with constructs which express the VGSC. Means to generate stably transformed cell lines are well known in the art and such means may be used here. Preferred cells are non-neuronal e.g. CHO cell cells.

The level of p11 or VGSC expression in a cell may be increased by introducing it into the cells directly or by causing or allowing expression from heterologous nucleic acid encoding therefore. A cell may be used which endogenously expresses p11 and/or VGSC without the introduction of heterologous genes. Such a cell may endogenously express sufficient levels of p11 and/or VGSC for use in the methods of the invention, or may express only low levels of p11 and/or VGSC which require supplementation as described herein. A cell may be used which endogenously expresses no p11 or VGSC, but which can be made to express p11 and VGSC using methods such as those described herein.

The present invention therefore encompasses host cells which express VGSC and p11 peptide according to the present invention, one or both of which may be heterologously expressed. In such cells, said VGSC and said p11 peptide should be expressed such that the two proteins interact to upregulate the functional expression of the VGSC. Such host cells are suitable for use in the screening methods of the invention.

Host cells transfected or transformed with expression or cloning vectors described herein may be cultured in conventional nutrient media. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

Transgenic Organisms

Host cells according to the present invention (i.e. including heterologous p11 for increasing VGSC expression) may be comprised in a transgenic animal, and the present invention further provides uses of the transgenic animal in the methods herein. The transgenic organisms of the invention all include within a plurality of their cells a cloned recombinant or synthetic DNA sequence which encodes the heterologous p11.

For more details regarding the production of transgenic organisms, and specifically transgenic mice, refer to U.S. Pat. No. 4,873,191, issued Oct. 10, 1989 (incorporated herein by reference to disclose methods for producing transgenic mice), and to the numerous scientific publications referred to and cited therein.

The foregoing discussion has been generally concerned with uses of the nucleic acids of the present invention for production of functional polypeptides, thereby increasing the concentration of p11 in a cell so as to increase functional expression of the VGSC. However, as explained below, the information disclosed herein may also be used to reduce the activity of p11 in cells in which it is desired to do so, with a corresponding reduction in the functional expression of the VGSC.

Increasing Functional VGSC Expression

The present invention provides a method for enhancing the functional expression of a VGSC comprising exposing said channel to a p11 peptide. Thus the invention provides a method of modifying the translocation of a voltage gated sodium channel into a plasma membrane of a cell, which method comprises the step of altering the concentration of p11 in the cell.

Such a method may be used to increase the functional expression of a VGSC in the cell. The level of "functional expression" of the channel is used herein to describe the quantity or proportion of the channel which is active within a cell. "Active" in this context means capable of mediating a sodium current across a membrane in response to an appropriate stimulus.

Thus a further aspect of the present invention provides a method of enhancing the functional expression of a VGSC in a cell, which method comprises the step of increasing the level of p11 in the cell.

The VGSC may be any VGSC of the invention as described above. The p11 peptide may be any p11 of the invention as described above. The cell may be any suitable cell line as described above. Preferably the VGSC is expressed within the cell. The p11 peptide may also be expressed within the cell or may be applied to the cell. The VGSC and/or the p11 peptide may be expressed from endogenous genes within the cell or from heterologous genes that have been introduced into the cell, for example by transfaction of the cell with one or more vectors as described above.

Preferably, a p11 peptide of the invention is either applied to the cell or is heterologously expressed within the cell. The p11 peptide may be expressed under the control of an inducible promoter so that the level of p11 expressed within the cell may be regulated. By heterologously providing p11 to the cell, the functional expression of the VGSC, that is the recruitment of the VGSC to the membrane and the subsequent activity of the VGSC, may be enhanced.

A cell in which the functional expression of a VGSC has been enhanced by such a method may be subsequently used in a screening method of the invention. Such a cell will have enhanced VGSC functional expression and will therefore be particularly sensitive to any changes in VGSC activity that a test compound may cause.

Assays Using Enhanced VGSC Functional Expression

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

One aspect of the present invention is based on the enhanced VGSC functionality which can be achieved using p11. This effect can be used to generate assays having enhanced sensitivity. Such systems (e.g. cell lines) are particularly useful for identifying compounds capable of modulating the VGSC.

"Modulating" herein includes any effect on the functional expression of a VGSC. This includes blocking or inhibiting the activity of the channel in the presence of, or in response to, an appropriate stimulator. Alternatively modulators may enhance the activity of the channel. Preferred modulators are channel blockers or inhibitors.

The screening methods described herein generally assess whether a test compound or putative modulator are capable of causing a change in an activity of a VGSC. Any activity normally exhibited by a VGSC may be measured. For example, a suitable activity may be the ability of the VGSC to bind specifically to or to form a complex with a p11 peptide. Such a binding activity may be measured using methods known in the art, such as those described herein. A test compound which modulates this binding activity is a potential modulator of VGSC. Another activity of VGSCs which may be measured is the ability to function as a sodium channel. This may be measured using methods known in the art such as those described herein. For example, a test compound may affect the ability of a VGSC to produce a sodium current across a membrane in which the VGSC is present. Such assays may include the application of a specific stimulus, for example a stimulus which would normally result in sodium current flow.

The present aspect of the invention may take the form of any, preferably in vivo, assay utilising the enhanced VGSC functionality which can be achieved using p11. The term "in vivo" includes cell lines and the like as described above. This assay is carried out in a cell in which the functional expression of the VGSC has been enhanced by exposure to a p11 peptide. Thus the in vivo assays may be performed in a suitably responsive cell line which expresses a VGSC of the invention (either as a native channel, or from a vector introduced into the cell) and in which p11 is either applied to said cell or is expressed within said cell (endogenously or heterologously). Preferably, a p11 peptide of the invention is either applied to the cell or is heterologously expressed within the cell. The p11 peptide may be expressed under the control of an inducible promoter so that the level of p11 expressed within the cell may be regulated. By heterologously providing p11 to the cell, the functional expression of the VGSC, that is the recruitment of the VGSC to the membrane and the subsequent activity of the VGSC, may be enhanced. In the in vivo assays of the invention, it will be desirable to achieve sufficient levels of p11 to recruit VGSC to the membrane to enhance its functional expression. However, the precise format of the assays of the invention may be varied by those of skill in the art using routine skill and knowledge.

The invention therefore provides methods for increasing the functional expression of a VGSC in a cell, comprising exposing said VGSC to a p11 peptide of the invention. Cells having enhanced functional expression of VGSC are also envisaged as an aspect of the invention.

The invention further provides methods of modulating a VGSC the functional expression of which has been enhanced, which method comprises the step of contacting said channel with a putative modulator thereof.

The contacting step may be in vivo or in vitro, as described in more detail below. One suitable system for testing modulation (e.g. inhibition or blockage) of, for example, the SNS sodium channel (Nav 1.8), is the CHO-SNS employed in the Examples below. Other systems for testing modulation are disclosed e.g. in WO 97/01577. Membrane currents are conveniently measured with the whole-cell configuration of the patch clamp method, according to the procedure detailed in the Examples. Preferred voltage clamps are those in which the cell potential is stepped from the holding potential of about −90 mV to test potentials that range from about −110 mV to +60 to 80 mV. In order to isolate TTX-R sodium currents, TTX, 4-aminopyridine (AP) and $CdCl_2$ were used with tetraethyl ammonium ions (TEA), and Cs. However those skilled in the art will be aware of other such compounds and combinations of compounds which could be used analogously.

In one embodiment there is provided a method for identifying a modulator of a VGSC which method comprises the steps of:

(i) providing a cell in which the functional activity of said channel has been enhanced as described above (e.g. by increasing the concentration of p11 in the cell e.g. by causing or allowing expression from a nucleic acid encoding p11 in the cell);

(ii) contacting (directly or indirectly) the channel in the cell with the test compound, (iii) measuring the activity (e.g. the current mediated by the channel, optionally in the presence of an activator) of the channel.

Preferably the activity before and after the contacting with the test compound will be compared, and optionally the relative activity will be correlated with the modulatory activity of the test compound. Compounds may therefore be identified that are capable of modulating the activity of a VGSC. Such compounds may have therapeutic use in the treatment or prevention of conditions associated with VGSC activity as described in more detail below.

Methods of the present invention may be employed in high throughput screens analogous to those well known in the art—see e.g. WO 00/16231 (Navicyte); WO 00/14540 (Tibotec); DE 19840545 (Jerini Biotools); WO 00/12755 (Higher Council for Scientific Research); WO 00/12705 (Pausch M H; Wess J); WO 00/11216 (Bristol-Myers Squibb); U.S. Pat. No. 6,027,873 (Genencor Intl.); DE 19835071 (Carl Zeiss; F Hoffman-La Roche); WO 00/03805 (CombiChem); WO 00/02899 (Biocept); WO 00/02045 (Euroscreen); U.S. Pat. No. 6,007,690 (Aclara Biosciences).

Interaction Between p11 and VGSC

The interaction of a p11 peptide and a VGSC may be investigated, optionally using fragments of one or both proteins. The proteins or fragments may be labeled to facilitate this.

For example the proteins or fragments can be linked to a coupling partner, e.g. a label. Techniques for coupling labels to peptidyl coupling partners are well known in the art. Labels may be fluorescent marker compounds expressed as fusions e.g. GFP. In another embodiment the proteins or fragments may be radiolabeled. Radiolabeling of peptides can be achieved using various methods known in the art. For example, peptides can be labelled with a radioactive isotope through use of a chelating agent or by covalent labelling with a material capable of direct reaction with a peptide (such as iodine), as well as by direct labelling (substitution of a radioactive isotope, such as $^{14}C$ or tritium, for an atom present in the peptide) or $^{35}S$-methionine which may be incorporated into recombinantly produced proteins.

Generally, radiolabelled peptides containing tyrosine will be prepared using $I^{125}$, or by tritium exchange. See U.S. Pat. No. 5,384,113, as well as numerous other patent and other publications, for general techniques available for the radiolabeling process. As used herein, the term "radiolabeled" describes a product that has been attached to a radioisotope by any of the various known methods, such as by covalent labeling or covalent binding, by a direct substitution method, or by a chelation method.

Other suitable detectable labels include tags such as an HA tag, GST or histidine. Recombinantly produced protein may also be expressed as a fusion protein containing an epitope which can be labelled with an antibody. Alternatively, an antibody against the proteins can be obtained using conventional methodology.

In a further aspect of the invention, the labeling methods described above are used to identify the p11 binding site on the VGSC (and vice versa). Such methods will generally comprise the steps of producing a fragment of one or both proteins, and contacting said fragment with its binding partner (all or part of it) and determining whether binding occurs. Preferably one or both partners will be labelled and\or tagged to facilitate the detection of binding.

For example, in order to identify the binding site for p11 in the VGSC, small segments of the VGSC believed to contain said binding site may be tested.

Preferred fragments may be selected from the N-terminal intracellular domain of the VGSC, for example from amino acids 1 to 127 of the rat Nav1.8 sequence as given in SEQ ID NO: 2. Preferably fragments represent sequences which are believed to be either unique to the channel, or are at least well conserved among VGSCs. Preferred fragments of the Nav 1.8 channel of SEQ ID NO: 2 may include amino acid positions 1 to 25, 26 to 50 and 51 to 127.

As described in the Examples below, it appears that the binding site for p11 on the rat Nav1.8 channel lies in the N-terminal intracellular domain between amino acids 53 and 127 (with reference to SEQ ID NO: 2), and preferably between amino acids 75 and 102. Similarly, the rat p11 protein binds to the rat Nav1.8 channel via a region at amino acids 33 to 77 (with reference to SEQ ID NO: 4). Similar methods may be used to localise or identify binding sites in other VGSCs or p11 peptides.

Binding fragments can be identified using the GST "pull down assay". This is described in more detail in the Examples hereinafter, wherein rat p11 protein produced in COS-7 cells by lipofection was mixed with fragments of SNS (Nav1.8) N-terminal which were fused to GST made in bacteria. These protein complexes are collected by glutathione beads and p11 is recovered only when the VGSC fragment has one or more binding site(s) for it. In other embodiments, co-immunoprecipitation or an overlay assay can be done in place or in addition to the "pull down" assay.

After narrowing down to one (or more) of the N-terminal fragments, the binding site can be further investigated e.g. using point mutations by recombinant PCR or a uracil containing vector system (Journal of Physiology (1999) 516.2, 433-446 cAMP-dependent phosphorylation of the tetrodotoxin-resistant voltage-dependent sodium channel SNS. E. M. Fitzgerald, K. Okuse, J. N. Wood, A. C. Dolphin, S. J. Moss). Since the target cDNA (e.g. corresponding to a fragment described above of about one third of N-terminal domain) may be fairly short, recombinant PCR may be preferred. Mutated N-terminal fragments may again be tested e.g. in the GST "pull down" assay, to precisely identify the interaction site between the VGSC and p11.

Once identified the binding site may be modeled in 3 dimensions to produce mimetics. Alternatively it may be used directly e.g. as a binding partner (optionally in phage display) to screen for compounds.

Assay for Modulators of Interaction

In a further aspect the present invention provides an assay for a modulator of the functional expression of VGSC in a cell, which assay comprises the steps of:

a) bringing into contact a VGSC, a p11 peptide, and a putative modulator compound under conditions where the VGSC and the p11, in the absence of modulator, are capable of forming a complex; and b) measuring the degree of inhibition of complex formation caused by said modulator compound.

The present invention further provides an assay for a modulator of the functional expression of a VGSC in a cell, which assay comprises the steps of:

a) bringing into contact a VGSC, a p11 peptide, and a putative modulator compound under conditions where the VGSC and the p11, in the absence of modulator, are capable of forming a complex; and b) exposing the VGSC to a stimulus such as to produce to a sodium current across a membrane in which the VGSC is present, c) measuring the degree of inhibition of the current caused by said modulator compound.

An inhibition in the current indicates that the compound is a potential modulator of VGSC activity. Such a compound may have therapeutic use in the treatment or prevention of conditions associated with VGSC activity, as described in more detail below.

One assay format which is widely used in the art to study the interaction of two proteins is a two-hybrid assay. This assay may be adapted for use in the present invention. A two-hybrid assay comprises the expression in a host cell of the two proteins, one being a fusion protein comprising a DNA binding domain (DBD), such as the yeast GAL4 binding domain, and the other being a fusion protein comprising an activation domain, such as that from GAL4 or VP16. In such a case the host cell (which may be bacterial, yeast, insect or mammalian, particularly yeast or mammalian) will carry a reporter gene construct with a promoter comprising a DNA binding elements compatible with the DBD. The reporter gene may be a reporter gene such as chloramphenical acetyl transferase, luciferase, green fluorescent protein (GFP) and β-galactosidase, with luciferase being particularly preferred.

Two-hybrid assays may be in accordance with those disclosed by Fields and Song, 1989. Nature 340; 245-246. In such an assay the DNA binding domain (DBD) and the transcriptional activation domain (TAD) of the yeast GAL4 transcription factor are fused to the first and second molecules respectively whose interaction is to be investigated. A functional GAL4 transcription factor is restored only when two molecules of interest interact. Thus, interaction of the molecules may be measured by the use of a reporter gene operably linked to a GAL4 DNA binding site which is capable of activating transcription of said reporter gene.

Thus two hybrid assays may be performed in the presence of a potential modulator compound and the effect of the modulator will be reflected in the change in transcription level of the reporter gene construct compared to the transcription level in the absence of a modulator.

Host cells in which the two-hybrid assay may be conducted include mammalian, insect and yeast cells, with yeast cells (such as S. cerevisiae and S. pombe) being particularly preferred.

The interaction between p11 and a VGSC may also be assessed in mammalian cells. Cells or cell lines are derived which (over) express the VGSC in a zero p11 background or in the background of endogenously expressed p11 or in the background of (over)expressed p11. This can be done by (co)transfecting the VGSC with or without p11 into the cell. Any cell may be chosen and VGSC expression and/or p11 expression may be transient or stable. The effect of p11 on the VGSC can be determined by comparing ion flux across the channel in cells (over)expressing p11 with those that do not (over)express p11 or show low levels of p11 expression. Other ways of measuring the effect of p11 on the VGSC are by assaying the extent of membrane localisation of the VGSC in whole cells or in isolated membranes. VGSC localisation can be assessed by antibody staining in cellular immunofluorescence assays, or by western blotting of membrane fractions or by toxin binding on whole cells or membrane fractions. The interaction can also be derived in co-immunoprecipitation assays of p11 and VGSC. Inhibitors of the interaction will inhibit the functionality or the membrane localisation of VGSC, or the extent of co-immunoprecipitation between p11 and VGSC in the cells (over)expressing p11.

Another assay format measures directly, in vivo or in vitro, the interaction between p11 and the VGSC by labelling one of these proteins with a detectable label, as described above, and bringing it into contact with the other protein which has been optionally immobilised on a solid support, either prior to or after proteins have been brought into contact with each other.

The protein which is optionally immobilized on a solid support may be immobilized using an antibody against that protein bound to a solid support or via other technologies which are known per se. In the Examples which follow a preferred in vitro interaction is illustrated which utilises a fusion protein of the SNS sodium channel (Nav1.8) fused to glutathione-S-transferase (GST). Such a fusion protein may be immobilized on glutathione sepharose or agarose beads.

In an in vitro assay format of the type described above the putative inhibitor compound can be assayed by determining its ability to diminish the amount of labelled p11 (e.g. the GFP-fusion described hereinafter) which binds to the immobilized (e.g. GST-SNS) sodium channel. This may be determined by fractionating the glutathione beads by SDS-polyacrylamide gel electrophoresis. Alternatively, the beads may be rinsed to remove unbound protein and the amount of protein which has bound can be determined by counting the amount of label present in, for example, a suitable scintillation counter.

Another assay format is dissociation enhanced lanthanide fluorescent immunoassay (DELFIA) (Ogata et al, 1992). This is a solid phase based system for measuring the interaction of two macromolecules. Typically one molecule (either VGSC or p11) is immobilised to the surface of a multi well plate and the other molecule is added in solution to this. Detection of the bound partner is achieved by using a label consisting of a chelate of a rare earth metal. This label can be directly attached to the interacting molecule or may be introduced to the complex via an antibody to the molecule or to the molecules epitope tag. Alternatively, the molecule may be attached to biotin and a streptavidin-rare earth chelate used as the label. The rare earth used in the label may be europium, samarium, terbium or dysprosium. After washing to remove unbound label, a detergent containing low pH buffer is added to dissociate the rare earth metal from the chelate. The highly fluorescent metal ions are then quantitated by time resolved fluorimetry. A number of labelled reagents are commercially available for this technique, including streptavidin, antibodies against glutathione-S-transferase and against hexahistidine.

In an alternative mode, the one of the two proteins may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when the two proteins interact. The presence of a candidate modulator compound which modulates the interaction will increase or decrease the amount of unaltered fluorescence signal of the donor.

FRET is a technique known per se in the art and thus the precise donor and acceptor molecules and the means by which they are linked to the p11 and a VGSC protein may be accomplished by reference to the literature.

The interaction between a VGSC and p11 may also be measured by fluorescence polarisation. Typically, binding partners are obtained as isolated peptides through chemical synthesis or as recombinant peptides or as purified peptides from tissue or cell sources. Full length p11 or fragments thereof may be employed in combination with VGSC peptides representing, for example, the full N-terminal cytoplasmic portion or parts thereof. For example, in the case of the rat Nav1.8 channel, a suitable fragment may comprise amino acids 53 to 127 or 75 to 102 of SEQ ID NO: 2. In the case of the rat p11 protein, suitable fragments may comprise amino acids 33 to 77 of SEQ ID NO: 4.

Either of the two peptides in the assay is labelled with a suitable label, typically a fluorescent label. The fluorescent peptide is placed in a sample tube and monochromatic light is passed through a polarizing filter onto the sample tube. The fluorophore will be excited by the polarised light bundle and the emitted light is measured. The emitted light will be scattered in all directions, because of the rotational behaviour of the small peptide in solution. This rotational behaviour changes when the peptide-interacts with its larger binding partner, resulting in retention of the polarisation and reduced scatter of the emitted light. Inhibitors will be screened by reading out the changes in rotational energy of the complex from the degree of polarisation of the emitted light.

Suitable fluorescent donor moieties are those capable of transferring fluorogenic energy to another fluorogenic molecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivatives, aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label the p11 and ER. For attachment of carbocyanine, see for example Guo et al, J. Biol. Chem., 270; 27562-8, 1995.

Rather than using fluorescence detection, it may be preferred in assay formats to detect labels and interactions using surface enhanced Raman spectroscopy (SERS), or surface enhanced resonance Raman spectroscopy (SERRS) (see e.g. WO97/05280).

An alternative assay format is a Scintillation proximity assay (SPA, Amersham Biosciences, UK). SPA uses microscopic beads containing scintillant that can be stimulated to emit light. This stimulation event only occurs when radiolabelled molecules of interest are bound to the surface of the bead. Specific bead types may be produced with different coatings for specific applications including; receptor-ligand binding, enzyme assays, radioimmunoassays, protein-protein and protein-DNA interactions.

Modulators of Interaction

For the screening methods of the invention, any compounds may be used which may have an effect on VGSC functional expression. Such an effect may, for example, be mediated by a direct effect on the channel, or indirectly by blocking or preventing the interaction between p11 and the VGSC.

In one aspect, a compound for use in downregulating functional expression of a VGSC may be a compound which binds specifically to the VGSC and/or the p11 peptide. For example, such a compound may bind to the intracellular domain of the VGSC, such as in the region of amino acids 5 to 127 or 75 to 102 of the rat Nav 1.8 sodium channel as given in SEQ ID NO: 2, or an equivalent region of a variant channel, or may bind in the region of amino acids 33 to 77 of a p11 peptide as given in SEQ ID NO: 4, or an equivalent region of a variant p11 peptide. A compound may therefore prevent binding between the VGSC and the p11 peptide and thereby prevent the enhancement of VGSC functional expression normally caused by p11.

Compounds (putative VGSC modulators) which may be used may be natural or synthetic chemical compounds used in drug screening programmes. Extracts of plants which contain several characterised or uncharacterised components may also be used. In preferred embodiments the substances may be provided e.g. as the product of a combinatorial library such as are now well known in the art (see e.g. Newton (1997) Expert Opinion Therapeutic Patents, 7(10): 1183-1194). The amount of putative modulator compound which may be added to an assay of the invention will normally be determined by trial and error depending upon the type of compound used. Typically, from about 0.01 to 100 nM concentrations of putative modulator compound may be used, for example from 0.1 to 10 nM. Modulator compounds may be those which either agonise or antagonise the interaction. Antagonists (inhibitors) of the interaction are particularly desirable.

In a further aspect, the present invention provides peptide compounds, and processes for devising and producing such compounds, which are based on the portions of the VGSC and p11 which interact with each other e.g. the regions described in the Examples below.

Modulators which are putative inhibitor compounds can be derived from the p11 and VGSC protein sequences. Peptide fragments of from 5 to 40 amino acids, for example from 6 to 10 amino acids from the region of p11 and VGSC which are responsible for the interaction between these proteins may be tested for their ability to disrupt this interaction. For example, such peptides may be derived from the intracellular domain of the VGSC such as the region of amino acids 53 to 127 or 75 to 102 of the rat Nav1.8 sodium channel as given in SEQ ID NO: 2, or from amino acids 33 to 77 of the rat p11 protein as given in SEQ ID NO: 4.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction between p11 and VGSC. A suitable antibody may bind to either the VGSC or the p11 peptide, and thereby prevent or block the interaction between these molecules.

Antibodies may be raised against specific epitopes of the VGSC or p11 peptide of the invention. For example, antibodies may be raised specifically against those regions, as described above, which are involved in the interaction between the VGSC and the p11 peptide.

For the purposes of this invention, the term "antibody", unless specified to the contrary, includes fragments which bind a VGSC or p11 peptide of the invention. Such fragments include Fv, F(ab') and F(ab')$_2$ fragments, as well as single chain is antibodies. Furthermore, the antibodies and fragment thereof may be chimeric antibodies, CDR-grafted antibodies or humanised antibodies.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

An antibody, or other compound, "specifically binds" to a protein when it binds with preferential or high affinity to the protein for which it is specific but does substantially bind not bind or binds with only low affinity to other proteins. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

In a further aspect, decreased functional expression of a VGSC may be achieved by inhibiting the expression from the VGSC gene. For example, down-regulation of expression of a target gene may be achieved using anti-sense technology or RNA interference.

In using anti-sense genes or partial gene sequences to down-regulate gene expression a nucleotide sequence is placed under the control of a promoter in a "reverse orientation" such that transcription yields RNA which is complementary to normal mRNA transcribed from the "sense" strand of the target gene. See, for example, Smith et al, (1988) Nature 334, 724-726. Such methods would use a nucleotide sequence which is complementary to the coding sequence. Further options for down regulation of gene expression include the use of ribozymes, e.g. hammerhead ribozymes, which can catalyse the site-specific cleavage of RNA, such as mRNA (see e.g. Jaeger (1997) The new world of ribozymes Curr Opin Struct Biol 7:324-335, or Gibson & Shillitoe (1997) Ribozymes: their functions and strategies form their use Mol Biotechnol 7: 242-251.)

RNA interference is based on the use of small double stranded RNA (dsRNA) duplexes known as small interfering or silencing RNAs (siRNAs). Such molecules are capable of inhibiting the expression of a target gene that they share sequence identity or homology to. Typically, the dsRNA may be introduced into cells by techniques such as microinjection or transfection. Methods of RNA interference are described in, for example, Hannon (2002) RNA Interference, Nature 418: 244-251 and Elbashir et al (2001) Duplexes of 21-nucleotide RNAs mediate RNA interference in cultured mammalian cells, Nature 411: 494-498.

Specificity of Modulation

Where any of the methods of identifying modulators of the VGSC utilizes a cell-based system, such methods may further include the step of testing the viability of the cells in the assay e.g. by use of a lactate dehydrogenase assay kit (Sigma). This step may provide an indication of any interference by the test agent of vital cellular functions.

Therapeutic Compositions and their Use

As used hereafter the term "VGSC modulator" is intended to encompass any and all of the above modulator compounds which may be identified using any of the assays or design methods of the invention. Such VGSC modulators identified by the methods of the present invention may be isolated, purified, formulated in a composition, such as a pharmaceutical composition, and/or used in therapy as described below.

VGSC modulators as described above may be provided isolated and/or purified from their natural environment, in substantially pure or homogeneous form, or free or substantially free of other materials from their source or origin. Where used herein, the term "isolated" encompasses all of these possibilities. They may optionally be labeled or conjugated to other compounds.

VGSC modulators may be useful in the treatment or prophylaxis of a wide range of is disorders. Thus in a further aspect, the present invention provides a pharmaceutical composition comprising a VGSC modulator peptide or encoding nucleic acid molecule and its use in methods of therapy or diagnosis.

In a further aspect, the present invention provides a pharmaceutical composition comprising one or more VGSC modulators as defined above and its use in methods of therapy or diagnosis.

In further aspects, the present invention provides the above VGSC modulators and nucleic acid molecules for use in the preparation of medicaments for therapy.

In one aspect, the invention includes a method of producing analgesia in a mammalian subject, which method includes administering to the subject a VGSC modulator of the present invention. Modulators of the channel may prevent transmission of impulses along sensory neurons and thereby be useful in the treatment or prevention of acute, chronic or neuropathic pain.

Acute pain is temporary, generally lasting a few seconds or longer. Acute pain usually starts suddenly and is generally a signal of rapid-onset injury to the body or intense smooth muscle activity. Acute pain can rapidly evolve into chronic pain. Chronic pain generally occurs over a longer time period such as weeks, months or years.

The VGSC modulators of the invention may be used in the treatment or prevention of acute or chronic pain, or to prevent acute pain evolving into chronic pain. Treatment of pain is intended to include any level of relief from the symptoms of pain, from a decrease in the level of pain to complete loss of the pain. Prevention includes the prevention of the onset of pain, and the prevention of the worsening of pain, for example the worsening of pain symptoms or the progression from acute pain to chronic pain.

Examples of types of chronic pain which may be treated or prevented with the VGSC modulators of the present invention include osteoarthritis, rheumatoid arthritis, neuropathic pain, cancer pain, trigeminal neuralgia, primary and secondary hyperalgesia, inflammatory pain, nociceptive pain, tabes dorsalis, phantom limb pain, spinal cord injury pain, central pain, post-herpetic pain and HIV pain, noncardiac chest pain, irritable bowel syndrome and pain associated with bowel disorders.

In a further aspect there is provided a method of preventing progression of pain in a subject at risk for developing such pain, comprising administering to the subject a VGSC modulator of the present invention.

A composition may be administered alone or in combination with other treatments (e.g. treatments having analgesic effect such as NSAIDS), either simultaneously, separately or sequentially, dependent upon the condition to be treated.

The VGSC modulators can be formulated into pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the modulators may be included in a pharmaceutical composition for formulated for slow release, such as in microcapsules formed from biocompatible polymers or in liposomal carrier systems according to methods known in the art.

For continuous release of peptides, the peptide may be covalently conjugated to a water soluble polymer, such as a polylactide or biodegradable hydrogel derived from an amphipathic block copolymer, as described in U.S. Pat. No. 5,320,840. Collagen-based matrix implants, such as described in U.S. Pat. No. 5,024,841, are also useful for sustained delivery of peptide therapeutics. Also useful, particularly or subdermal slow-release delivery to perineural regions, is a composition that includes a biodegradable polymer that is self-curing and that forms an implant in situ, after delivery in liquid form. Such a composition is described, for example in U.S. Pat. No. 5,278,202.

Peptides (for example such as those designed or discovered to inhibit the interaction of p11 and a VGSC as described above) may preferably be administered by transdermal iontophoresis. One particularly useful means for delivering compound to perineural sites is transdermal delivery. This form of delivery can be effected according to methods known in the art. Generally, transdermal delivery involves the use of a transdermal "patch" which allows for slow delivery of compound to a selected skin region. Although such patches are Generally used to provide systemic delivery of compound, in the context of the present invention, such site-directed delivery can be expected to provide increased concentration of compound in selected regions of neurite proliferation. Examples of transdermal patch delivery systems are provided by U.S. Pat. No. 4,655,766 (fluid-imbibing osmotically driven system), and U.S. Pat. No. 5,004,610 (rate controlled transdermal delivery system).

For transdermal delivery of peptides transdermal delivery may preferably be carried out using iontophoretic methods, such as described in U.S. Pat. No. 5,032,109 (electrolytic transdermal delivery system), and in U.S. Pat. No. 5,314,502 (electrically powered iontophoretic delivery device).

For transdermal delivery, it may be desirable to include permeation enhancing substances, such as fat soluble substances (e.g., aliphatic carboxylic acids, aliphatic alcohols), or water soluble substances (e.g., alkane polyols such as ethylene glycol, 1,3-propanediol, glycerol, propylene glycol, and the like). In addition, as described in U.S. Pat. No. 5,362,497, a "super water-absorbent resin" may be added to transdermal formulations to further enhance transdermal delivery. Examples of such resins include, but are not limited to, polyacrylates, saponified vinyl acetate-acrylic acid ester copolymers, cross-linked polyvinyl alcohol-maleic anhydride copolymers, saponified polyacrylonitrile graft polymers, starch acrylic acid graft polymers, and the like. Such formulations may be provided as occluded dressings to the region of interest, or may be provided in one or more of the transdermal patch configurations described above.

In yet another embodiment, the compound is administered by epidural injection. Membrane permeation enhancing means can include, for example, liposomal encapsulation of the peptide, addition of a surfactant to the composition, or addition of an ion-pairing agent. Also encompassed by the invention is a membrane permeability enhancing means that includes administering to the subject a hypertonic dosing solution effective to disrupt meningeal barriers.

The modulators can also be administered by slow infusion. This method is particularly useful, when administration is via the intrathecal or epidural routes mentioned above. Known in the art are a number of implantable or body-mountable pumps useful in delivering compound at a regulated rate. One such pump described in U.S. Pat. No. 4,619,652 is a body-mountable pump that can be used to deliver compound at a tonic flow rate or at periodic pulses. An injection site directly beneath the pump is provided to deliver compound to the area of need, for example, to the perineural region.

In other treatment methods, the modulators may be given orally or by nasal insufflation, according to methods known in the art. For administration of peptides, it may be desirable to incorporate such peptides into microcapsules suitable for oral or nasal delivery, according to methods known in the art.

Whether it is a peptide, antibody, nucleic acid molecule, small molecule or other pharmaceutically-useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Instead of administering these agents directly, they could be produced in the target cells by expression from an encoding gene introduced into the cells, e.g. in a viral vector (a variant of the VDEPT technique—see below). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO90/07936).

The expression of p11 in an organism may be correlated with the functional expression of a VGSC in the organism, and this correlation may form the basis of diagnosis of diseases related to inappropriate VGSC expression.

The invention will now be further described with reference to the following non-limiting Figures and Examples. Other embodiments of the invention will occur to those skilled in the art in the light of these. Any reference mentioned herein, inasmuch as it may be required to supplement the common general knowledge of the person skilled in the art in practicing the invention, is specifically incorporated herein by reference in its entirety.

EXAMPLES

Materials and Methods

Yeast Two-Hybrid Screen

A two-hybrid interaction screen was performed with the N-terminal intracellular domain (amino-acid position 1-127) of $Na_v1.8$ and a rat PI DRG cDNA library as described[11]. The bait plasmid was generated by PCR with rat $Na_v1.8$ cDNA as a template with a forward primer (5'-gcgaattcatggagctccctttg-3'; SEQ ID NO: 9) and a reverse primer (5'-tatagcggccgctttgatggctgttcttc-3'; SEQ ID NO: 10). The amplified fragment was ligated into pEG202 at EcoRI-NotI sites as an in-frame fusion with the LexA-DNA binding domain.

A cDNA library from postnatal day 1 dorsal root ganglia (DRG) was generated[11]. The DRG library cDNAs were expressed as in-frame fusions with the Gal4 transcriptional activation domain. Approximately $5 \times 10^6$ yeast transformants were screened for β-galactosidase activity and growth in the absence of leucine, and five identical positive clones encoding a full length p11 were identified. The clone included a 51 bp 5'-UTR, a 288 bp coding region, and a 450 bp 3'-UTR of the rat p11 gene. To verify that p11 interacts specifically with the N-terminal intracellular domain of $Na_v1.8$, the rescued p11-encoding plasmid DNA was re-introduced into other strains of yeast containing different intracellular domains of $Na_v1.8$ as baits. Direct interaction between p11 and N-terminal domain of $Na_v1.8$ in vitro was assessed using GST pull down assays[12]. Fuller details of experimental methods are present in supplementary information.

GST Pull-Down Assay

The segment encoding the N-terminus of rat $Na_v1.8$ (amino acid position 1-127) was amplified by PCR and cloned in-frame into the EcoRI/NotI sites of pGEX-5X-1 (Amersham Pharmacia Biotech). The $GST/Na_v1.8$ N-terminus fusion protein, designated as GST-SNS(I), was produced in E. coli BL-21 and affinity purified on glutathione-sepharose beads. Original pGEX-5X-1 was used to produce GST control protein.

Full length rat cDNA for p11 in yeast expression vector pJG4-5 was subcloned as the NcoI-XbaI fragment into the pBS500 expression vector which results in GFP-p11 fusion protein expression driven by elongation factor 2 cc promoter. The resultant plasmid was designated as pBS-GFP/p11. COS-7 cells were transfected with pBS-GFP/p11 by lipofection. GFP-p11 fusion protein was extracted from transfected COS-7 cells by lysis buffer (4% SDS, 10 mM sodium phosphate, pH 7.4) 3 days after transfection. The lysate was centrifuged at 10,000 rpm at 4° C. for 10 mins. The supernatant was retained and centrifuged at 14,000 rpm at 4° C. for 30 min. The supernatant was then transferred to a macrosep 30K omega centrifugal concentrator (Pall Filtron) and 10 ml ice-cold Phosphate Buffered Saline (PBS), pH 7.4, was added. It was centrifuged at 5,000 rpm for 2 hours. The filtrate was discarded and the residue, containing the solubilized protein, was used in the pull-down assay experiment. GFP expression plasmid, pBS-GFP, was used for production of GFP protein for a negative control.

To examine the binding of p11 to the N-terminus of $Na_v1.8$ in vitro, glutathione-sepharose beads pre-incubated with purified GST, serving as control, or GST-SNS(I) were incubated at 4° C. overnight with GFP-p11 fusion protein or GFP protein extracted from transfected COS cells in PBS. After intensive washing with ice-cold PBS, the bound proteins were denatured in sample buffer (100 mM Tris-HCl pH 6.8, 4% SDS, 0.2% Bromophenol Blue, 20% Glycerol. 200 mM DDT), separated by 10% SDS-PAGE, and transferred to nitrocellulose membrane (Hybond ECL; Amersham Pharmacia Biotech). The membrane was blocked for 1 h in 5% nonfat dry milk in PBS-T at room temperature (0.1% Tween-20 in PBS, pH7.4). Primary anti-GFP antibody (Santa Cruz Biotechnology) in 1:800 dilution was applied for 1 hr at room temperature. Secondary antibody (horseradish peroxidase-conjugated sheep anti-mouse IgG, Amersham Pharmacia Biotech) in 1:2000 dilution was applied for 1 hr at room temperature. ECL Western Blotting Detection Reagents (Amersham Pharmacia Biotech) was applied according to the manufacturer's instructions and the blot was exposed to BioMax film (Kodak).

Northern Blot Analysis

Total RNA was isolated from various rat tissues by acid guanidinium thiocyanate-phenol-chloroform extraction method[16] and fractioned by electrophoresis on 1.5% agarose gel in 10 mM phosphate buffer (pH 6.5) after glyoxylation. RNA was blotted onto hybond $N^+$ nylon membrane in 20×SSC solution for 6 hours and fixed by UV irradiation. The membrane was stained with methylene blue to confirm even recoveries of RNA. Thereafter, the membrane was prehybridized and hybridized with $^{32}P$-labeled p11 DNA probe (50 ng, specific activity $2 \times 10^9$ c.p.m. per μg DNA) at 43° C. in hybridization buffer (50% formamide, 6×SSC, 50 mM $NaH_2PO_4$, 1 mM EDTA, 1% SDS, 2.5×Denhardt's solution, 250 μg herring sperm DNA, pH 6.5) for 18 hrs. The $^{32}P$-labeled p11 DNA probe was generated from 284 bp PCR fragment of p11 (amino acid position 3-127) using Klenow enzyme and random primer in the presence of $[\alpha-^{32}P]$ ATP at 37° C. for 15 min. Unincorporated nucleotides were removed using the QIA quick nucleotide removal kit (Qiagen). Hybridized membrane was washed with 0.2×SSC/0.1% SDS at 53° C. and exposed to BioMax film (Kodak) at −70° C.

RT-PCR

DRG neurons from 2 weeks old rats were cultured in DMEM containing 3.3 ng/ml aphidicoline for 7 days. Cultures were supplemented with NGF (50 ng/ml) or grown in the absence of NGF and in the presence of rabbit anti-NGF antiserum. Total RNA extracted from the culture was treated with DNase I and cDNA was synthesized with Superscript using randam hexamer. PCR (94° C., 1 min; 58° C., 1 min 30 sec; 72° C., 1 min 30 sec; 50 µl) was started with the primer pair specific for p11 (284 bp), 5'-CATCCCAA ATGGAG-CATG-3' (SEQ ID NO:11), 5'-CTACTTCTTCTGCTTCAT-GTGTACTAC-3' (SEQ ID NO:12). After 2 cycles, the primer pair for CGRP (222 bp), 5'-GGTGTGGTGA AGGACAAC-3' (SEQ ID NO:13), 5'-CATAGGGAGAAGGGTTTC-3' (SEQ ID NO:14) was added. In separate tubes, PCR was started with the primer pair for CGRP, and the primer pair for cyclophilin (300 bp), 5'-ACCCCACCGTGTTCTTCGAC-3' (SEQ ID NO:15), 5'-CATTTGCCATGGACAAGATG-3' (SEQ ID NO:16), were added to the reaction 3 cycles after the start. Ten µl of the PCR solution was collected every 3 cycles and applied for 1.5% agarose gel electrophoresis and the PCR products were visualized by ethidium bromide. The intensity of each band was analyzed using NIH Image program and plotted. The linear range of amplification (p11, 32-38 cycles; CGRP, 30-36 cycles; cyclophilin 27-33 cycles) has been identified. The midpoint of this range (p11, 35 cycles; CGRP, 33 cycles; cyclophilin, 30 cycles) were used for the RT-PCR experiments and 1 µl of the reverse transcribed solutions was used for PCR.

Immunofluorescence Analysis

A stably transformed CHO cell line (CHO-SNS22 cells) that expresses rat $Na_v1.8$ protein in the cytosol was transfected with the expression plasmid pBS-GFP/p11 by lipofection. The CHO-SNS22 cell line was kept in Nutrient Mixture F-12 (Ham) medium (GibcoBRL) with 2.5% fetal bovine serum and 1 mg/ml Geneticin G418 sulphate. One day prior to transfection, cells were subcultured and plated in 35 mm dish containing F-12 medium with 0.5% fetal bovine serum and 1 mg/ml G41S. Prior to transfection, cells in 35 mm dish were rinsed twice with serum-free F-12 medium. 1.1 µg of DNA was mixed with 5 µl of Lipofectamine (GibcoBRL) and incubated at room temperature for 30 min. The mixture was added to the pre-rinsed cells and incubated at 37° C. for 2 hours. DNA/lipofectamine mixture was replaced with F-12 medium with 0.5% fetal bovine serum and 1 mg/ml G418 after 2 hours. Three days after transfection, the cells were fixed with 4% paraformaldehyde for 15 min on ice and subsequently incubated with anti-SNS polyclonal antibody (SNS11). The cells were washed with PBS and incubated with rhodamine-labelled anti-rabbit IgG before analysis with a confocal microscope.

In Situ Hybridisation

A 284 bp p11 PCR fragment was subcloned into pGEM-T Easy (Promega), and DIG-UTP labelled sense or antisense cRNA probe were generated using T7 RNA polymerase for in situ hybridisation studies. Frozen DRG sections (10 µm thick) were fixed for 15 min in 4% paraformaldehyde on ice and were acetylated in 0.1M triethanolamine, 0.25% acetic anhydride for 10 min. Prehybridization was carried out in 50% formamide, 4×SSC, 100 µg/ml herring sperm DNA, 50 µg/ml tRNA, 2×Denhardt's solution at room temperature for 1 hr. Hybridization was carried out in the same buffer containing 50 ng/ml cRNA probe at 65° C. for 16 hrs. Sections were washed in 0.1×SSC at 72° C. and incubated with alkaline phosphatase conjugated anti-digoxygenin antibody (Roche). The same sections were then stained with anti-$Na_v1.8$ polyclonal antibody (SNS11) followed by rhodamine-conjugated anti-rabbit IgG antibody.

NGF Regulation of p11

DRG neurons from 2 week old rats were cultured with NGF (50 ng/ml) or grown in the absence of NGF and in the presence of rabbit anti-NGF antiserum. Total RNA extracted from the culture was treated with DNase I and cDNA was synthesized with Superscript using randam hexamer. PCR was performed with the primer pair specific for p11 (284 bp), 5'-CATCCCAAATGGAGCATG-3' (SEQ ID NO:17), 5'-CTACTTCTTCTGCTTC ATGTGTACTAC-3' (SEQ ID NO:18).

Transfection and Extraction of p11 in COS-7 Cells

COS-7 cells were transiently transfected with 20 µg of pBS-GFP/p11 by lipofection. Three days after the transfection, the cells were incubated in the lysis buffer (150 mM NaCl, 1% NP-40, 0.5% DOC, 0.1% SDS, 50 mM Tris, pH 7.5) for 30 min on ice. The lysis buffer was centrifuged for 30 min at 10,000 g at 4° C. The supernatant was used for in vitro binding assay. GFP expression plasmid, pBS-GFP, was used for production of GFP protein as a negative control.

Expression of GST-SNS Sodium Channel Fusion Protein cDNA for $NH_2$-terminal intracellular domain of rat SNS sodium channel was amplified by PCR using primers 5'-GGAATTCATGGAGCTCCCCTTTGCG-3' (SEQ ID NO:19) and 5'-AATTGCGGCCGCAGACGCTTTGATG-GCTGT-3' (SEQ ID NO:20). The amplified fragment, corresponds to the amino acid position 1 to 127 of rat SNS sodium channel protein, was cloned into EcoRI/NotI sites in GST gene fusion vector pGEX-5X-1. The resultant expression vector coding GST/SNS sodium channel $NH_2$-terminal fusion protein was designated as pGEX-5X-1-SNS(I). pGEX-5X-1-SNS(I) was transformed into E. coli strain BL21, subsequently GST/SNS(I) fusion protein was affinity purified on glutathione-Sepharose beads. The glutathione-Sepharose/GST/SNS sodium channel complex was incubated with the extract obtained from COS-7 cells transfected with pBS-GFP/p11 in binding buffer (10% glycerol, 1 mM $MgCl_2$, 100 mM KCl, 0.5 mg/ml bovine serum albumin, 10 mM Tris, pH7.9) for 4 hr at 4° C. The bound proteins were denatured in sample buffer and separated by 12% SDS-PAGE. The GFP/SNS sodium channel(I) fusion protein was detected by immunoblotting with anti-HA antibody whose epitope tag is situated in the junction between GFP and SNS sodium channel $NH_2$-terminal protein. pGEX-SX-1 was used for production of GST protein as a negative control.

Electrophysiology

Membrane currents were recorded from CHO-SNS 22 cells using the whole-cell patch-clamp technique. The extracellular recording solution contained the following (in mM): NaCl (140), TEA Cl (10) HEPES (10), $CaCl_2$ (2.1), $MgCl_2$ (2.12), 4-aminopyridine (4-AP) (0.5), KCl (7.5), tetrodotoxin (TTX) (250 nM). The solution was buffered to pH 7.2-3 with the addition of NaOH. The intracellular solution contained the following (in mM): CsCl (145), EGTA Na (3 (6)), Hepes (10), $CaCl_2$, (1.21), $MgCl_2$ (1.21), TEA Cl (10) and was buffered to pH 7.2-3 with the addition of CsOH. For recordings from neurons the extracellular solution was the same, except that NaCl was reduced to 43.3 mM with equivalent replacement of TEA-Cl and the addition of 20 µM CdCl2. In the intracellular recording solution, 10% of the CsCl was replaced by CsF, the MgCl2 replaced by 3 mM ATP (Mg) and the solution contained 500 mM GTP (Li) Chemicals were either 'AnalaR' (BDH, Merk Ltd.) or supplied by Sigma.

Chemicals were either 'AnalaR' (BDH, Merk Ltd., Lutterworth, Leicestershire, UK.), or supplied by Sigma (Poole, Dorset, UK). TTX was obtained from Alomone labs (TCS Biologicals, Botolph Claydon, Bucks, UK). A minority of CHO-SNS 22 cells generate an endogenous tetrodotoxin-sensitive (TTX-s) $Na^+$ current (personal observation) which was eliminated from all recordings by including 250 mM TTX in the extracellular media. No inward currents were recorded in non-transfected cells under these circumstances.

Electrodes were fabricated from thin-wall glass capillaries (GC150TF-10; Harvard apparatus, Edenbridge, Kent, UK), and had an access resistance of 2-4 MΩ when filled with recording solution. Recordings were made using an Axopatch 200B patch-clamp amplifier (Axon Instruments, Foster City, Calif., USA). Pulse protocols were generated and data stored to disk using pClamp6 software (Axon Instruments), running on a PC. CHO-SNS 22 cells were held at −90 mV. Voltage-clamp protocols incorporated a negative pre-pulse to −110 mV, and the cell was subsequently stepped to more depolarized potentials for 50 ms (up to a final value of +80 mV), in 10 mV increments.

All experiments were performed at room temperature.

Antisense Studies

The 309 bp NcoI fragment of p11 was cloned in 3' to 5' direction into Nco-I restriction site in pBS500 vector resulted in a expression system for a sense-GFP/antisense-p11 fusion RNA, pBS-GFP/AS(p11). 400 μg/ml of pBS-GFP/AS(p11) together with 0.5% Texas Red in injection buffer (118 mM KCl, 5 nM Hepes, 22.2 mM $NaHCO_3$, 1.2 mM $MgCl_2$, pH 7) were injected into nuclei of 2 week old rats DRG small diameter neurons using Eppendorf microinjector. During the injection, the DMEM was replaced by a calcium free buffer (PBS and containing 10 mM glucose and 2.4 mM $MgCl_2$). After completion of the injections, the calcium free buffer is replaced by DMEM containing 3.3 ng/ml aphidicolin and the neurons were incubated for 3 days at 37° C. in $CO_2$ incubator prior to electrophysiology recordings.

Immunofluorescence analysis showed that injection of antisense p11 resulted in a loss of immunoreactive p11 compared to uninjected cells.

Molecular Cloning of N-Terminus $Na_V1.8$ for Binding Assay to p11 cDNA of the $Na_v1.8$'s N-terminus of a-subunit was cut into three fragments and cloned into pGEX-5X-1 vector (Amersham). The resulting constructs were named N1 (amino acids 1-25), N2 (a.a 26-50), and N3 (a.a 51-127). The primers used were designed to introduce an EcoRI restriction enzyme cut site in the 5' direction and NotI in the 3' direction.

Forward primers:

SNS I-F, 5'-5'-G<u>GAATTC</u>ATGGAGCTCCCCTTTGCG-31 (SEQ ID NO:21)

SNS I(N2)-F, 5'-G<u>GAATTC</u>AAGCAGATTGCTGCTCACCGC-3' (SEQ ID NO:22)

SNS I(N3)-F, 5'-G<u>GAATTC</u>CCCAGGCCTCAGCTGGACTTG-3' (SEQ ID NO:23)

Reverse primers:

SNS I(N1)-R, 5'-AATTGCGGCCGCCTCGATCTCTGCCAGTGACTC-3' (SEQ ID NO:24)

SNS I(N2)-R, 5'-AATTGCGGCCGCCTTCTCGCCCTTGTCCTCCTG-3' (SEQ ID NO:25)

SNS I-R, 5'-AATTGCGGCCGCAGACGCTTTGATGGCTGT-3' (SEQ ID NO:26)

EcoRI sites are underlined. NotI sites are boldfaced. PCR was carried out using SNS I-F/SNS I(N1)-R, SNS I(N2)-F/SNS I(N2)-R, SNS I (N3)-F/I-R primer pairs for N1, N2, and N3 fragments respectively. The following cycles were used: 25 cycles of 1 min at 94° C., followed by 1 min 30 sec at 55° C., and then 1 min 30 sec at 72° C. PCR products were digested with EcoRI and NotI and ligated into linearized pGEX-5X-1 vector. The resulting constructs were sequenced with forward primer 5'pGEX (5'-GGGCTGGCAA GCCACGTTTGGTG-3'. SEQ ID NO:27) and reverse primer 3'pGEX (5'-CCGGGAGCT GCATGTGTCAGAGG-3', SEQ ID NO:28).

The N3 fragment was further cut into three smaller fragments to elucidate the exact binding site on $Na_v1.8$ intracellular loop I after GST pulldown assay has shown that p11 binds specifically to N3. The three fragments, named N3-1 (a.a 51-73), N3-2 (a.a 74-103) and N3-3 (a.a 104-127) were cloned into pGEX-SX-1 vector as described above.

Forward primers:

N3-1-5',5'-G<u>GAATTC</u>CCCAGGCCTCAGCTGGACTTG-3' (SEQ ID NO:29)

N3-2-5',5'-G<u>GAATTC</u>CTGGTCGGGGAGCCCCTGGAG-3' (SEQ ID NO:30)

N3-3-5',5'-G<u>GAATTC</u>TTCAGTGCCACTTGGGCC-3' (SEQ ID NO:31)

Reverse primers:

N3-1-3',5'-AATTGCGGCCGCTTCTGCTGGGAGCTC-3' (SEQ ID NO:32)

N3-2-3',5'-AATTGCGGCCGCTCTGGAAATGGTCCTGCT-3' (SEQ ID NO:33)

PCR was carried out using N3-1-5'/N3-1-3', N3-2-5'/N3-2-3', N3-3-5'/I-R primer sets for N3-1, N3-2, and N303 respectively. The same PCR cycles were used as described above.

Example 1

Identification of a Protein that Interacts with Rat Nav1.8

A rat sensory neuron cDNA library[11] was used to screen for proteins that interact with the N-terminal intracellular domain of rat $Na_v1.8$. Five identical positive clones encoding a full length p11 were identified through their interaction with the N-terminus of $Na_v1.8$. To test whether p11 binds to the N-terminal intracellular domain of $Na_v1.8$ in vitro, we expressed the GFP-p11 fusion protein in COS-7 cells, and expressed the N-terminal domain of $Na_v1.8$ as a GST fusion protein, GST-SNS(I). The COS cell lysates were incubated with affinity-purified GST and GST-SNS(I), the N-terminal domain of $Na_v1.8$ fused to GST, immobilized on glutathione-sepharose beads and were examined by immunoblotting with anti-GFP antibodies. Purified GST or GST/SNS (I) did not pull down GFP protein. Purified GST did not pull down GFP/SNS (I), while GST/p11 efficiently pulled down the GFP/SNS (I) fusion protein. These data demonstrate that p11 binds directly to the $NH_2$-terminal of SNS sodium channel.

We examined the tissue distribution of the p11 transcript. Northern blot analysis showed high levels of expression of p11 mRNA in DRG, modest expression in heart and liver, and weak expression in brain isolated from 2 weeks old rats. RT-PCR showed a dramatic increase of p11 mRNA in cultured rat DRG neurons treated with nerve growth factor (NGF) which is known to cause decreases in thermal, chemical and mechanical thresholds of pain perception in animal models[13, 14]. In situ hybridization was performed on a section of 2 weeks old rat DRG. An antisense p11 probe demonstrated strong staining in both small and large diameter neurons. Combined immunohistochemistry with anti-Na$_v$1.8 polyclonal antibody SNS11[15] showed that most (>98%) of the Na$_v$1.8 positive cells also expressed p11 mRNA.

Example 2 p11 Regulates Translocation of SNS Sodium Channel into Plasma Membrane

CHO-SNS 22 cells are stably transfected cell line with rat SNS sodium channel cDNA. They do not have SNS sodium channel current however they express high amount of full length SNS sodium channel mRNA. Immunocytochemical study using anti-SNS sodium channel polyclonal antibody (SNS 11) showed SNS sodium channel-like immunoreactivity in cytosol of CHO-SNS 22 cells but not in the plasma membrane. To study whether p11 changes the cellular localization of SNS sodium channel protein, we transfected CHO-SNS 22 cells with GFP/p11 fusion cDNA (pBS-GFP/p11). The p11 expression was detected as green fluorescence signal due to fused GFP. The green fluorescence specifically localized in the plasma membrane. In the same cell, SNS sodium channel-like immunoreactivity, red fluorescence, also shows signal in the plasma membrane as well as cytosol. Co-expression of p11 and SNS sodium channel was seen in the plasma membrane. Densitometric analysis of Na$_v$1.8-like immunoreactivity of the GFP-p11 fusion or GFP protein expressed CHO-SNS22 cells showed that 16.5% (S.E.M. 1.2, n=30) of Na$_v$1.8-like immunoreactivity moved to the plasma membrane fraction after the expression of GFP-p11 fusion protein, while only 4.3% (S.E.M. 0.4, n=30) of Na$_v$1.8-like immunoreactivity localized on the plasma membrane in the GFP expressing CHO-SNS22 cells. These data demonstrate that p11 promotes the translocation of Na$_v$1.8 protein to the extracellular membrane.

Example 3 p11 Induces SNS Sodium Channel Current in CHO-SNS 22 Cells

In 9 from a total of 42 CHO-SNS 22 cells transfected with pBS-GFP/p11, TTX-resistant (TTX-r) currents were found that resembled neuronal SNS sodium channel current. The currents very closely resembled the SNS sodium channel Na$^+$ current recorded from transfected COS cells, both in terms of voltage-dependence and kinetics. The TTX-r inward currents are shown in FIG. 1A. The current began to activate around 0 to +10 mV, and peaked at +40 mV (FIG. 1B). The reversal potential for the currents is quite close to the theoretical reversal potential for Na$^+$ (+81 mV), consistent with them being Na$^+$ currents. Any apparent deviation from the theoretical value may be considered within experimental error, given the small size of the inward current and the often non-linear current-voltage relations of CHO cells. No TTX-r inward currents have ever been recorded before from either non-transfected (n=41) or GFP transfected (n=40) CHO-SNS22 cells, following p11 transfection a little over 20% of the cells generated small Na currents. This is a highly statistically significant finding (P<0.002 vs. GFP transfected or control non-transfected, Fisher exact test). This suggests that p11 may be a protein necessary for SNS sodium channel Na$^+$ channel function, normally missing from the CHO cell.

Nerve growth factor (NGF) is known as a potent hyperalgesic mediator[5]. On the basis of the results shown herein i.e. the involvement of p11 on the trafficking of SNS sodium channel protein into plasma membrane, it appears that the known function of NGF as a hyperalgesic mediator may be due to up-regulation of p11[7] and subsequent membrane translocation of SNS sodium channel by p11 (without altering the amount of SNS sodium channel mRNA[6]).

Prostaglandins such as prostaglandin E2 (PGE$_2$) act as hyperalgesic agents and its generation depends on cyclooxygenase (COX)-catalyzed conversion of arachidonic acid. The liberation of arachidonic acid from membrane glycerophospholipids is mediated by the hydrolytic action of phospholipase A2 and this is the rate-limiting step in the generation of prostaglandins. p11 is also known as an endogenous inhibitor for cytosolic phospholipase A2 (cPLA2)[8]. Transforming growth factor-α (TGF-α) has been shown to stimulate expression of COX-2, cPLA2, and p11 in an epithelial cell line[9]. This suggests the expression of positive (COX-2, cPLA2) and negative (p11) regulator for prostaglandin synthesis is controlled by a common mechanism. Interestingly, calpactin-I heavy chain has antiflammin-like sequence which share a core tetrapeptide KVXD. Antiflammins are a peptides that share a common sequence with uteroglobin and lipocortin-I, which may act as anti-inflammatory agent by suppressing leukocyte trafficking to the lesion[10] however their activity in inflammation in vivo is still controversial.

Example 4

Effect of p11 Antisense on Nav1.8 Channels

Figure 2:
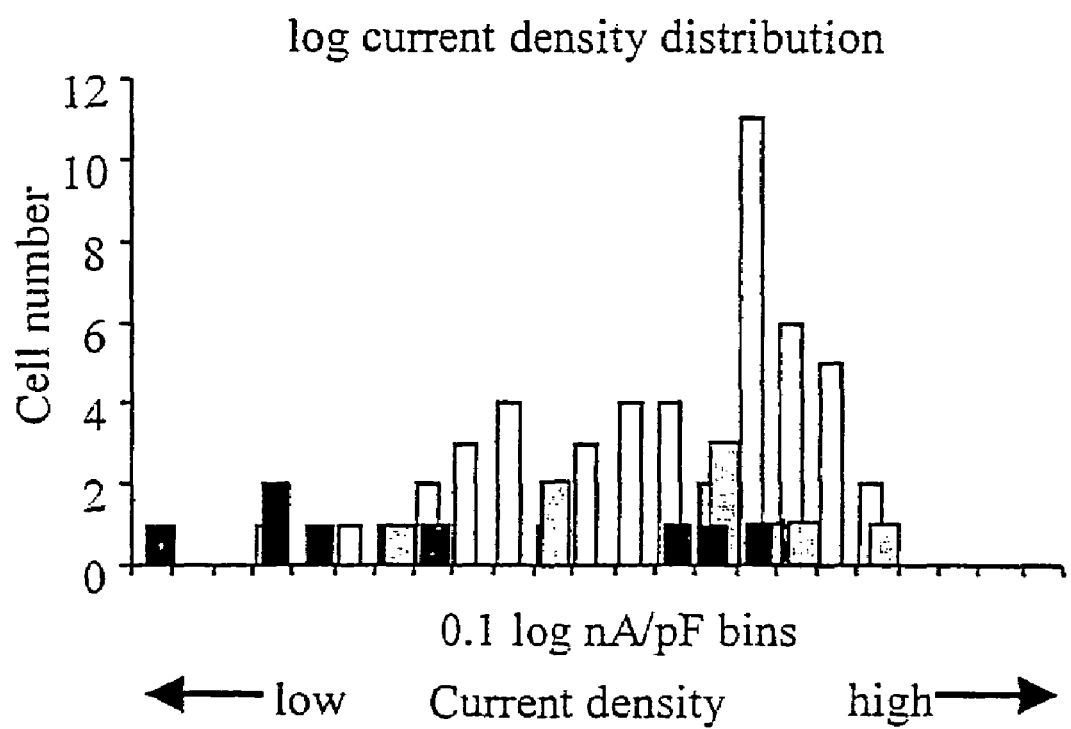
FIG. 2: p11 antisense mRNA expression in DRG neurons caused a loss of Nav1.8 current density. The histogram shows cell number against log [current density] for control and cDNA-injected neurons. White bars=non-injected control cells; grey bars=GFP-injected cells; Black bars=p11 antisense and GFP-injected cells. Two-tailed unpaired t-test for the log [current density] of neurons injected with GFP expression vector only and p11 antisense mRNA expression vector showed is significant reduction in Nav1.8 current (P<0.02, Student's two-tailed t-test).

To test the possible regulatory role of p11 on Na$_v$1.8 channels in sensory neurons, we microinjected the p11 antisense expression vector, pBS-GFP/AS(p11), into the nuclei of DRG neurons in culture. Immunohistochemistry, using anti-p11 polyclonal antibodies confirmed an efficient reduction of p11-like immunoreactivity in DRG neurons by the introduction of pBS-GFP/AS(p11). The introduction of pBS-GFP/AS (p11) also caused a dramatic loss of Na$_v$1.8 current (FIG. 2). The mean peak Na$^+$ current density was reduced in pBS-GFP/AS(p11) injected neurons (63.1+/−24.5 pA/pF, mean+/−S.E.M. n=8) when compared with control neurons injected with GFP only (179.2+/−40.3 pA/pF, n=9, P<0.04; Student's two tailed t-test). In contrast, the residual maximum K$^+$ current density derived from currents recorded on stepping to +80 mV were not significantly affected by pBS-GFP/AS (p11) (61.7+/−17.6 pA/pF in control cells vs. 44.8+/−5.5 pA/pF in injected, (means±S.E.M., P=0.4; Student's two tailed t-test), suggesting that the affect of antisense was specific. We also examined the affect of pBS-GFP/AS/p11 on TTX-sensitive currents in ND7/23 cells. TTX-sensitive current densities were unaffected (p>0.1) Students unpaired two-tailed t-test), suggesting that p11 is not required for the expression of other TTX-sensitive sodium channel subtypes.

The present inventors have demonstrated that the functional expression of the TTX-insensitive VGSC Nav 1.8 (which hereinafter may be referred to as the "SNS sodium channel") is facilitated by interaction with a second protein— p11. This improved function appears to be effected through direct protein-protein interaction.

Example 5

Molecular Cloning of p11 to Elucidate Binding Domain to Na$_v$1.8 p11 was initially divided into three fragments (amino acids 1-32, a.a 33-77, and a.a 78-95) and cloned into pBS500 expression vector. The primers used were designed to introduce a NcoI restriction enzyme cut site in the 5' direction and XbaI in the 3' direction.

Forward primers: p11-5',5'-AA<u>CCATGG</u>ATGCCATCCCAAATG-3' (SEQ ID NO:35);

p11-2-5',5'-AA<u>CCATGG</u>GTGCTCATGGAAAG-3' (SEQ ID NO:36);

p11-3-5',5'-AA<u>CCATGG</u>GGGCTCATCATTG-3' (SEQ ID NO:37).

Reverse primers: p11-1-3',5'-GATCTAGATCTCAGGTCCTCCTTTGTC-3' (SEQ ID NO:38);

p11-2-3',5'-GATCTAGACGCCACTAGTGATAGAAAGC-3' (SEQ ID NO:39);

p11-3-3',5'-GATCTAGACTACTTCTTCTGCTTCATGTGTAC-3' (SEQ ID NO:40).

NcoI sites are underlined. XbaI sites are boldfaced. PCR was carried out using p11-5'/p11-1-3', p11-2-5'/p11-2-3', p11-3-5'/p11-3-3" primer sets for fragments N3-1, N3-2, and N3-3 respectively. The following cycles were used: 25 cycles of 1 min at 94° C., followed by 1 min 30 sec at 55° C., and then 1 min 30 sec at 72° C. PCR products were digested with restriction enzymes EcoRI and NotI and ligated into pre-linearized pBS500 vector. The resulting constructs were sequenced with forward primer GFP5 (5'-ACCACATGGTCCTTCTTGAG-3', SEQ ID NO:41) and reverse primer CSF-R (5'-TGCTGTTTAAATATTAAACAGGG-3', SEQ ID NO:42).

The p11-2 fragment was further cut into two smaller fragments (amino acids 33-51 and 52-77) and cloned into pBS500 expression vector as described above. Forward primers: p11-2-2F, 5'-AA<u>CCATGG</u>GTGGACAAAATAATGAAAGAC-3' (SEQ ID NO:43); p11-2-5'. Reverse primers: p11-2-3'; p11-2-1R, 5'-GATCTAGAAGCCAGAGGGTCCTTTTGA-3' (SEQ ID NO:44). PCR was carried out using p11-2-5'/p1-2-1R and p11-2-2F/p11-2-3' primer sets for fragment p11-2-1 and p11-2-2 respectively. Another fragment p11-1A (amino acids 1-51) was also cloned using the primer set p11-5' and p11-2-1R.

GFP/p11 fusion protein was expressed in COS-7 cells by transient transfection. The Na$_v$1.8 N-terminal region was truncated into three separate fragments, fused to GST, immobilized on glutathione-sepharose beads and were examined by immunoblotting with anti-GFP antibodies. GFP/p11 binds directly to N3 region (aa 53-127). Purified GST-N1 and GST-N2 did not pull down GFP/p11 nor did GST control bind to GFP/p11.

GFP and GFP/p11 fusion protein were expressed in COS-7 cells by transient transfection. The COS cell lysates were incubated with affinity-purified GST-N3-1, -N3-2, and -N3-3 fragments of the N-terminal domain of Na$_v$1.8 fused to GST, immobilized on glutathione-sepharose beads and were examined by immunoblotting with anti-GFP antibodies. Purified GST-N3-1 and GST-N3-3 did not pull down GFP/p11, while GST-N3-2 efficiently pulled down the GFP/p11 fusion protein (amino acids 75-102).

GFP/p11-1, -2, -3 fusion protein were expressed in COS-7 cells by transient transfection. The COS cell lysates were incubated with affinity-purified GST-SNS(I), the N-terminal domain of Na$_v$1.8 fused to GST, immobilized on glutathione-sepharose beads and were examined by immunoblotting with anti-GFP antibodies. GST-SNS(I) did not pull down cell lysates p11-1 and p11-3, but it efficiently pulled down cell lysate p11-2 (amino acids 33-77).

GFP/p11-1A, p11-2, p11-2-1, and p11-2-2 fusion proteins were expressed in COS-7 cells by transient transfection. The COS cell lysates were incubated with affinity-purified GST-SNS(I), the N-terminal domain of Na$_v$1.8 fused to GST, immobilized on glutathione-sepharose beads and were examined by immunoblotting with anti-GFP antibodies. GST-SNS (I) did not pull down cell lysates p11-1A, p11-2-1, nor p11-2-2. These protein fragments correspond to amino acids 1-51, 33-51, 52-77 respectively. GST-SNS(I) efficiently pulled down cell lysate p11-2.

Example 6

Mutagenesis of p11 Mutated-EF Hand

To delineate residues that are important for p11 to bind to Na$_v$1.8, point mutations were generated in the p11 EF hand binding region of construct p11-2. The oligonucleotide-directed point mutation was made by a two-step polymerase chain reaction protocol using two mutagenic primers and two restriction site primers. Full-length p11 in pBS500 expression vector was used as template. The following primer sets were used to introduce mutation 1 in amino acids 56 to 60 (from amino acid sequence DQCRD, SEQ ID NO:45, to AQARA, SEQ ID NO:46): p11-5'/p11-mutation1-R; p11-3'/p11-mutation1-F. Forward primers: p11-5',5'-AACCATGGATGCCATCCCAAATG-3' (SEQ ID NO:47); p11-mutation1-F, 5'-GGCCCAGGCCCGAGCTG-3' (SEQ ID NO:48). Reverse primers: p11-3',5'-GATCTAGACTACTTCTTCTGCTTCATGTGTAC-3' (SEQ ID NO:49); p11-mutation1-R, 5'-TCCAGCTCGGGCCTGGGCC-3' (SEQ ID NO:50). PCR cycles: 35 cycles of 94° C. 1 min, 63° C. 1 min 30 sec, 72° C. 1 min 30 sec.

The following primer sets were used to introduce mutation 2 in amino acids 62 to 67 (from amino acid sequence KVGFQS, SEQ ID NO:51, to AVAFQA, SEQ ID NO:52) in p11: p11-5'/p11-mutation2-R; p11-3'/p11-mutation2-F. Forward primer: p11-mutation2-F, 5'-GAGCAGTGGCCTTCCAGGCCT-3' (SEQ ID NO:53). Reverse primer: p11-mutation2-R, 5'-TAGAAAGGCCTGGAAGGCCACTGCT-3' (SEQ ID NO:54). PCR cycles: 40 cycles of 94° C. 1 min, 60° C. 1 min 30 sec, 72° C. 1 min 30 sec.

The two PCR products containing the mutations were subcloned into pBS500 expression vector at NcoI/XbaI sites. Incorporation of the mutation was confirmed by DNA sequencing using the forward primer GFP5',5'-ACCACATGGTCCTTCTTGAG-3' (SEQ ID NO:55).

In summary, the data presented here show that the p11 is responsible for translocation of SNS sodium channel protein into plasma membrane and is a necessary permissive factor for SNS sodium channel function. Therefore the interaction between p11 and SNS sodium channel can provide a target for therapeutic intervention in pain states.

REFERENCES

1. Fitzgerald, E. M., Okuse, K., Wood, J. N., Dolphin, A. C., Moss, S. J. (1999) cAMP-dependent phosphorylation of the tetrodotoxin-resistant voltage-dependent sodium channel SNS sodium channel. *J. Physiology* 516 433-446.
2. Waisman, D. M. (1995) Annexin II tetramer: structure and function., *Mol. Cell. Biochem.* 149/150, 301-322.
3. Rety, S., Sopkova, J., Renouard, M., Osterloh, D., Gerke, V., Tabaries, S., Russo-Marie, F., Lewit-Bentley, A. (1999) The crystal structure of a complex of p11 with the annexin II N-terminal peptide., *Nat. Struct. Biol.* 6(1), 89-95.
4. Osborn, M., Johnsson, N., Wehland, J., Weber, K. (1988) The submembranous location of p11 and its interaction with the p36 substrate of pp60$^{src}$ kinase in situ., *Exp. Cell. Res.* 175(1), 81-96.
5. McMahon, S. B., Bennet, D. L., Priestley, J. V., Shelton, D. L. (1995) The biological effects of endogenous nerve growth factor on adult sensory neurons revealed by a trkA-IgG fusion molecule, *Nature Med.* 1(8), 774-780.
6. Okuse, K., Chaplan, S. R., McMahon, S. B., Luo, Z. D., Calcutt, N. A., Scott, B. P., Akopian, A. N., Wood, J. N. (1997) Regulation of expression of the sensory neuron-specific sodium channel SNS sodium channel in inflammatory and neuropathic pain., *Mol. Cell. Neurosci.* 10(3-4), 196-207.
7. Masiakowski, P., Shooter, E. M. (1988) Nerve growth factor induces the genes for two proteins related to a family of calcium-binding-proteins in PC12 cells, Proc. *Natl. Acad. Sci. U.S.A.* 85(4), 1277-1281.
8. Wu, T., Angus, C. W. Yao, X. L., Logun, C., Shelhamer, J. H. (1997) P11, a unique member of the S100 family of calcium-binding proteins, interacts with and inhibits the activity of the 85-kDa cytosolic phospholipase A2., *J. Biol. Chem.* 272(27), 17145-17153.
9. Akiba, S., Hatazawa, R., Ono, K., Hayama, M., Matsui, H., Sato, T. (2000) Transforming growth factor-α stimulates prostaglandin generation through cytosolic phospholipase A2 under the control of p11 in rat gastric epithelial cells., *Br. J. Pharmacol.* 131, 1004-1010.
10. Moreno J J. (2000) Antiflammin peptides in the regulation of inflammatory response., *Ann. N.Y. Acad. Sci.* 923, 47-53.
11. Kong, H. et al. An evolutionarily conserved transmembrane protein that is a novel downstream target of neurotrophin and ephrin receptors. *J. Neurosci.* 21, 176-185 (2001).
12. Liu, C. j., Dib-Hajj, S. D., Waxman, S. G. Fibroblast growth factor homologous factor 1B binds to the C terminus of the tetrodotoxin-resistant sodium channel rNav1.9a (NaN). J. Biol. Chem. 276, 18925-18933 (2001).
13. Lewin, G. R., Rueff, A. & Mendell, L. M. Peripheral and central mechanisms of NGF-induced hyperalgesia. *Eur. J. Neurosci.* 6, 1903-1912. (19)
14. Black J A et al. NGF has opposing effects on Na$^+$ channel III and SNS gene expression in spinal sensory neurons. *Neuroreport;* 8, 2331-5. (1997)
15. Fang, X. et al. Sensory and electrophysiological properties of DRG neurones with SNS-like immunoreactivity (SNS-LI) in rats. *Soc. Neurosci. Abstr.* 819.5 (2001).
16. Fjell, J. et al. In vivo NGF deprivation reduces SNS expression and TTX-R sodium currents in IB4-negative DRG neurons. J. Neurophysiol. 81, 803-810 (1999).

The invention claimed is:

1. A method of identifying a modulator of a voltage gated sodium channel (VGSC), which method comprises:
   (a) providing a cell expressing (i) a VGSC comprising amino acids 74 to 103 of SEQ ID NO: 6 and (ii) a p11 peptide comprising amino acids 33 to 77 of SEQ ID NO: 8, wherein at least said p11 peptide is expressed from a vector introduced into the cell;
   (b) bringing into contact said cell and a test compound under in vitro conditions where the VGSC and the p11 peptide are capable of forming a complex in the absence of the test compound; and
   (c) measuring an activity of the VGSC, wherein a change in the activity of the VGSC relative to the activity in the absence of the test compound indicates that the test compound is a modulator of said VGSC.

2. A method according to claim 1 wherein said activity is the ability of the VGSC to form a complex with the p11 peptide.

3. A method according to claim 1 wherein said activity is the ability of the VGSC to mediate a sodium current across a membrane.

4. A method according to claim 1 wherein a decrease in the activity of the VGSC indicates that the test compound is an inhibitor of said VGSC.

5. A method according to claim 1 wherein said VGSC is provided in a cell under in vitro conditions in which the functional expression of said VGSC has been enhanced by increasing the level of p11 peptide in the cell.

6. A method according to claim 1 wherein said cell endogenously expresses said VGSC.

7. A method according to claim 1 comprising:
   (i) bringing into contact the VGSC, the p11 peptide, and a putative modulator compound under in vitro conditions where the VGSC and the p11 peptide, in the absence of modulator, are capable of forming a complex; and
   (ii) measuring the degree of inhibition of complex formation caused by said modulator compound.

8. A method according to claim 1 comprising:
   (i) bringing into contact the VGSC, the p11 peptide, and a putative modulator compound in vitro under conditions where the VGSC and the p11 peptide, in the absence of modulator, are capable of forming a complex;
   (ii) exposing the VGSC to a stimulus such as to produce a sodium current across a membrane in which the VGSC is present; and
   (iii) measuring the degree of inhibition of the current caused by said modulator compound.

9. A method according to claim 1 wherein said VGSC and said p11 peptide are expressed from one or more heterologous expression vectors introduced into said cell.

10. A method according to claim 1 wherein said VGSC comprises amino acids 1 to 127 of SEQ ID NO: 6.

11. A method according to claim 1 wherein said VGSC comprises SEQ ID NO: 6.

12. A method according to claim 1 wherein said p11 peptide comprises SEQ ID NO: 8.

13. A method according to claim 1 wherein said VGSC comprises amino acids 1 to 127 of SEQ ID NO: 6 and said p11 peptide comprises SEQ ID NO: 8.

14. A method according to claim 1 wherein said VGSC comprises SEQ ID NO: 6 and said p11 peptide comprises SEQ ID NO: 8.

15. An isolated host cell expressing a voltage gated sodium channel (VGSC) comprising amino acids 74 to 103 of SEQ ID NO: 6 and a p11 peptide comprising amino acids 33 to 77 of SEQ ID NO: 8, wherein at least said p11 peptide is expressed from a heterologous expression vector within said cell.

16. The host cell of claim 15 wherein both said VGSC and said p11 peptide are expressed from one or more heterologous expression vectors within said cell.

17. The host cell of claim 15 wherein said VGSC comprises amino acids 1 to 127 of SEQ ID NO: 6.

18. The host cell of claim 15 wherein said VGSC comprises SEQ ID NO: 6.

19. The host cell of claim 15 wherein said p11 peptide comprises SEQ ID NO: 8.

20. The host cell of claim 15 wherein said VGSC comprises amino acids 1 to 127 of SEQ ID NO: 6 and said p11 peptide comprises SEQ ID NO: 8.

21. The host cell of claim 15 wherein said VGSC comprises SEQ ID NO: 6 and said p11 peptide comprises SEQ ID NO: 8.

22. The host cell of claim 15 wherein said cell endogenously expresses said VGSC.

* * * * *